US011379985B2

(12) United States Patent
Wang et al.

(10) Patent No.: US 11,379,985 B2
(45) Date of Patent: Jul. 5, 2022

(54) SYSTEM AND COMPUTER-IMPLEMENTED METHOD FOR SEGMENTING AN IMAGE

(71) Applicant: King's College London, London (GB)

(72) Inventors: Guotai Wang, London (GB); Tom Vercauteren, London (GB); Sebastien Ourselin, London (GB); Wenqi Li, London (GB); Lucas Fidon, London (GB)

(73) Assignee: King's College London, London (GB)

( * ) Notice: Subject to any disclaimer, the term of this patent is extended or adjusted under 35 U.S.C. 154(b) by 218 days.

(21) Appl. No.: 16/622,782

(22) PCT Filed: Jun. 14, 2018

(86) PCT No.: PCT/GB2018/051631
§ 371 (c)(1),
(2) Date: Dec. 13, 2019

(87) PCT Pub. No.: WO2018/229490
PCT Pub. Date: Dec. 20, 2018

(65) Prior Publication Data
US 2020/0167930 A1 May 28, 2020

(30) Foreign Application Priority Data
Jun. 16, 2017 (GB) .................................. 1709672

(51) Int. Cl.
*G06T 7/11* (2017.01)
*G16H 30/40* (2018.01)
(Continued)

(52) U.S. Cl.
CPC .............. *G06T 7/11* (2017.01); *G06N 3/0454* (2013.01); *G06N 3/08* (2013.01); *G16H 30/40* (2018.01);
(Continued)

(58) Field of Classification Search
CPC . G06T 7/11; G06T 7/0012; G06T 7/12; G06T 7/143; G06T 7/149;
(Continued)

(56) References Cited

U.S. PATENT DOCUMENTS

| | | | |
|---|---|---|---|
| 2015/0110392 A1* | 4/2015 | Wang | G06T 7/149 |
| | | | 382/164 |
| 2019/0304098 A1* | 10/2019 | Chen | G06V 10/454 |
| 2019/0370965 A1* | 12/2019 | Lay | G06N 20/00 |

FOREIGN PATENT DOCUMENTS

| | | |
|---|---|---|
| CN | 107590813 A | 1/2018 |
| WO | 2018229490 A1 | 12/2018 |

OTHER PUBLICATIONS

Wang, G., et al., DeepIGeoS: A Deep 1-16, Interactive Geodesic Framework for Medical 24-30 Image Segmentation 11, IEEE Transactions on Pattern Anal VS is and Machine I Ntelligence, pp. 1-1 (2018).

(Continued)

*Primary Examiner* — Ajibola A Akinyemi
(74) *Attorney, Agent, or Firm* — Hamilton, Brook, Smith & Reynolds, P.C.

(57) ABSTRACT

A computer-implemented method for segmenting an input image, the method comprises: generating a first segmentation of the input image using a first machine learning system, the first segmentation comprising multiple segments; receiving, from a user, at least one indication, wherein each indication corresponds to a particular segment from the multiple segments, and indicates one or more locations of the input image as belonging to that particular segment; constructing, for each segment of the multiple segments having at least one corresponding indication, a respective geodesic distance map, based on the input image and the user indications received for that segment; and generating a (Continued)

second segmentation using a second machine learning system based on the input image and the constructed geodesic distance maps.

18 Claims, 44 Drawing Sheets

(51) Int. Cl.
 *G06N 3/04* (2006.01)
 *G06N 3/08* (2006.01)
(52) U.S. Cl.
 CPC ............. *G06T 2207/20081* (2013.01); *G06T 2207/20084* (2013.01); *G06T 2207/20104* (2013.01)
(58) Field of Classification Search
 CPC ........... G06T 2207/10081; G06T 7/136; G06T 2207/10016; G06T 2207/20076; G06T 7/248; G06T 2207/20084; G06T 2207/20116; G06T 7/194; G06T 2207/20081; G06T 19/00; G06T 2207/10024; G06T 7/0014; G06T 7/60; G06T 11/005; G06T 11/008
 USPC ......................................................... 382/128
 See application file for complete search history.

(56) References Cited

OTHER PUBLICATIONS

International Search Report and Written Opinion for Application No. PCT/GB2018/051631, entitled "A System and Computer-Implemented Method for Segmenting an Image," dated Nov. 28, 2018.
Sharma, N., et al., "Automated Medical Image Segmentation Techniques," Journal of Medical Physics, vol. 35, No. 1, pp. 3-14 (Jan. 2010).
Zhao F. et al., "An Overview of Interactive Medical Image Segmentation," Annals of the BMVA, vol. 2013, No. 7, pp. 1-22 (2013).
Boykov, Y. et al., "Interactive Graph Cuts for Optimal Boundary & Region Segmentation of Objects in N-D Images," Computer Vision, ICCV 2001, Proceedings. Eighth IEEE International Conference, vol. 1, pp. 105-112 (2001).
Xu, C., et al., "Snakes, Shapes, and Gradient Vector Flow," IEEE Transactions on Image Processing, vol. 7, No. 3 pp. 359-369 (Mar. 1998).
Grady, Leo, "Random Walks for Image Segmentation," IEEE Transactions on Pattern Analysis and Machine Intelligence, vol. 28, No. 22, pp. 1768-1783 (Nov. 2006).
Criminisi, A., et al., "GeoS: Geodesic Image Segmentation," ECCV 2008, Part I, LNCS 4302, pp. 99-112 (2008).
Rother, C., et al., "'Grab Cut' Interactive Foreground Extraction Using Iterated Graph Cuts," ACM Transactions on Graphics, pp. 309-314 (Aug. 2004).
Wang, G., et al., "Slic-Seg: A Minimally Interactive Segmentation of the Placenta from Sparse and Motion-Corrupted Fetal MRI in Multiple Views," Medical Image Analysis 34, pp. 137-147 (2016).
Wang, B., et al., "4D Active Cut: An Interactive Tool for Pathological Anatomy Modeling," Proc IEEE Int Symp Biomed Imaging, pp. 529-532 (Apr. 2014).
Girshick, R., et al., "Rich Feature Hierarchies for Accurate Object Detection and Semantic Segmentation," Proceedings of the IEEE Conference on Computer Vision and Pattern Recognition (CVPR), pp. 580-587 (2014).
Long, J., et al., "Fully Convolutional Networks for Semantic Segmentation," Proceedings of the IEEE Conference on Computer Vision and Pattern Recognition (CVPR), pp. 3431-3440 (2015).

Chen, L. et al., "Semantic Image Segmentation with Deep Convolutional Nets and Fully Connected CRFs," Published as a Conference Paper at ICLR (2015).
Havaei, M. et al., "Brain Tumor Segmentation with Deep Neural Networks," Medical Image Analysis 35, pp. 18-31 (2017).
Kamnitsas, K., et al., "Efficient Multi-scale 3D CNN with Fully Connected CFR for Accurate Brain Lesion Segmentation," Medical Image Analysis 36, pp. 61-78 (2017).
Yu, F., et al., "Multi-scale Context Aggregation by Dilated Convolutions," Published as a Conference Paper at ICLR (2016).
Chen, L., et al., "DeepLab: Semantic Image Segmentation with Deep Convolutional Nets, Atrous Convolution, and Fully Connected CFRs," Published as a Conference Paper at ICLR (2015).
Zheng, S., et al., "Conditional Random Fields as Recurrent Neural Networks," IEEE International Conference on Computer Vision (ICCV), pp. 1529-1537 (2015).
Cicek, O., et al., "3D U-Net: Learning Dense Volumetric Segmentation from Sparse Annotation," Medical Image Computing and Computer-Assisted Intervention—MICCAI (2016).
Lin, D., et al., "ScribbleSup: Scribble-Supervised Convolutional Networks for Semantic Segmentation," IEEE Conference on Computer Vision and Pattern Recognition (2016).
Rajchl, M., et al., "DeepCut Object Segmentation From Bounding Box Annotations Using Convolutional Neural Networks," IEEE Transactions on Medical Imaging, vol. 36, No. 2, pp. 674-683 (2017).
Xu, N., et al., "Deep Interactive Object Selection," IEEE Conference on Computer Vision and Pattern Recognition, pp. 374-381 (2016).
LeCun, Y., et al., "Backpropagation Applied to Handwiillen Zip Code Recognition," Neural Computation 1, pp. 541-551 (1989).
Krizhevsky, A., et al., "ImageNet Classification with Deep Convolutional Neural Networks," Published as a Conference Paper at Advances in Neural Information Processing Systems 25 (NIPS) (2012).
Simonyan, K., et al., "Very Deep Convolutional Networks for Large-Scale Image Recognition," Published as a Conference Paper at ICLR, pp. 1-14 (2015).
Szegedy, C., et al., "Going Deeper with Convolutions," Published as a Conference Paper at IEEE Conference on Computer Vision and Pattern Recognition (CVPR) (2015).
He, K., et al., "Deep Residual Learning for Image Recognition," Published as a Conference Paper at IEEE Conference on Computer Vision and Pattern Recognition (2016).
Prasoon, A., et al., "Deep Feature Learning for Knee Cartilage Segmentation Using a Triplanar Convolutional Neural Network," Medical Image Computing and Computer-Assisted Intervention—MICCAI, Lecture Notes in Computer Science, vol. 8150, Springer (2013).
Hariharan, B., et al., "Simultaneous Detection and Segmentation," Computer Vision—ECCV, Lecture Notes in Computer Science, vol. 8695, Springer (2014).
Ronneberger, O., et al., "U-Net: Convolutional Networks for Biomedical Image Segmentation," Medical Image Computing and Computer-Assisted Intervention—MICCAI, Lecture Notes in Computer Science, vol. 9351, Springer (2015).
Milletari, F., et al., "V-Net: Fully Convolutional Neural Networks for Volumetric Medical Image Segmentation," Fourth International Conference on 3D Vision (3DV), pp. 565-571 (2016).
Ondruska, P., et al., "End-to-End Tracking and Semantic Segmentation Using Recurrent Neural Networks," arXiv: Learning (2016).
Dai, J., et al, "Instance Sensitive Fully Convolutional Networks," Computer Vision—ECCV: 14th European Conference, Proceedings, Part VI, pp. 534-549 (2016).
Lea, C., et al., "Temporal Convolutional Networks: A Unified Approach to Action Segmentation," Computer Vision—ECCV 2016 Workshops, Lecture Notes in Computer Science, vol. 9915, Springer (2016).
Lin, G., et al., "Efficient Piecewise Training of Deep Structured Models for Semantic Segmentation," 2016 IEEE Conference on Computer Vision and Pattern Recognition (CVPR), pp. 3194-3203 (2016).

(56) References Cited

OTHER PUBLICATIONS

Pinheiro, P., et al., Recurrent Convolutional Neural Networks for Scene Labeling, Proceedings of the 31st International Conference on Machine Learning, JMLR: W&CP vol. 32 (2014).

Hariharan, B., et al., "Hypercolumns for Object Segmentation and Fine-grained Localization," Proceedings of the IEEE Conference on Computer Vision and Pattern Recognition (CVPR), pp. 447-456 (2015).

Armstrong, C., et al., "Interactive Segmentation of Image Volumes with Live Surface," Computers & Graphics, vol. 31, Issue 2, pp. 212-229 (2007).

Cates, J., et al., "GIST: An Interactive, GPU-based Level Set Segmentation Tool for 3D Medical Images," Medical Image Analysis 8, pp. 217-231 (2004).

Haider, S.A., et al., "Single-Click, Semi-Automatic Lung Nodule Contouring Using Hierarchical Conditional Random Fields," IEEE 12th International Symposium on Biomedical Imaging (ISBI), pp. 1139-1142 (2015).

Bai, X., et al., "A Geodesic Framework for Fast Interactive Image and Video Segmentation and Matting," IEEE 11th International Conference on Computer Vision, pp. 1-8 (2007).

Barinova, O., et al., "Online Random Forest for Interactive Image Segmentation," International Workshop on Experimental Economics and Machine Learning, Leuven (2012).

Wang, L., et al., "4D Multi-Modality Tissue Segmentation of Serial Infant Images," PLoS ONE 7(9): e44597. doi:10.1371/journal.pone.0044597 (2012).

Boykov, Y., et al., "An Experimental Comparison of Min-Cut/Max-Flow Algorithms for Energy Minimization in Vision," IEEE Transactions on PAMI, vol. 26, No. 9, pp. 1124-1137 (Sep. 2004).

Yuan, J., et al., "A Study on Continuous Max-Flow and Min-Cut Approaches," 2010 IEEE Computer Society Conference on Computer Vision and Pattern Recognition, pp. 2217-2224 (2010).

Toyoda, T., et al., "Random Field Model for Integration of Local Information and Global Information," IEEE Transactions on Pattern Analysis and Machine Intelligence, vol. 30, No. 8, pp. 1483-1489 (Aug. 2008).

Krahenbuhl, P., et al., "Efficient Interference in Fully Connected CRFs with Gaussian Edge Potentials," Advances in Neural Information Processing Systems 24, pp. 109-117 (2011).

Szummer, M., et al., "Learning CRFs Using Graph Cuts," ECCV, Proceedings of the 10th European Conference on Computer Vision: Part II, pp. 582-595, (Oct. 2008).

Orlando, J., et al., "Learning Fully-Connected CRFs for Blood Vessel Segmentation in Retinal Images," Medical Image Computing and Computer-Assisted Intervention—MICCAI, Lecture Notes in Computer Science, vol. 8673, Springer (2014).

Domke, Justin, "Learning Graphical Model Parameters with Approximate Marginal Interference," IEEE Transactions on Pattern Analysis and Machine Intelligence, vol. 35, No. 10 (Oct. 2013).

Adams, A., et al., "Fast High-Dimensional Filtering Using the Permutohedral Lattice," Computer Graphics Forum, vol. 29, No. 2 (2010).

Vemulapalli, R., et al., "Gaussian Conditional Random Field Network for Semantic Segmentation," 2016 IEEE Conference on Computer Vision and Pattern Recognition, pp. 3224-3233 (2016).

Liu, F., et al., "Deep Convolutional Neural Fields for Depth Estimation from a Single Image," 2015 IEEE Conference on Computer Vision and Pattern Recognition (CVPR), pp. 5162-5170 (2015).

Kirillov, A., et al, "Efficient Likelihood Learning of a Generic CNN-CRF Model for Semantic Segmentation," Published as a Conference Paper at ICLR (2016).

Kolmogorov, V., et al, "What Energy Functions Can Be Minimized via Graph Cuts?" IEEE Transactions on Pattern Analysis and Machine Intelligence, vol. 26, No. 2, pp. 147-159 (Feb. 2004).

Han, D., et al., "Globally Optimal Tumor Segmentation in PET-CT Images: A Graph-Based Co-segmentation Method," Inf Process Med Imaging, 22: 245-256 (2011).

Jia, Y., et al., "Caffe: Convolutional Architecture for Fast Feature Embedding," Proceedings of the 22nd ACM International Conference on Multimedia, pp. 675-678 (Nov. 2014).

Deprest, J., et al., "The Making of Fetal Surgery," Prenat Diagn, 30: pp. 653-667 (2010).

Alansary, A., et al., "Fast Fully Automated Segmentation of the Human Placenta from Motion Corrupted MRI," Medical Image Computing and Computer-Assisted Intervention—MICCAI, pp. 589-597 (2016).

Wang, G., et al., "Dynamically Balanced Online Random Forests for Interactive Scribble-Based Segmentation," Medical Image Computing and Computer-Assisted Intervention—MICCAI, pp. 352-360 (2016).

Keraudren, K., et al., "Automated Fetal Brain Segmentation from 2D MRI Slices for Motion Correction," NeuroImage 101, pp. 633-643 (2014).

Suzuki, K., et al., "Image-Processing Technique for Suppressing Ribs in Chest Radiographs by Means of Massive Training Artificial Neural Network (MTANN)," IEEE Transactions on Medical Imaging, vol. 25, No. 4 (Apr. 2006).

Van Ginneken, B., et al., "Segmentation of anatomical structures in chest radiographs using supervised methods: a comparative study on a public database," Medical Image Analysis 10, pp. 19-40 (2006).

Hogeweg, L., et al., "Clavicle Segmentation in Chest Radiographs," Medical Image Analysis 16, pp. 1490-1502 (2012).

Gal, Y., et al., "Dropout as a Bayesian Approximation: Representing Model Uncertainty in Deep Learning," Proceedings of the 33rd International Conference on Machine Learning, vol. 48 (2016).

Tajbakhsh, N., et al., "Convolutional Neural Networks for Medical Image Analysis: Full Training or Fine Tuning?" IEEE Transactions on Medical Imaging, vol. 35, No. 5, pp. 1299-1312 (2016).

Pereira, S., et al., "Brain Tumor Segmentation Using Convolutional Neural Networks in MRI Images," IEEE Transactions on Medical Imaging, vol. 35, No. 5 (May 2016).

Chen, H., et al., "VoxResNet: Deep Voxelwise Residual Networks for Volumetric Brain Segmentation," NeuroImage 170, pp. 1-9 (Apr. 2017).

Havaei, M., et al., "HeMIS: Hetero-Modal Image Segmentation," Medical Image Computing and Computer-Assisted Intervention—MICCAI (2016).

Ioannou, Y., et al., "Decision Forests, Convolutional Networks and the Models in-Between," Microsoft Research Technical Report (2015).

Ioannou, Y., et al., "Deep Roots: Improving CNN Efficiency with Hierarchical Filter Groups," 2017 IEEE Conference on Computer Vision and Pattern Recognition (CVPR), pp. 5977-5986 (2017).

Smith, L., et al., "Deep Convolutional Neural Network Design Patterns," Under review as a Conference Paper at ICLR (2017).

Dou, Q., et al., "Automatic Detection of Cerebral Microbleeds from MR Images via 3D Convolutional Neural Networks," IEEE Transactions on Medical Imaging, vol. 35, No. 5 (May 2016).

Merkow, J. et al., "Dense Volume-to-Volume Vascular Boundary Detection," Medical Image Computing and Computer-Assisted Intervention—MICCAI, pp. 371-379 (2016).

Kleesiek, J., et al., "Deep MRI Brain Extraction: A 3D Convolutional Neural Network for Skull Stripping," NeuroImage 129, pp. 460-469 (2016).

Sankaran, S., et al., "Real-Time Sensitivity Analysis of Blood Flow Simulations to Lumen Segmentation Uncertainty," International Conference on Medical Image Computing and Computer-Assisted Intervention—MICCAI, Lecture Notes in Computer Science, vol. 8674, Springer, pp. 1-8 (2014).

Shi, W., et al., "A Multi-image Graph Cut Approach for Cardiac Image Segmentation and Uncertainty Estimation," Statistical Atlases and Computational Models of the Heart, Imaging and Modeling Challenges, STACOM, Lecture Notes in Computer Science, vol. 7085, Springer, pp. 178-187 (2012).

He, K., et al., "Identity Mappings in Deep Residual Networks," Computer Vision—ECCV, Lecture Notes in Computer Science, vol. 9908, Springer (2016).

(56) References Cited

OTHER PUBLICATIONS

Veit, A., et al., "Residual Networks Behave Like Ensembles of Relatively Shallow Networks," NIPS'16: Proceedings of the 30th International Conference on Neural Information Processing Systems, pp. 550-558 (Dec. 2016).

Luo, W., et al., "Understanding the Effective Receptive Field in Deep Convolutional Neural Networks," 30th Conference on Nerual Information Processing Systems (NIPS) (2016).

Ioffe, S., et al., "Batch Normalization: Accelerating Deep Network Training by Reducing Internal Covariate Shift," Proceedings of the 32nd International Conference on Machine Learning, vol. 37, pp. 448-456 (2015).

Nyul, L., et al., "New Variants of a Method of MRI Scale Standardization," IEEE Transactions on Medical Imaging, vol. 19, No. 2 (Feb. 2000).

Kingma, D., et al., "ADAM: A Method for Stochastic Optimization," Published as a Conference Paper at ICLR (2015).

Cardoso, M., et al., "Geodesic Information Flows: Spatially-Variant Graphs and Their Application to Segmentation and Fusion," IEEE Transactions on Medical Imaging, vol. 34, No. 9 (Sep. 2015).

Li, Y., et al., "Lazy Snapping," ACM Transactions on Graphics, pp. 303-308 (Aug. 2004).

Adams, R., et al., "Seeded Region Growing," IEEE Transactions on Pattern Analysis and Machine Intelligence, vol. 16, No. 6; pp. 640-647 (Jun. 1994).

Vaelaert, P., "Digital Planarity of Rectangular Surface Segments," IEEE Transactions on Pattern Analysis and Machine Intelligence, vol. 16, No. 6, pp. 647 (Jun. 1994).

Ribeiro, H., et al., "Hand Image Segmentation in Video Sequence by GMM: A Comparative Analysis," IEEE Brazilian Symposium on Computer Graphics and Image Processing, pp. 357-364 (2006).

Huh, M., et al., "What Makes ImageNet Good for Transfer Learning?" Computer Science (2016).

Li, W., et al., "On the Compactness, Efficiency, and Representation of 3D Convolutional Networks: Brain parcellation as a Pretext Task," Information Processing in Medical Imaging, IPMI, Lecture Notes in Computer Science, vol. 10265, Springer, pp. 348-360 (2017).

Yushkevich, P., et al., "User-guided 3D Active Contour Segmentation of Anatomical Structures: Significantly Improved Efficiency and Reliability," NeuroImage 31, pp. 1116-1128 (2006).

Menze, B., et al., "The Multimodal Brain Tumor Image Segmentation Benchmark (BRATS)," IEEE Transactions on Medical Imaging, vol. 34, No. 10, pp. 1993-2024 (2015).

Ramirez, E., et al., "A Volume Segmentation Approach Based on GrabCut," CLEI Electronic Journal, vol. 16, No. 2, Paper 4 (Aug. 2013).

Vezhnevets, V., et al., "'GrowCut'—Interactive Multi-Label N-D Image Segmentation by Cellular Automata," Proc. Graphicon, pp. 150-156 (2005).

\* cited by examiner (a)

(b)

SYSTEM AND COMPUTER-IMPLEMENTED METHOD FOR SEGMENTING AN IMAGE

This application is the U.S. National Stage of International Application No. PCT/GB2018/051631, filed Jun. 14, 2018, which designates the U.S., published in English, and claims priority under 35 U.S.C. § 119 or 365(c) to Great Britain Application No. 1709672.8, filed Jun. 16, 2017. The entire teachings of the above applications are incorporated herein by reference.

FIELD

The present application relates to a system or apparatus and a computer-implemented method for segmenting an image, for example, for segmenting a medical image into one or more organs or other anatomical components.

BACKGROUND

Segmentation (parcellation) of anatomical structures is an important task for a range of medical image processing applications such as image-based diagnosis, anatomical structure modelling, surgical planning and guidance. Although automatic segmentation methods [1] have been investigated for many years, they rarely achieve sufficiently accurate and robust results to be useful for many medical imaging applications. This is mainly due to poor image quality (with noise, artefacts and low contrast), large variations among patients, inhomogeneous appearance due to pathology, and variability of protocols among clinicians leading to different definitions of a given structure boundary. Interactive segmentation methods, which take advantage of a user's knowledge of anatomy, are widely used for higher accuracy and robustness [2].

Although leveraging user interactions helps to obtain more precise segmentation results [3, 4, 5, 6], the resulting requirement for many user interactions increases the burden on the user. Thus a good interactive segmentation method should require as few user interactions as possible, leading to increased interaction efficiency. Machine learning methods are commonly used to reduce user interactions. For example, GrabCut [7] uses Gaussian Mixture Models to model colour distribution and only requires the user to provide a bounding box. SlicSeg [8] employs Online Random Forests to segment a Magnetic Resonance Imaging (MRI) volume by learning from user-provided scribbles in only one slice. Active learning is used in [9] to actively select candidate regions for querying the user.

Recently, deep learning techniques with convolutional neural networks (CNNs) have achieved increasing success in image segmentation [10, 11, 12]. They can find the most suitable features through automatic learning instead of manual design. By learning from large amounts of training data, CNNs have achieved state-of-the-art performance for automatic segmentation [12, 13, 14]. One of the most widely used methods is Fully Convolutional Network (FCN) [11] (a type of CNN); FCN outputs the segmentation directly by computing a forward propagation only once at testing time.

Recent advances of CNNs for image segmentation mainly focus on two aspects. The first is to overcome the problem of reduction of resolution caused by repeated combination of max-pooling and down-sampling. Though some up-sampling layers can be used to recover the resolution, this may lead to blob-like segmentation results and low accuracy for very small structures [11]. In [15, 12], dilated convolution is proposed to replace some down-sampling layers. Dilated convolution allows exponential expansion of the receptive field without loss of resolution. However, the CNNs in [15, 12] keep three layers of pooling and down-sampling, so that their output resolution is still reduced eight times compared with the input. The second aspect is to enforce inter-pixel dependency to get a spatially regularized result. This helps to recover edge details and reduce noise in pixel classification. DeepLab [16] uses fully connected Conditional Random Fields (CRFs) as a post-processing step, but its parameters rely on manual tuning which is time-consuming and may not ensure optimal values. It was shown in [17] that the CRF can be formulated as a Recurrent Neural Network (RNN), so that it can be trained end-to-end utilizing the back-propagation algorithm. However, this CRF constrains the pairwise potentials as Gaussian functions, which may be too restrictive for some complex cases, and does not apply automatic learning to all its parameters. Thus using a free-form learnable pairwise potential function and allowing automatic learning of all parameters may potentially achieve better results.

Typical CNNs, such as LeNet [22], AlexNet [23], VGG [24], GoogleNet [25] and ResNet [26], were originally designed for image classification tasks. Some early work on CNN-based segmentation adapted such networks for pixel labelling with patch or region-based methods [13, 10]. For example, [27, 28] used a CNN to classify each pixel into the target object or the background by taking a local patch centered on that pixel as input. Such methods achieve higher accuracy than traditional methods that relied on hand-crafted features, but they suffer from inefficient testing.

Instead of using image patches, FCN [11] takes the entire image as input and outputs dense segmentation. In order to overcome the problem of a reduction in spatial resolution due to multi-stage max-pooling and down-sampling, FCN uses a stack of de-convolution (a.k.a. up-sampling) layers and activation functions to up-sample the feature maps. Inspired by the convolution and de-convolution framework of FCN, a U-shape network (U-Net) [29] and its 3D version [18] have been proposed for biomedical image segmentation. A similar network (V-Net) [30] has been proposed to segment the prostate from 3D MRI volumes.

To avoid reduction of feature map resolution due to the successive max-pooling and down-sampling while keeping an exponential growth of a receptive field, dilated convolution [12] has been proposed to replace the last two down-sampling layers of the VGG network. The dilated convolution uses filters to sparsely sample the feature maps on which they are applied using an input stride. This approach has been used in [15] to preserve the resolution of feature maps and enlarge the receptive field to incorporate larger contextual information. In [31], a stack of dilated convolutions were used for object tracking and semantic segmentation; they have also been used by the instance-sensitive FCN [32] and applied to action segmentation and detection from video frames [33].

Multi-scale features extracted from CNNs have been shown to be effective for improving segmentation accuracy [11, 12, 15]. One way of obtaining multi-scale features is to pass several scaled versions of the input image through the same network. The features from all the scales can be fused for pixel classification [34]. In [13, 14], the features of each pixel were extracted from two co-centric patches with different sizes. In [35], multi-scale images at different stages were fed into a recurrent convolutional neural network. Another widely used way to obtain multi-scale features is to exploit features from different levels of the convolutional network. For example, in [36], features from intermediate layers are concatenated for segmentation and localization. In [11, 12], predictions from the final layer are combined with those from previous layers.

Interactive image segmentation has been widely used in various applications [37, 38, 20]. There are many kinds of user interactions, such as click-based [39], contour-based [4] and bounding box-based methods [7]. Drawing Scribbles is user-friendly and particularly popular, e.g., in Graph Cuts [3], GeoS [40, 6], and Random Walks [5]. Each scribble is typically input by a user as a free-form line drawn superimposed onto an image (or image plane). The scribble is not intended to delineate a segment boundary; rather the scribble is used to indicate an image region which belongs to a given segment (or alternatively, to indicate an image region which does not belong to a given segment). The scribble indicates the correct segmentation of a sample of pixels (those under the scribble), for use in a further round of machine (automatic) segmentation, rather than trying to define an exhaustive set of pixels for a given segment. This allows a scribble to be drawn quickly and without undue accuracy (assuming the scribble does not go too close to a segment boundary).

However, many of these methods rely on low-level features and require a relatively large amount of user interaction to deal with images with low contrast and ambiguous boundaries. Machine learning methods [41, 42, 8] have been proposed to learn higher-level features from user interactions, and can achieve higher segmentation accuracy with fewer user interactions. However, such systems are usually limited by hand-crafted features that depend on the user's experience.

Recently, using deep CNNs to improve interactive segmentation is attracting increasing attention due to the automatic feature learning and high performance of CNN. In [18], a 3D U-Net was proposed to learn from sparsely annotated data and can be used for semi-automatic segmentation. ScribbleSup [19] also trains CNNs for semantic segmentation supervised by scribbles. DeepCut [20] combines CNNs with user-provided bounding box annotations for image segmentation of fetal MRI. However, these methods are not fully interactive for testing, since they do not accept further interactions for refinement. In [21], a deep interactive object selection method was proposed where user-provided clicks are transformed into Euclidean distance maps and then concatenated with the input of a FCN. However, the Euclidean distance does not take advantage of image context information.

Pixel-wise or super-pixel-wise classification based on CNNs or traditional classifiers often lacks spatial consistency. To overcome this problem, graphic models such as CRFs [43, 44, 12] have been widely used to enhance the accuracy of pixel labelling tasks. In [43], a discrete Potts model was proposed for spatial regularization, where the Potts energy was minimized by a min-cut/max-flow algorithm. In [44], the discrete graph-based max-flow problem was mapped to a continuous optimization formulation that could be speeded up by parallel implementation on GPUs. Such methods encourage segmentation consistency between pixel pairs with high similarity. The pixel pairs are defined based on local neighbourhoods or patches. In order to better model long-range connections within the image, a fully connected CRF was used in [45, 46] to establish pairwise potential on all pairs of pixels in the image with a Gaussian decay. The parameters of CRFs were manually tuned in this work. In [47], a maximum margin learning method was proposed to learn CRFs using Graph Cuts. Other methods including structured output Supporter Vector Machine [48] and approximate marginal inference [49] have also been proposed to learn parameters in CRFs (they treat the learning of CRFs as an independent step after the training of classifiers).

The CRF-RNN network [17] formulated dense CRFs as RNNs so that the CNNs and CRFs could be jointly trained in an end-to-end system for segmentation. However, the pair-wise potentials in [17] are limited to weighted Gaussians and not all the parameters are trainable due to the Permutohedral lattice implementation [50]. In [51], a Gaussian Mean Field (GMF) network was proposed and combined with CNNs where all the parameters are trainable. More freeform pairwise potentials for a pair of super-pixels or image patches have been learned by neural networks [52, 34], but such CRFs have a low resolution. In [53], a generic CNN-CRF model was proposed to handle arbitrary potentials for labelling body parts in depth images, but this approach has not yet been validated for other segmentation applications.

CNNs have therefore been shown to provide good performance for automatic image segmentation tasks [10, 11, 16, 13, 14], however, only a few works have applied CNNs to interactive segmentation tasks [18, 19, 20, 21]. In addition, there have been recent advances in tailoring CNNs to analyse volumetric images. Most of the work to date studies image representations in 2D. While volumetric representations are more informative, the number of voxels scales cubically with the size of the region of interest, thereby raising challenges of learning more complex visual patterns as well as imposing a higher computational burden compared to the 2D cases. While developing compact and effective 3D network architectures is of significant interest, designing 3D CNNs remains a challenging problem. Most existing network architectures follow a fully convolutional down-sample/up-sample pathway [14,72,73,18,30,74]. Low-level features with high spatial resolution are first down-sampled for higher-level feature abstraction; then the feature maps are up-sampled to achieve high-resolution segmentation.

Additionally of interest are multimodal network architectures. Most of the existing multimodal network architectures handle imaging modalities by concatenating the intensities as an input. The multimodal information is implicitly fused by training the network discriminatively. Experiments show that, whenever multiple MR modalities are available, relying on multiple MR modalities consistently is important for achieving accurate segmentations [66]. However, using classical modality concatenation to turn a given monomodal CNN architecture into a multimodal CNN does not scale well because it either requires a dramatic augmentation of the number of hidden channels and network parameters, or imposes a bottleneck on at least one of the network layers. This lack of scalability leads to the design of dedicated multimodal architectures and makes it difficult and time-consuming to adapt state-of-the-art network architectures.

Recently, Havaei et al. [68] proposed a hetero-modal network architecture (HeMIS) that learns to embed the different modalities into a common latent space. Their work suggests that it is possible to impose more structure on the network. HeMIS separates the CNN into a backend that encodes modality-specific features up to the common latent space, and a frontend that uses high-level modality-agnostic feature abstractions. HeMIS is able to deal with missing modalities and shows promising segmentation results. However, the authors do not study the adaptation of existing networks to additional imaging modalities and do not demonstrate an optimal fusion of information across modalities.

SUMMARY

The invention is defined in the appended claims.

The approach described herein provides a system and a computer-implemented method for segmenting an input image. The method comprises: generating a first segmentation of the input image using a first machine learning system, the first segmentation comprising multiple segments; receiving, from a user, at least one indication, wherein each indication corresponds to a particular segment from the multiple segments, and indicates one or more locations of the input image as belonging to that particular segment; constructing, for each segment of the multiple segments having at least one corresponding indication, a respective geodesic distance map, based on the input image and the user indications received for that segment; and generating a second segmentation using a second machine learning system based on the input image and the constructed geodesic distance maps.

BRIEF DESCRIPTION OF THE DRAWINGS

Various embodiments of the invention will now be described by way of example only with reference to the following drawings:

FIG. 37*a* shows the label distribution of a data set analysed herein, while FIG. 37*b* shows the Dice score to compare performance of various segmentation systems in respect of this data set.

DETAILED DESCRIPTION

Figure 1:
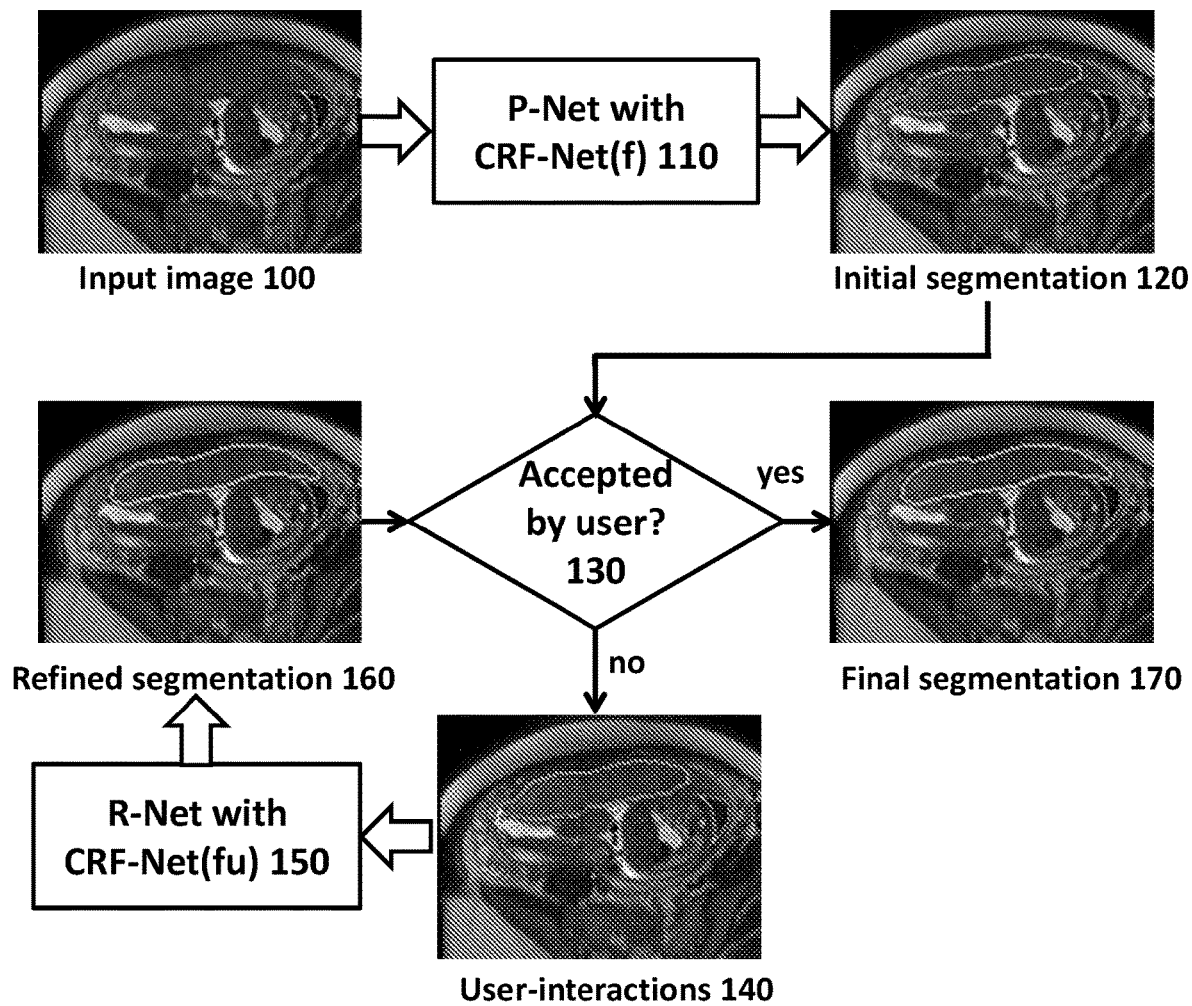
FIG. 1 shows a deep interactive geodesic distance-based segmentation method, according to an example of the present invention.

The approach described herein helps to integrate user interactions with machine learning system frameworks, for example CNN frameworks, to obtain accurate and robust segmentation of medical images, while at the same time making the interactive framework more efficient with a minimal number of user interactions. The approach therefore supports interactive image segmentation using supervised machine learning, and provides, inter alia, a system and method for segmentation of medical images using supervised machine learning techniques which can be adjusted by user interactions.

Particular aspects of the present approach are as follows:

(1) a deep machine learning-based interactive framework performs medical image segmentation. The machine learning-based segmentation is improved through integrating user interactions or indications, e.g. clicks and/or scribbles. At the same time, the framework significantly reduces the number of required interactions by using machine learning systems such as CNNs. In a particular example of this approach, a first machine learning system automatically generates an initial segmentation, which is then refined by a second machine learning system that takes as input the initial segmentation and any user interactions.

(2) user interactions are combined with the machine learning system based on geodesic distance maps. Geodesic distances of each pixel, or voxel for 3-dimensional images, to user interactions of each class are calculated and used as extra input for the machine learning system. Using geodesic distances can lead to improved segmentation accuracy compared with using Euclidean distances. Such a geodesic distance transform [40, 6] encodes spatial regularization and contrast-sensitivity (and has not previously been used or considered for CNNs).

(3) some examples of the approach described herein use a resolution-preserving machine learning system so that the image resolution is kept the same in all the convolutional layers. This can lead to a more detailed segmentation result compared with traditional CNNs that have resolution loss.

(4) furthermore, current RNN-based CRFs [17] for segmentation are extended so that the back-propagatable CRFs can use user interactions as hard constraints and all the parameters of its potential functions may be trained on an end-to-end basis.

In some implementations of a machine learning-based system described herein, segmentation of previously unseen objects (such as organs) is achieved by using image-specific fine-tuning (i.e. adaptation) to improve accuracy. The machine learning system can then be employed to segment a range of different organs using, for example, magnetic resonance (MR) or computed tomography (CT) images. An example implementation trained with the placenta and fetal brain is provided, and it is shown that such a system can be applied to segment fetal lungs and maternal kidneys that are not present in the training set. The image-specific fine-tuning improves segmentation accuracy, and outperforms GrabCut [7], which uses a similar interaction style.

In a further example, a high-resolution and compact network architecture is described for the segmentation of fine structures in volumetric images. For this purpose, the simple and flexible elements of modern convolutional networks, such as dilated convolution and residual connection, are investigated. As described herein, a 3D architecture incorporates high spatial resolution feature maps throughout the layers, and can be trained with a wide range of receptive fields. An example network is utilised for the challenging task of automated brain parcellation into 155 structures from T1-weighted MR images. As show below, the example network, with twenty times fewer parameters, achieves competitive segmentation performance compared with other existing (state-of-the-art) architectures. The example trained network represents a first step towards a general-purpose volumetric image representation and provides an initial model for transfer learning of other volumetric image segmentation tasks. Such an architecture can advantageously be used as part of a 3D interactive segmentation framework for which low computational and memory requirements are important.

A further consideration is the uncertainty of the segmentation for indicating the confidence and reliability of one algorithm [64,75,76]. The high uncertainty of labelling can be a sign of an unreliable classification. In one example implementation described herein, the feasibility of voxel-level uncertainty estimation using Monte Carlo samples of the network with dropout at test time is investigated. Compared to the existing volumetric segmentation networks, the compact network described herein has fewer parameter interactions, and thus potentially achieves better uncertainty estimates with fewer samples.

In a still further example of the present approach, a scalable network framework (ScaleNets) enables efficient refinement of an existing architecture to adapt the existing architecture to an arbitrary number of Magnetic Resonance (MR) modalities (instead of building a new architecture from scratch). ScaleNets separate a given network into a backend and frontend with across-modality information flowing through the backend, thereby alleviating the need for a one-shot latent space merging. An example scalable backend takes advantage of a factorisation of the feature space into imaging modalities (M space) and modality-conditioned features (F space). By explicitly using this factorisation, sparsity is imposed on the example network structure with demonstrated improved generalisation. Such an architecture can advantageously be used as part of a multimodal interactive segmentation framework.

The framework is further evaluated by starting from the above high-resolution and compact network described for brain parcellation from T1 MRI [71] and adapting it to brain tumour segmentation from T1, T1c, Flair and T2 MRI. In addition, the design of the modality-dependent backend is explored by comparing several important factors, including the number of modality-dependent layers, the merging function, and convolutional kernel sizes. An example implementation shows that the example networks are more efficient and scalable than conventional CNNs and achieve competitive segmentation results on the BraTS 2013 challenge dataset.

Section 1

FIG. 1 shows an example deep interactive geodesic distance-based segmentation method (DeepIGeoS). At step 100 an input image is provided. The input image may be a two-dimensional (spatial) image, or a two-dimensional image with surface distance (topographical) information (sometimes referred to as a 2.5 dimensional image). The image may also be a three dimensional spatial image, for example, presented as a series of two dimensional image planes or slices. The image may also be four-dimensional (or higher) to incorporate information on one or more additional physical parameters, such as time and/or wavelength (these one or more additional physical parameters may also be added to a 2D or 2.5D image).

The image typically records signal intensity (luminosity) according to spatial location within the image. The image may be multimodal, in that it records multiple intensity values according to spatial location for multiple respective imaging modalities, such as for different modes of magnetic resonance (MR) image, and/or to combine images from different types of images, such as X-ray (e.g. computed tomography, CT), ultrasound, gamma ray (e.g. positron emission tomography, etc). Furthermore, the image provided at step 100 may be formed from a combination of multiple different images, e.g. by averaging, mosaicking, and/or by incorporating data from different imaging modalities, as above.

Assuming a digital image, the image values are quantised to a set of locations. These locations are often referred to as pixels for an image having 2 spatial dimensions, and voxels for an image having 3 spatial dimensions. However, in the present application, the terms "pixel" and "voxel" should not be considered, by themselves, as limiting the dimensionality of the image.

At step 110 a first (initial or proposal) segmentation network (P-Net hereafter) takes as input the provided image with $C_I$ channels and automatically produces (proposes) an initial, or first, segmentation, which is presented to the user at step 120. The proposed segmentation is denoted in FIG. 1 by the green line (and is discussed in more detail below with reference to FIG. 2).

At step 130 the user checks the initial segmentation and either accepts the segmentation as correct, or proceeds to step 140 where the user provides some interactions (indications), e.g. clicks or scribbles, with the system to indicate mis-segmented regions. In FIG. 1, the user interactions are coloured red and cyan: the former indicating a region that should be within the segmentation defined by the green line, the latter indicating a region that should be outside the segmentation defined by the green line (these indications are likewise discussed in more detail below with reference to FIG. 2).

At step 150 a second (refinement) segmentation network (R-Net hereafter) uses the information of the original input image (as provided at step 100), the initial segmentation (as proposed at step 120) and the user interactions (as received at step 140) to provide a refined segmentation. At step 160 the second (refined) segmentation is presented to the user, and the method then returns to step 130. At this point, the user either accepts the refined segmentation or provides more interactions to refine the result at least one more time through R-Net, in effect, having another cycle (iteration) through steps 140, 150 and 160 to 130. Once the user accepts the refined segmentation at step 130, the method proceeds to step 170 which finalises the segmentation.

In some implementations, P-Net and R-Net share the same structure, based on using a back-propagatable conditional random field (CRF) having a freeform (f) pairwise potential within a convolutional neural network (CNN). In addition, P-Net and R-Net both use a resolution-preserving structure that captures high-level features from a large receptive field without loss of resolution. However, P-Net and R-Net differ in their input dimensions: both networks receive the original input image, but R-Net further receives the proposed segmentation (from P-Net, or potentially from a previous iteration by itself), together with the user interactions (u) for the proposed segmentation, the latter being considered as hard constraints.

Figure 2:
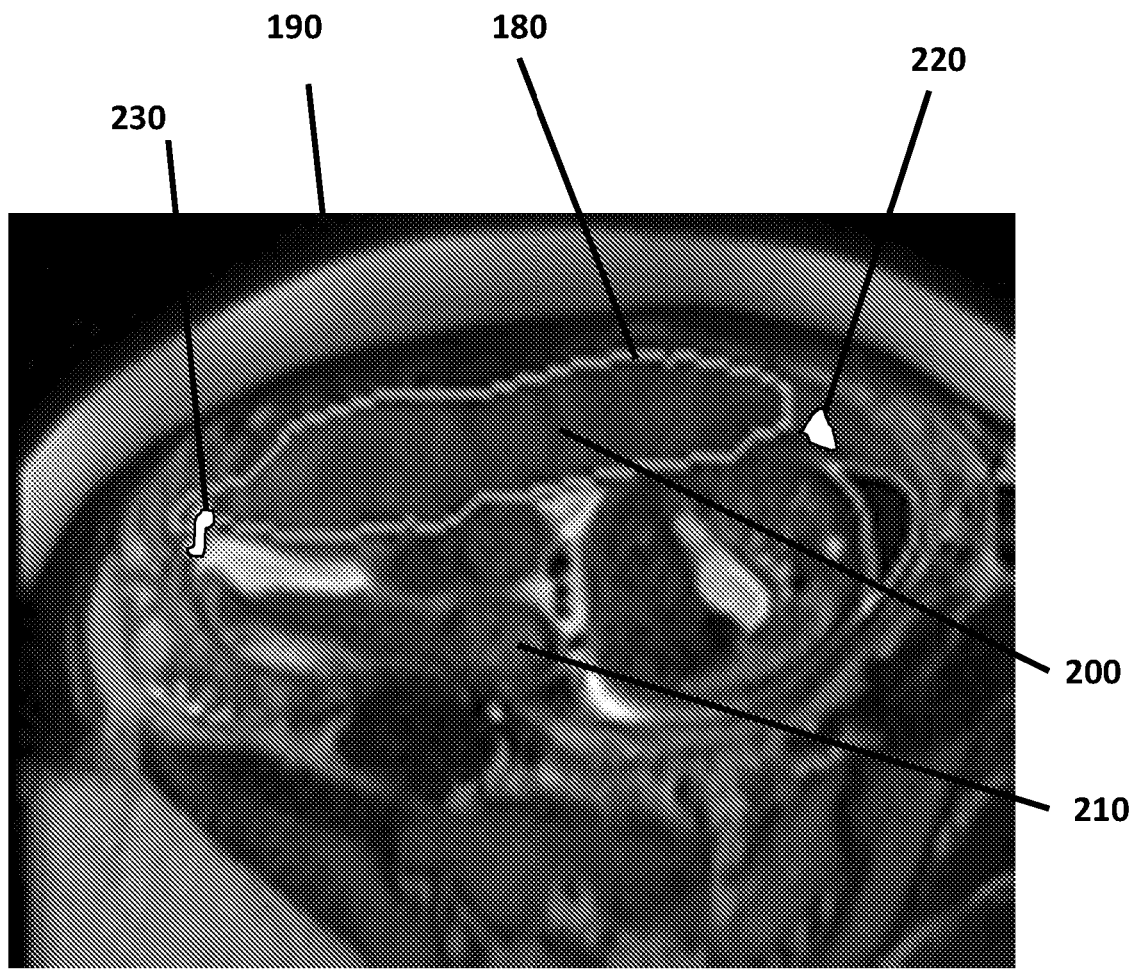
FIG. 2 shows an example of user indications of incorrect segmentation in accordance with the example method of FIG. 1.

FIG. 2 shows an example of indications provided by a user (as user interactions) in accordance with step 140 of FIG. 1 (apart from the addition of reference numerals, FIG. 2 is an enlarged version of the image shown for step 140 of FIG. 1). Thus at step 130 of FIG. 1, the user is provided with the initial (proposed) segmentation from step 120 overlaid or superimposed on the original input image from step 100. In the example of FIG. 2, the input image is indicated as 190, and the initial (proposed) segmentation is indicated as 180 as a single closed shape. This segmentation 180 therefore divides the input image 190 into a first segment 200, corresponding to the inside of the closed shape defined by line 180, and a second segment 210, corresponding to the portion of the image outside the closed shape. The first segment 200 may be considered as a "foreground", representing an object (e.g. organ) of interest, while the second segment 210 may be considered as a "background", in other words, representing everything else (other than the object of interest).

Although FIG. 2 illustrates a binary segmentation, in which each image location (pixel) belongs to one of two segments, i.e. either the first or second segment. Such binary segmentation is common in situations in which the main focus is on a single object or organ, which then represents the foreground, with the remainder of the image then representing the background. However, the approach described herein extends beyond binary segmentation to work with any desired number of segments. For example, there may be interest in identifying and segmenting a number of different organs or objects within a body, and/or for identifying and segmenting objects or structures within an object, such as segmenting the various lobes of the brain.

If at operation 130, the user does not accept the initial segmentation, the user may give one or more indications of any image region which has been mis-segmented. For example, FIG. 2 shows a first indication 220 coloured red, and a second indication 230 coloured cyan. The first indication 220 denotes an image region which should be part of the first segment (foreground), i.e. inside segmentation line 180, while the second indication denotes an image region which should be part of the second segment (background), i.e. outside segmentation line 180.

More particular, an indicated region (such as that denoted by first indication 220 or second indication 230) belongs to a particular segment. In the proposed segmentation, the indicated region might lie inside or outside the particular segment, or may do both and straddle the boundary of the particular segment (such as indication 230 in FIG. 2). However, indications provided outside the particular segment are primarily used for producing a refined segmentation, because such indications denote a region which has been mis-segmented in the proposed segmentation.

With this approach, the user first selects a particular segment, and provides corresponding indications for that segment, and then selects another segment, and provides corresponding indications for that segment, and so on. This approach would generally involve some form of labelling for the indications, to show which indications correspond to which segment. One way of doing this is to use different colours for different segments, such as shown in FIG. 2—the red indication 220 belongs to the first segment 200, the cyan indication 230 belongs to the second segment 210.

Note that a user may not provide indications for every segment. For example, we may have a binary segmentation into foreground and background segments, where the proposed segmentation of the foreground object of interest lies wholly within the true foreground segment. In this case, the user indications would typically be limited to the foreground segment, to show foreground regions that have been incorrectly assigned to the background in the proposed segment (but without providing indications for the background segment).

In the approach shown in FIG. 2, and as described above, the first indication 220 in red denotes a region that should be included in the first segment 200, and the second indication 230 in cyan denotes a region that should be included in the second segment 210 (a part of the cyan region of the second indication 230 is already included in the second segment 210). Note that FIG. 2 shows a single indication corresponding to each segment, however, depending on the results from the proposed segmentation, there may be zero or multiple indications corresponding to a single segment—e.g. there might be two indications denoting regions that should belong to the first segment, but no indications with respect to the second segment.

Each indication denotes (defines) one or more locations (pixels) within the image that belong to a particular (corresponding) segment. The indications may be entered by using a mouse, touch-screen, or other suitable input device. In some cases, the indications might be provided by clicking on the relevant locations, the locations of the clicks then being suitably displayed on the segmented image, e.g. by crosses or points (coloured as appropriate). In other cases, the indications might be provided by 'scribbles', where each scribble represents a free-form, continuous line, such as shown in FIG. 2. Other forms of providing and labelling indications will be apparent to the skilled person. In addition, there may be some facility for a user to edit and/or delete previously entered indications, for example, in case a mistake is made when drawing a scribble.

Overall, the indications are not intended for the user to provide a complete, definitive segmentation of the image, for example, by directly marking the boundaries between segments, or exhaustively indicating all pixels in a given segment, which would generally be complex and time-consuming, especially for a 3-dimensional image. Instead, the indications provide additional information about the correct/incorrect segmentation at the pixel locations of the indications, in effect, a set of additional samples at the indicated pixel locations, which may then be utilised to produce a refined, more accurate segmentation, as per step 170 in FIG. 1.

It will now be described how the indications are used to produce a refined, more accurate segmentation from the indications in accordance with certain implementations. In these implementations, as described above, each indication corresponds to a particular segment, and the indication denotes an image location (or locations) that the user specifies as belonging to that segment. However, other implementations may potentially use other approaches for allowing indications to denote regions that have been mis-segmented in the proposed segmentation.

In the approach described herein, a distance map is created from the image for each label type, where label type corresponds to a particular segment of the image. For example, one can consider the red and cyan colouring as the label types for the first and second segments respectively. In the distance map, the value at each image location corresponds to the distance between a respective pixel of the image at that location, and the closest user indication of that label type. In [21], a distance map was produced using Euclidean distance due to its simplicity; however, Euclidean distance treats all directions equally and does not take image context (image content) into account. For example, for neighbouring pixels with different intensity, the Euclidean distance between them is very small, and therefore it may not be helpful for differentiating these pixels. However, for two pixels in a region with similar appearance, their Euclidean distance might be large, which may encourage these pixels to be labelled as different classes.

In contrast, the approach described herein uses geodesic distance for the distance map. This helps to better differentiate neighbouring pixels with different appearances, and to improve label consistency in homogeneous regions [6]. Integrating image context into distance transforms, by using geodesic distances, can help lead to better segmentation than Euclidean distances.

Supposing $S_f$ and $S_b$ represent the set of pixels belonging to foreground scribbles and background scribbles respectively (which in turn correspond to first and second segments respectively). The unsigned geodesic distance of each pixel i in an image I from the scribble set S ($S \in \{S_f, S_b\}$) may be defined as:

$$G(i,S,I) = \min_{j \in S} D_{geo}(i,j,I) \quad (1)$$

$$D_{geo}(i,j,I) = \min_{p \in P_{i,j}} \int_0^1 \|\nabla I(p(s)) \cdot u(s)\| ds \quad (2)$$

where $P_{i,j}$ is the set of all paths between pixel i and j, p is one feasible path which is parameterized by $s \in [0, 1]$; and u(s) is a unit vector which is tangent to the direction of the path and is defined as $u(s) = p'(s)/\|p'(s)\|$.

In general terms, a geodesic map is based on a path between (i) a given pixel (image location), and (ii) any pixel corresponding to an indication for the relevant segment, which has relatively low variation in intensity (and/or some other image or physical property) along its length, even if the path is not geometrically the shortest route between the two pixels. It will be appreciated that such a geodesic map can help to identify a pixel in the same segment as the indicated pixel, since it is assumed that a segment will tend to have a relatively homogeneous appearance (without discontinuities), thereby providing a comparatively low geodesic distance between two pixels that are both in the segment.

Equations (1) and (2) relate to an image of any dimensionality (including a multi-modal image). In the specific example above, only two segments are defined (foreground and background), however, Equations (1) and (2) may be readily applied to N segments (N≥2) by writing the scribble set as S ($S \in \{S_1, \ldots S_N\}$). In addition, equation (2) uses the gradient of the image ($\nabla I$) as the parameter for determining geodesic distance. However, the gradient represents only one example of a local discrepancy measure, and any other suitable measure could be used instead. As noted above, the user may not provide indications for one or more label types. In this case, the corresponding geodesic distance map may be populated with suitable homogeneous data having only small local variations (if any), for example, random numbers, constant numbers (e.g. 0) and so on, that do not provide any bias to the segmentation.

Figure 3:
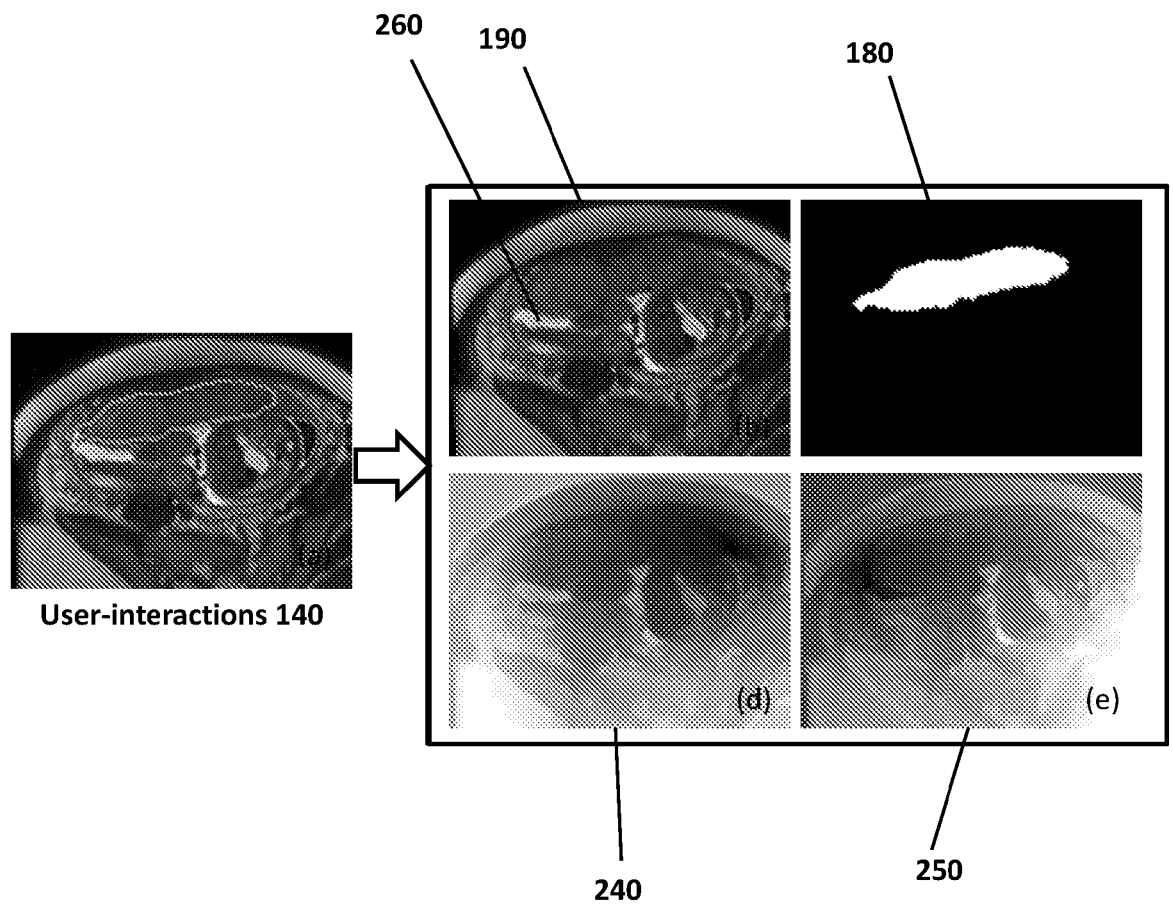
FIG. 3 shows an example of the collective inputs to a second segmentation network, R-Net, in accordance with the example method of FIG. 1.

FIG. 3 shows an example of the inputs to the second segmentation network, R-Net, for the refined segment of operation 160 of FIG. 1 following receipt of the user interactions (indications) at operation 140 of FIG. 1 (see image (a) in FIG. 3, left). For the case shown in FIG. 2, the second segmentation network takes four inputs: the original input image 190 (see image (b) in FIG. 3, top centre), the initial (proposed) segmentation 180 (see image (c) in FIG. 3, top right), a first geodesic distance map 240 corresponding to the first (foreground) segment 200 (see image (d) in FIG. 3, bottom centre), and a second geodesic distance map 250 corresponding to the second (background) segment 210 (see image (e) in FIG. 3, bottom right). The values of the first geodesic distance map 240 are calculated according to geodesic distance from the first indication 220 (see FIG. 2), as per Equations 1 and 2 above.

Region 260 shown in the original image 190 is relatively light. This region is also relatively light in the first distance map 24, but much darker in the second distance map. The former light colour (high value) arises because region 260 is both a relatively long way from first indication 220, and also dissimilar in brightness (intensity). The latter low value arises because region 260 is both relatively close to the second indication 230, and also somewhat similar in brightness to the second indication 230.

Figure 4:
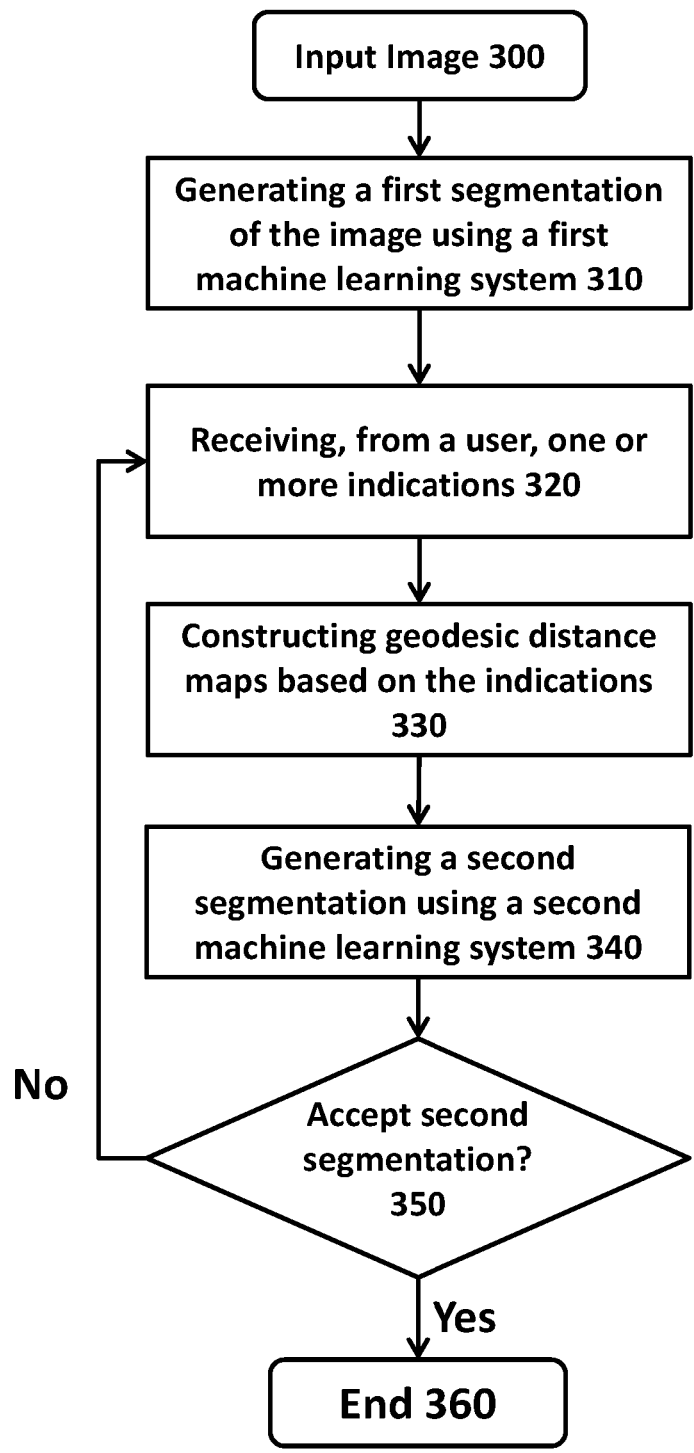
FIG. 4 shows a flowchart of a method according to an example of the present invention.

The geodesic distance maps 240,250 derived from the user interactions (indications) and the initial (proposed) segmentation 180 have the same height and width as the input image 190, I. These inputs of FIG. 4 are then concatenated with the channels of I so that an image I' with $C_I$+3 channels is obtained (I' then being used as the input of the refinement network R-Net, with $C_I$ being the number of channels for input image 190, I). It will be appreciated that if there are more than two segments, the number of channels will increase. I' can therefore be defined as having $C_I$+$C_S$+$C_N$ channels, where $C_S$ is one and represents the initial segmentation 180 channel, and $C_N$ is the number of geodesic distance map channels equivalent to the number of segments in the initial segmentation 180.

FIG. 4 shows a flowchart of a method as described herein for segmenting an image. The method starts at step 300 with an input image being provided. In some cases, input image may be a region of a larger image, with the user selecting the relevant region, such as by using a bounding box to denote the region of the larger image to use as the input image.

At step 310 a first segmentation of the image into multiple segments is generated using a first machine learning system. In some examples, the first machine learning system may be a convolutional neural network. At step 320 the user provides indications of (at least) image locations that have been incorrectly segmented. Each indication may correspond to a particular segment, e.g. the indication indicates that the image location(s) of the indication should belong to a particular segment.

Note that there may be multiple instances of a given segment type within the image, e.g. two eyes. In some cases, the different instances may be handled as separate segments, each with its own indications—i.e. separate indications might be provided for the left and right eyes. Alternatively, the different instances may be handled together as a single segment type, with shared indications—i.e. a single set of indications are provided for both eyes.

At step 330 individual geodesic distance maps are created for each respective segment. The geodesic distance map for a given segment contains values for each pixel representing the smallest geodesic distance from that pixel to an indication (indicated pixel location) for the respective segment. At step 340 a second segmentation is generated using a second machine learning system, which may have a generally similar structure to the first machine learning system. For example, the first and second machine learning systems may both be formed from a CNN. The second machine learning system receives as input the original input image, the first segmentation, and each of the geodesic distance maps corresponding to respective segments, which may all be combined together using channel concatenation, and then generates the refined segmentation as an output. Note that in some implementations, the second machine learning system may perform the refined segmentation without receiving the first segmentation (in which case, the second segmentation is performed anew based on the input image and each of the geodesic maps).

At step 350 the user decides whether to accept the second segmentation of the input image. If so, the method proceeds to step 360 and ends, alternatively, the user can return to step 320 to provide further indications of mis-segmented regions to provide a further refined segmentation. Accordingly, the system may potentially cycle through one or more iterations of the loop shown in FIG. 4 in order to produce a suitable segmentation. In the case of such multiple iterations, the system generally retains and accumulates the indications from previous iterations, so that these do not need to be re-entered, although there may be a facility for a user to amend or delete the previous indications if so desired.

Figure 5:
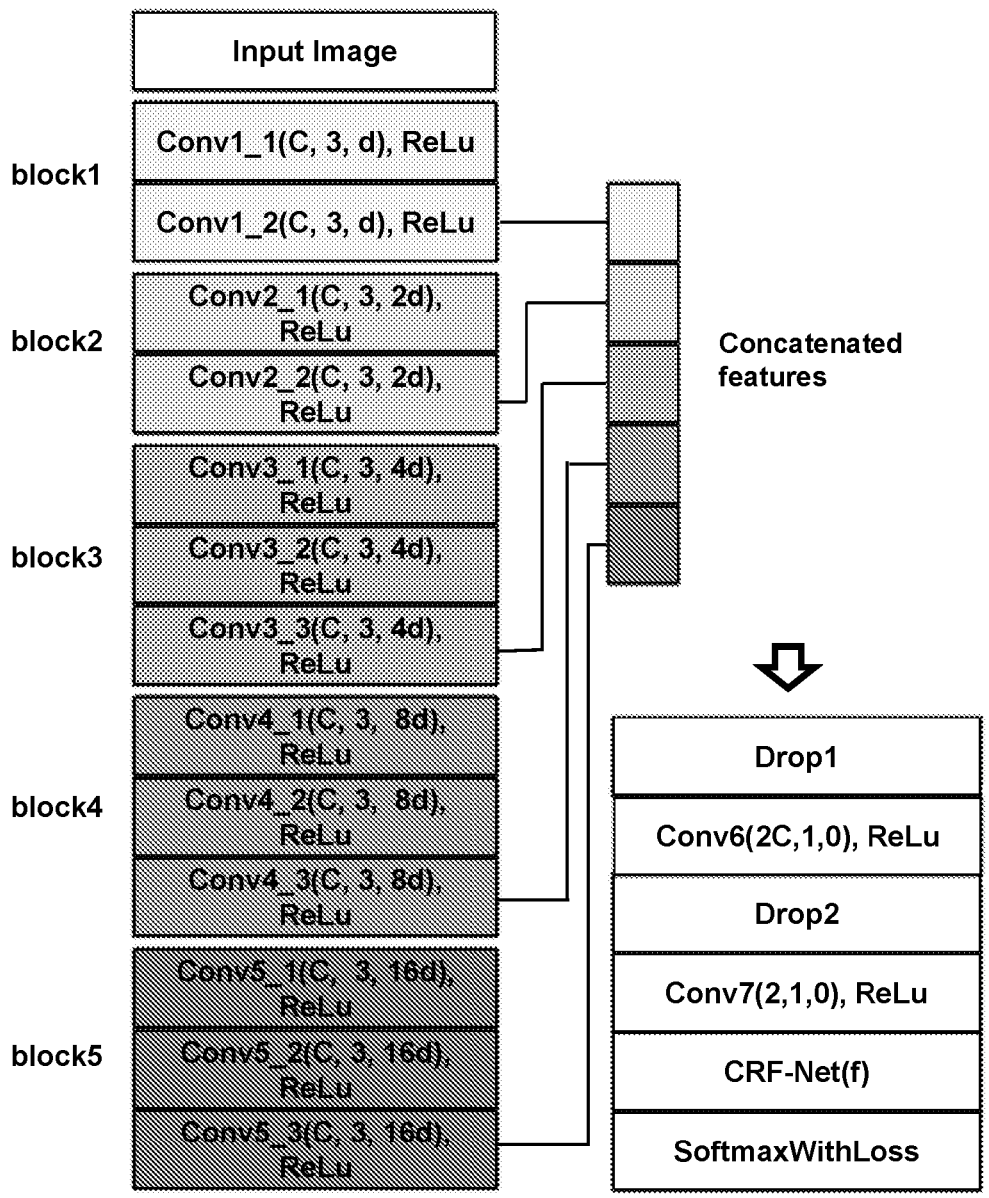
FIG. 5 shows an example structure for a first segmentation network P-Net, in accordance with the example method of FIG. 1.

FIG. 5 shows an example structure for the first segmentation network, P-Net, which is a resolution preserving CNN structure using dilated convolution and a conditional random field (CRF). The CNN structure in the example method captures high-level features from a large receptive field without loss of resolution of feature maps. To simplify the comparison with existing network structures, the CNN structure is adapted from VGG-16 [24] and it is made resolution-preserving. There are 13 convolutional layers that are grouped into five blocks. Each of the first two blocks has two convolutional layers, and each of remaining blocks has three convolutional layers. The size of convolutional kernel may be fixed (for example) as 3×3 in all these convolutional layers.

In FIG. 5, the convolution layer parameters are represented as (C, 2r+1, I), where C is the number of output channels, 2r+1 is the convolutional kernel size and/is the dilation parameter as well as the padding size. The stride of each convolutional layer is set to 1 to that the resolution is kept the same through the network.

To obtain an exponential increase of the receptive field, VGG-16 uses a max-pooling and down-sampling layer after each block, but this implementation would at the same time decrease the resolution of feature maps exponentially. Therefore, to preserve resolution through the network, we remove the max-pooling and down-sampling layers and use dilated convolution in each block.

In some implementations, the second machine learning system, R-Net, is the same as P-Net, except for the additional input channels, and the use of the user interactions (indications) in CRF-Net, as described in more detail below. However, other implementations may use a different configuration or structure for R-Net compared with P-Net.

By way of example (and without limitation), we now consider a 2D image I of size W×H, and let $K_{rq}$ be a square dilated convolutional kernel with a size of (2r+1)×(2r+1) and a dilation factor q, where r∈{0, 1, 2, ... } and q∈{0, 1, 2, ... }. The dilated convolutional output of I with $K_{rq}$ is typically defined as:

$$I_c(x,y) = \Sigma_{i=-r}^{r} \Sigma_{j=-r}^{r} I(x-qi, y-qj) K_{rq}(i+r, j+r) \quad (3)$$

(where interpolation of the kernel may also be used instead of zero filling). In the example networks shown in FIG. 5, for block 1 to block 5, we set r to 1 and the size of a convolutional kernel becomes 3×3. The dilation factor in block i is set to:

$$q_i = d \times 2^{i-1}, i=1, 2, \ldots, 5 \quad (4)$$

where d∈{0, 1, 2, ... } is a system parameter controlling the base dilation factor of the network. We set d=1 in our experiments (by way of example).

The receptive field of a dilated convolutional kernel $K_{rq}$ is (2rq+1)×(2rq+1). Let $R_i \times R_i$ denote the receptive field of block i. $R_i$ can be computed as:

$$R_i = 2(\Sigma_{j=1}^{i} L_j \times (rq_j)) + 1, i=1, 2, \ldots, 5 \quad (5)$$

where $L_j$ is the number of convolutional layers in block j, and $L_j$ is 2, 2, 3, 3, 3 for the five blocks respectively. For r=1, the width of the entire receptive field of each block is $R_1$=4d+1, $R_2$=12d+1, $R_3$=36d+1, $R_4$=84d+1, $R_5$=180d+1, respectively, so these blocks capture features at different scales.

In the example, the stride of each convolutional layer is set to 1 and the number of output channels of convolution in each block is set to a fixed number C. In order to use multi-scale features, we concatenate the features from different blocks to get a composed feature of length 5C. This feature is fed into a classifier which is implemented by two additional layers Conv6 and Conv7, as shown in FIG. 5. Conv6 and Conv7 use convolutional kernels with a size of 1×1 and dilation factor of 1, and the number of output channels for them is 2C and 2 respectively. Conv7 gives each pixel an initial score of belonging to the foreground or background class (in the case of a binary segmentation in respect of a single object or organ).

Figure 7:
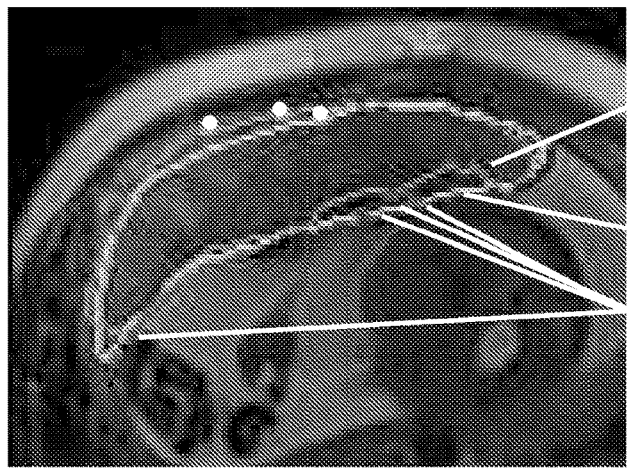
FIG. 7a and FIG. 7b show examples of simulated user interactions (indications) on training images, according to an example of the present invention.
Figure 7:
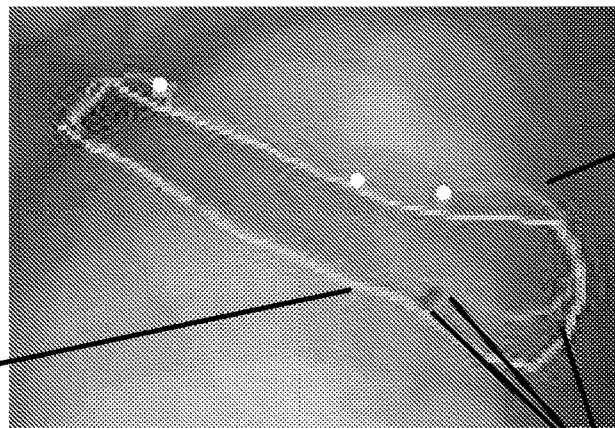

FIG. 7 shows an example structure for the first segmentation network P-Net including a CRF applied on the basis on the output from Conv7. The CRF can be advantageously implemented by a recurrent neural network (CRF-Net) which can be jointly trained with P-Net or R-Net. The CRF-Net gives a regularized prediction for each pixel, which may be fed into a logistic loss function layer.

In order to produce a more spatially consistent segmentation (and also, in the case of R-Net, to be able to add hard constraints based on the user indications), a CRF is applied to the output from Conv7. The CRF may be implemented by a recurrent neural network (CRF-Net, described in more detail below), which can be jointly trained with P-Net or R-Net (as appropriate), or may be implemented in any other form with either trained or fixed parameters. The CRF-Net gives a spatially regularized prediction for each pixel, which may be fed into a logistic loss function layer, SoftmaxWithLoss, which can be considered as a form of output normalization (see http://caffe.berkeleyvision.org/tutorial/loss.html).

In [17], a CRF based on RNN was implemented that is trainable by back-propagation. In an example implementation, this CRF is extended so that the pairwise potential can be freeform functions rather than Gaussian functions. We refer to this CRF as CRF-Net(f), or, when user interactions (indications) are added in the interactive refinement context of step 340 of FIG. 3, as CRF-Net(fu). Thus CRF-Net(f) is connected to the first machine learning system, P-Net, and CRF-Net(fu) is connected to the second machine learning system, R-Net.

Let X be the label map assigned to an image I (for example, by Conv7), as shown in FIG. 5). The CRF typically models the probability of X given I as a Gibbs distribution $$P(X = x \mid I) = \frac{1}{Z(I)} \exp(-E(x \mid I)),$$

where Z(I) is the normalization factor known as the partition function, and E(x) is the Gibbs energy:

$$E(x) = \sum_{i} \varphi_u(x_i) + \sum_{(i,j) \in N} \varphi_p(x_i, x_j) \quad (6)$$

In Equation (6), the unary potential $\varphi_u(x_i)$ measures the cost of assigning label $x_i$ to pixel i, and the pairwise potential $\varphi_p(x_i, x_j)$ is the cost of assigning labels $x_i$; $x_j$ to pixel pair i; j. N is the set of all pixel pairs. In this method, the unary potential is typically obtained from the P-Net or R-Net, which give the initial classification scores for each pixel.

The pairwise potential may classically be defined as:

$$\varphi_p(x_i, x_j) = \mu(l_i, l_j) f(\tilde{f}_{ij}, d_{ij}) \quad (7)$$

where $\tilde{f}_{ij} = f_i - f_j$, and $f_i$ and $f_j$ represent the feature vectors of pixel i and j respectively (but a different choice could be made if so desired); $d_{ij}$ is the Euclidean distance between pixel i and j; and $\mu(l_i, l_j)$ is the compatibility between the label of i and that of j. The feature vectors can either be learned by a network or derived from image features such as spatial location with intensity values (for the experiments described herein, the latter one was adopted, as also used in [3], [17], [46], for simplicity and efficiency). f(•) is a function in terms of $\tilde{f}_{ij}$ and $d_{ij}$.

Figure 6:
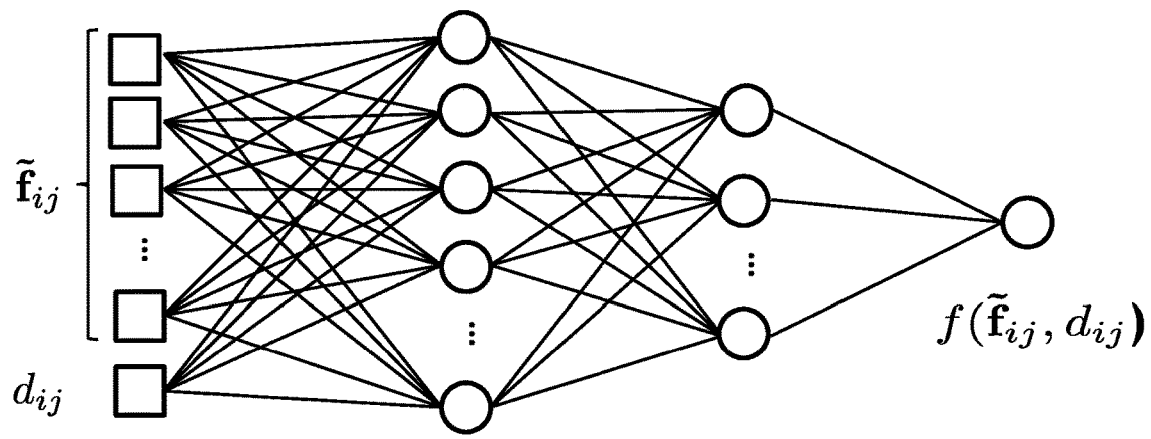
FIG. 6 shows an example network structure for a pairwise potential function, according to an example of the present invention.

Instead of defining f(•) as a single Gaussian function [3] or a combination of several Gaussian functions [17], [46], we set it as a freeform function represented by a fully connected neural network (Pairwise-Net) which can be learned during training. FIG. 6 shows an example network structure of Pairwise-Net for a pairwise potential function $f(\tilde{f}_{ij}, d_{ij})$ (as defined above). The input is a vector composed of $\tilde{f}_{ij}$ and $d_{ij}$. There are two hidden layers and one output layer that outputs a scalar number as $\varphi_p(x_i, x_j)$.

A widely used method to minimize the energy in Eq. 6 is the Graph Cuts [3], but the parameters are not optimized by back-propagation. The continuous max-flow algorithm [44]

can also be used for this purpose but its parameters are manually designed. Alternatively, mean-field approximation [17], [46], [51] is often used to efficiently minimize the energy while allowing learning parameters by back-propagation. In some examples, instead of computing P(X|I) directly, an approximate distribution $Q(X|I)=\Pi_i Q_i(x_i|I)$ is computed so that the KL-divergence $D(Q\|P)$ is minimized. This typically yields an iterative update of $Q_i(x_i|I)$ [17], [46], [51].

$$Q_i(x_i \mid I) = \frac{1}{Z_i} e^{-E(x_i)} = \frac{1}{Z_i} e^{-\varphi_u(x_i) - \phi_p(x_i)} \tag{8}$$

$$\phi_p(x_i = l \mid I) = \sum_{l' \in \mathcal{L}} \mu(l, l') \sum_{j \neq i} f(\tilde{f}_{i,j}, d_{ij}) Q_j(l' \mid I) \tag{9}$$

where $\mathcal{L}$ is the label set, and i and j are a pixel pair (i.e. (i, j)∈N.

For the proposed CRF-Net(fu), with the set of user-provided scribbles $S_{fb}=S_f \cup S_b$, we can choose to force the probability of pixels in the scribble set to be 1 or 0. The following equation is then advantageously used as the update rule for each iteration:

$$Q_i(x_i \mid I) = \begin{cases} 1 & \text{if } i \in S_{fb} \text{ and } x_i \neq s_i \\ 0 & \text{if } i \in S_{fb} \text{ and } x_i \neq s_i \\ \frac{1}{Z_i} e^{-E(x_i)} & \text{otherwise} \end{cases} \tag{10}$$

where $s_i$ denotes the user-provided label of a pixel i that is in the scribble set $S_{fb}$. We may follow the implementation in [17] to update Q through a multi-stage mean-field method in an RNN. Each mean-field layer splits Equation 8 into four steps including message passing, compatibility transform, adding unary potentials and normalizing [17].

In an example implementation, the computation of geodesic distances, as described above, follows the raster-scan algorithm proposed in [6] which is fast due to accessing the image memory in contiguous blocks. This method calculates the geodesic distance by applying a forward pass scanning and a backward pass scanning with a 3×3 kernel. For CRF-Net with freeform pairwise potential, two observations motivate the use of pixel connections based on local patches instead of full connections within the entire image.

First, the permutohedral lattice implementation [17], [46] allows efficient computation of a fully connected CRF only when the pairwise potentials are Gaussian functions. However, relaxing the pairwise potentials to be freeform functions, such as for the network structure shown in FIG. 6, precludes the use of the permutohedral lattice implementation, and so would be inefficient for a fully connected CRF. For example, an image with size M×N, a fully connected CRF has MN(MN−1) pixel pairs; for a small image with M=N=100, the number of pixel pairs would be almost $10^8$, which requires not only a large amount of memory but also long computational time. Second, though long-distance dependency has been shown to improve segmentation in general RGB images [12], [17], [46], this would be very challenging for medical images since the contrast between the target and background is often low. In such cases, long distance dependency may lead the label of a target pixel to be corrupted by the large number of background pixels with a similar appearance. As a result, to maintain a good efficiency and avoid long-distance corruptions, the pairwise connections for one pixel may be defined within a local patch centred on that pixel. For example, the patch size has been set to 7×7 in some implementations based on experience.

As described above, a fully connected neural network (Pairwise-Net) with two hidden layers is used to learn the freeform pairwise potential function (see FIG. 6). In some implementations, the first and second hidden layers have 32 and 16 neurons respectively and the system is implemented using an equivalent fully convolutional neural network.

A pre-training step is used to initialize the Pairwise-Net with an approximation of a contrast sensitive function as described in the following:

$$f_0(\tilde{f}_{i,j}, d_{ij}) = \exp\left(-\frac{\|\tilde{f}_{ij}\|^2}{2\sigma^2 \cdot F}\right) \cdot \frac{\omega}{d_{i,j}} \tag{11}$$

where F is the dimension of feature vectors $f_i$ and $f_j$, and $\omega$ and $\sigma$ are two parameters controlling the magnitude and shape of the initial pairwise function respectively. For example, the value of $\sigma$ may be set as 0.08 and the value of $\omega$ may be set as 0.5 based on experience (but other systems may use different values as appropriate). Similar to [16], [17], [46], $f_i$ and $f_j$ are set as values in input channels (i.e., image intensity in our case) of P-Net for simplicity as well as for obtaining contrast-sensitive pairwise potentials.

To pre-train Pairwise-Net, a training set T'={X',Y'} of 100 k samples was generated, where X' is the set of features simulating the concatenated $\tilde{f}_{ij}$ and $d_{ij}$, and Y' is the set of prediction values simulating $f_0$ ($\tilde{f}_{ij}, d_{ij}$). For each sample s in T', the feature vector $x'_s$ has a dimension of F+1 where the first F dimensions represent the value of $\tilde{f}_{i,j}$ and the last dimension denotes $d_{ij}$. The c-th channel of $x'_s$ is filled (for example) with a random number k', where k'~Norm(0, 2) for c≤F and k'~U(0,8) for c=F+1. The ground truth of the predicted value $y'_s$ for $x'_s$ was obtained by Equation 11 above. After generating X' and Y', an optimisation algorithm, such as Stochastic Gradient Descent (SGD) with a quadratic loss function, may be used to pre-train the Pairwise-Net.

Various pre-processing steps may be used as appropriate. For example, the image data may be normalized by the mean value and standard variation of the training images. In addition, data augmentation may be used, such as by vertical or horizontal flipping, random rotation with angle range [−π/8,π/8], and/or random zoom with scaling factor range [0.8, 1.25]. The logistic loss function and SGD algorithm may be used for optimization. The mini-batch size was set to 1, the momentum to 0.99, and the weight decay to $5 \times 10^{-4}$ (but any appropriate values or policies may be used). Likewise, in a particular implementation, the learning rate may be halved every 5 k iterations (but again other values or policies can be used).

Since a proper initialization of the P-Net and CRF-Net(f) is helpful for a faster convergence of the joint training between them, the P-Net with CRF-Net(f) were trained in three steps. Firstly, the P-Net was pre-trained with initial learning rate $10^{-3}$ and maximal number of iterations 100 k; secondly, for CRF-Net(f), the Pairwise-Net was pre-trained as described above; and thirdly, P-Net and CRF-Net(f) were jointly trained with initial learning rate $10^{-6}$ and maximal number of iterations 50 k (but again other values or policies can be used).

After training of the P-Net with CRF-Net(f), user interactions were automatically simulated to train R-Net with CRF-Net(fu) (manual training could also be used instead of or in conjunction with the automatic training). First P-Net with CRF-Net(f) was used to obtain an automatic segmentation for each training image, which was compared with the ground truth to find mis-segmented regions. Then the user interactions on each mis-segmented region were simulated by randomly sampling $N_c$ pixels in that region. Supposing, in one example, the size of one connected under-segmented or over-segmented region is $N_m$, we set $N_c$ for that region to 0 if $N_m<30$ and $[N_m/100]$ otherwise (based on experience).

FIG. 7a and FIG. 7b show examples of simulated user interactions (indications) on training images, in particular, FIG. 7a shows a placenta and FIG. 7b shows a clavicle. In these Figures, green represents the automatic segmentation given by P-Net with CRF-Net(f), yellow represents the ground true segmentation, red represents simulation indications (clicks) representing under-segmentation, and cyan represents simulation indications (clicks) representing over-segmentation. Note that under-segmentation is where the foreground segmentation incorrectly excludes the desired object, and over-segmentation is where the foreground segmentation incorrectly includes the background. Hence the red indications in effect denote regions that below to the foreground object, while the cyan indications in effect denote regions that below to the background (i.e. the same colour scheme as used for FIG. 2). With these simulated user interactions on the initial segmentation of training data, the R-Net with CRF-Net(fu) may be subsequently trained via the same three steps as used by P-Net with CRF-Net(f).

In one example, the P-Net and R-Net with CRF-Net described above were implemented using the Caffe deep learning library (see http://caffe.berkeleyvision.org/). The training process was performed via two 8-core E5-2623v3 Intel Haswells and two K80 NVIDIA GPUs and 128 GB memory. The testing process with user interactions was performed on a MacBook Pro (OS X 10.9.5) with 16 GB RAM and an Intel Core i7 CPU running at 2.5 GHz and an NVIDIA GeForce GT 750M GPU. A Matlab graphical user interface (GUI) was developed for user interactions (see https://www.mathworks.com/products/matlab.html). It will be appreciated that these computing platforms are provided merely by way of example, and any other appropriate systems could be used instead.

To evaluate the performance of the approach described herein, an example implementation of P-Net was compared with FCN [11] and DeepLab [16]. Pre-trained models of FCN and DeepLab based on ImageNet were fine-tuned for the segmentation tasks. These two networks are extensions from VGG-16 [24] so that they allow obtaining the label of an image through one single forward pass. However, the output resolution of these two networks is ⅛ of the input resolution; therefore their output was up-sampled to obtain the final result. For fine-tuning, the same learning rate schedules as those used for training P-Net were used, with the maximal number of iterations again being set to 100 k. Since the input of FCN and DeepLab should have three channels, we created two additional copies of the grey-level input images and composed them into a 3-channel image as the input. The example P-Net was also compared with its variation P-Net(b5) that only uses features from block 5 (FIG. 5) instead of concatenated multi-scale features (of blocks Conv6 and Conv7).

CRF-Net(f) was compared with two counterparts:
1) CRF-Post which uses a CRF as an independent post-processing step for the output of P-Net. We followed the implementation presented in [46, 16]; instead of learning by back-propagation, the parameters of this CRF were manually tuned based on a coarse-to-fine search scheme as suggested by [16].
2), CRF-Net(g) which refers to the CRF proposed in [17] that can be trained jointly with CNNs by using Gaussian functions as pairwise potentials.

To evaluate the user interaction efficiency of the approach described herein, an example implementation (referred to as DeepIGeoS) was compared with four other interactive segmentation methods:
1) GeoS [6] that computes a probability based on the geodesic distance from user-provided scribbles for pixel classification;
2) Graph Cuts [3] that models segmentation as a min-cut problem based on user interactions;
3) Random Walks [5] that assigns a pixel with a label based on the probability that a random walker reaches a foreground seed first;
4) SlicSeg [8] that uses Online Random Forests to learn from scribbles and predict remaining pixels.

Two users (an Obstetrician and a Radiologist) used these segmentation methods to segment every test image until a visually acceptable result had been achieved.

For quantitative evaluation, we measured the Dice score and the average symmetric surface distance (ASSD) (it will be appreciated that these are two standard measures for evaluation, but various others are available and could be used as well or instead of these):

$$\text{Dice} = \frac{2|Ra \cap Rb|}{|Ra| + |Rb|} \qquad (12)$$

where $R_a$ and $R_b$ represent the region segmented by the algorithms and the ground truth, respectively.

$$ASSD = \frac{1}{|S_a| + |S_b|} \left( \sum_{i \in S_a} d(i, s_b) + \sum_{i \in S_b} d(i, S_a) \right) \qquad (13)$$

where $S_a$ and $S_b$ represent the set of surface points of the target segmented by algorithms and the ground truth respectively; and $d(i; S_b)$ is the shortest Euclidean distance between i and $S_b$. The Student's t-test was used to compute the p-value in order to see whether the results of two algorithms were significantly different from one another.

Two main sets of testing were performed, the first relating to the segmentation of the placenta from fetal magnetic resonance imaging (MRI), the second relating to segmentation of the clavicle from radiographs. Fetal MRI is an emerging diagnostic tool complementary to ultrasound due to its large field of view and good soft tissue contrast. Segmenting the placenta from fetal MRI is important for fetal surgical planning, e.g., in the case of twin-to-twin transfusion syndrome [57]. Clinical fetal MRI data are often acquired with a large slice thickness for good contrast-to-noise ratio. Movement of the fetus can lead to inhomogeneous appearances between slices. In addition, the location and orientation of the placenta vary largely between individuals. These factors make automatic and 3D segmentation of the placenta a challenging task [58]. Interactive 2D slice-based segmentation is expected to achieve more robust results [8, 59]. The 2D segmentation results can also be used for motion correction and high-resolution volume reconstruction [60].

We collected clinical MRI scans for 25 pregnancies in the second trimester. The data were acquired in axial view with a pixel size between 0.7422 mm×0.7422 mm and 1.582 mm×1.582 mm and slice thickness 3-4 mm. Each slice was resampled with a uniform pixel size of 1 mm×1 mm and cropped by a box of size 172×128 containing the placenta. From this data set, 17 volumes with 624 slices were used for training, three volumes with 122 slices were used for validation and five volumes with 179 slices were used for testing. The ground truth was manually delineated by two experienced Radiologists.

Figure 8:
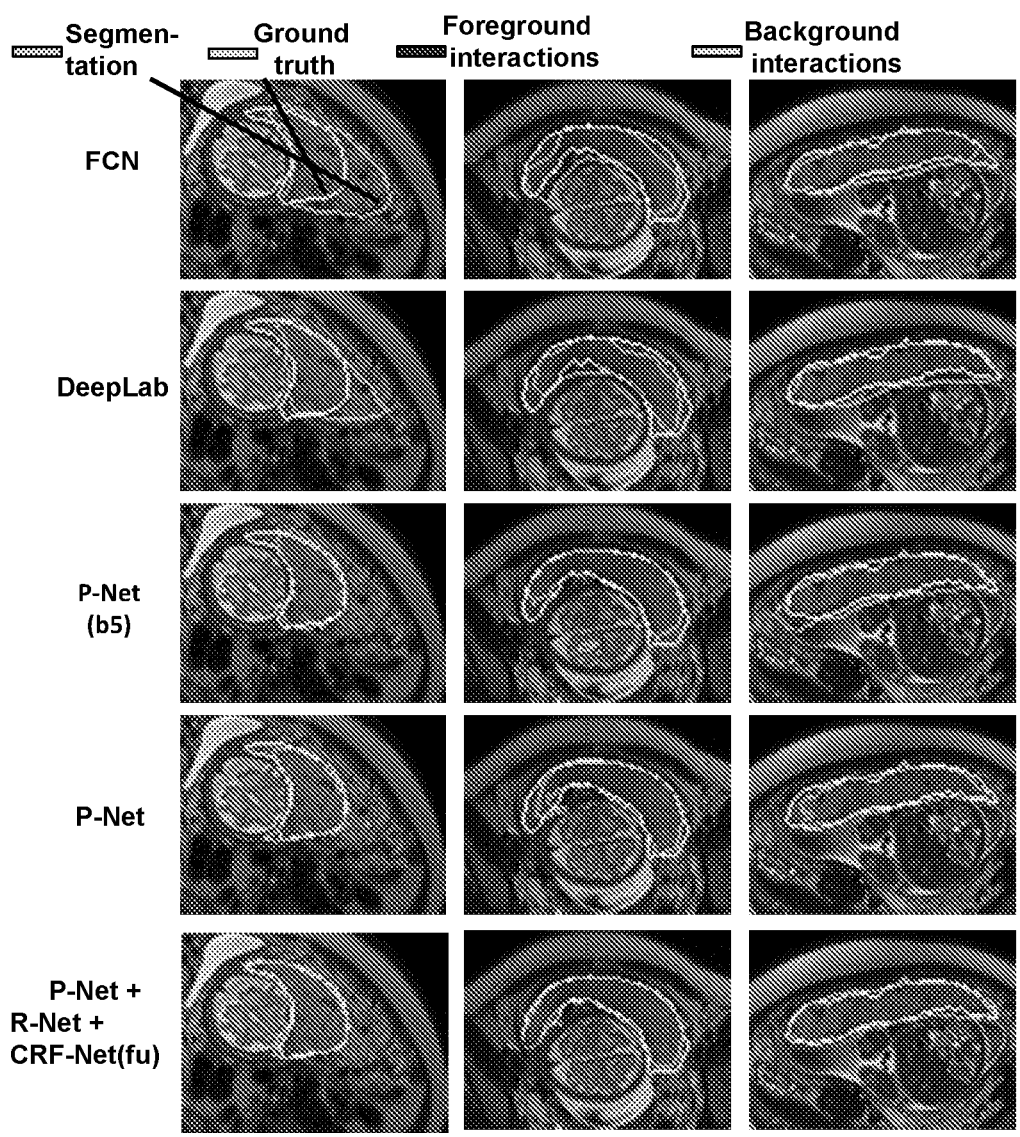
FIG. 8 shows a comparison of automatic segmentation results for the placenta obtained using different network structures.

FIG. 8 shows the automatic segmentation results obtained using different network structures. In particular, each row in FIG. 8 corresponds to a different segmentation system (or stage), while each column corresponds to a different image (or different image slice). The first four rows of FIG. 8 correspond to an initial automatic segmentation (corresponding to the output of step 120 in FIG. 1), while the final (bottom) row of FIG. 8 shows the refined segmentation, benefiting from user interactions, following the approach described herein (and corresponding to the output of step 160 in FIG. 1).

Superimposed on the images of FIG. 8 are:
a) a green line showing the results of the automatic segmentation (including with user interactions for the final row of FIG. 8),
b) a yellow line showing the ground truth,
c) red indications representing foreground interactions, i.e. identifying image locations corresponding to the foreground segment, and
d) cyan indications representing background interactions, i.e. identifying image locations corresponding to the background.

In general, it can be seen from FIG. 8 that FCN is able to capture the main region of the placenta, but the segmented regions are blob-like with smooth boundaries. DeepLab is better than FCN, but its blob-like results are similar to those of FCN. These results are mainly due to the down-sampling and up-sampling procedure employed by these FCN and DeepLab. In contrast, P-Net(b5) and P-Net obtain more detailed results with less smooth boundaries. Overall, it can be observed that P-Net achieves better results than the other three networks, but even for P-Net some mis-segmented regions are still readily apparent.

Table 1 provides a quantitative comparison of placenta segmentation using different networks and CRFs. CRF-Net (g) [17] constrains pairwise potential as Gaussian functions. CRF-Net(f) is the CRF described herein that learns freeform pairwise potential functions. A significant improvement for P-Net (p-value<0.05) is shown in bold font. P-Net achieves a higher Dice score of 84.78±11.74% and a lower ASSD of 2.09±1.53 pixels, and therefore performs better, compared with the other three network structures. In addition, it can be seen that P-Net provides improvements over P-Net(b5).

TABLE 1

| Method | Dice (%) | ASSD (pixels) |
|---|---|---|
| FCN | 81.47 ± 11.40 | 2.66 ± 1.39 |
| DeepLab | 83.38 ± 9.53 | 2.20 ± 0.84 |
| P-Net(b5) | 83.16 ± 13.01 | 2.36 ± 1.66 |
| P-Net | 84.78 ± 11.74 | 2.09 ± 1.53 |

TABLE 1-continued

| Method | Dice (%) | ASSD (pixels) |
|---|---|---|
| P-Net + CRF-Post | 84.90 ± 12.05 | 2.05 ± 1.59 |
| P-Net + CRF-Net(g) | 85.44 ± 12.50 | 1.98 ± 1.46 |
| P-Net + CRF-Net(f) | 85.86 ± 11.67 | 1.85 ± 1.30 |

Figure 9:
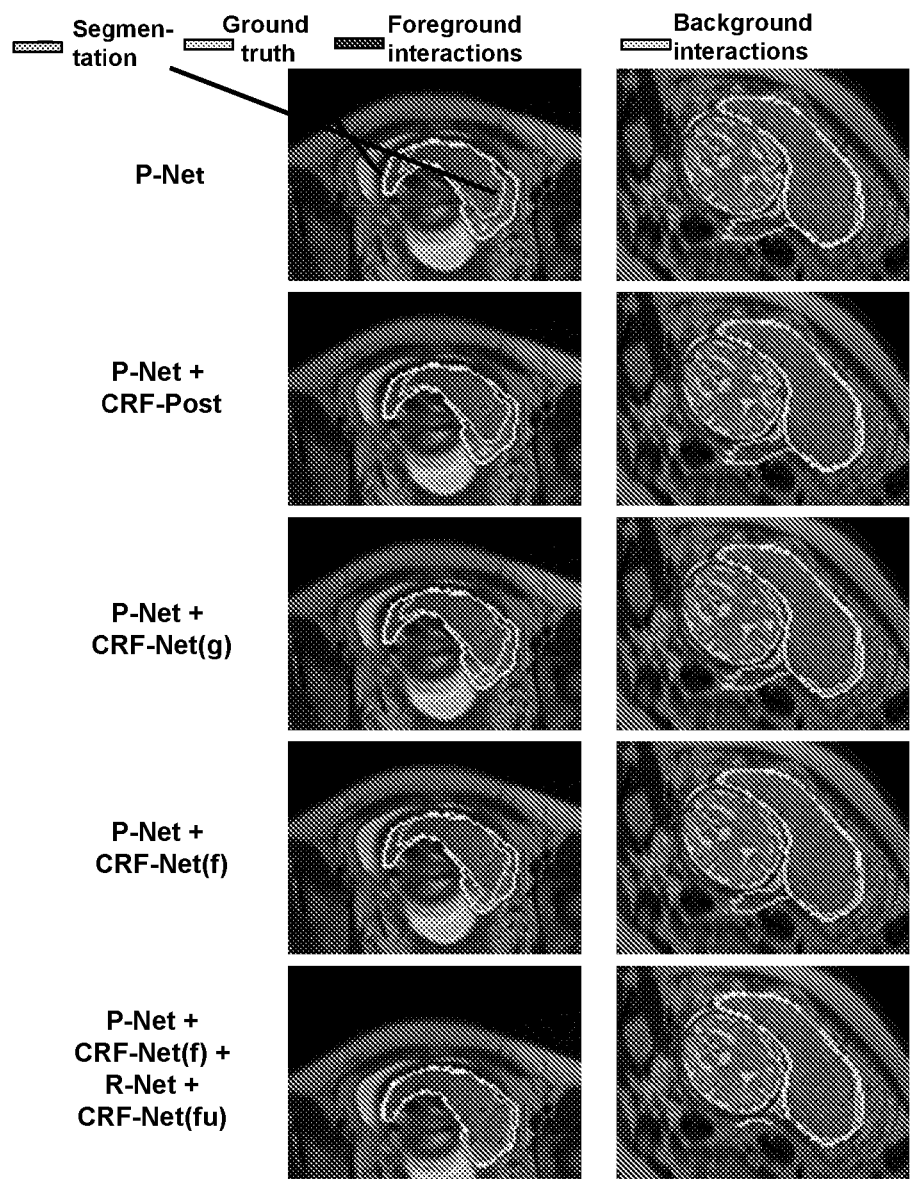
FIG. 9 shows a comparison of segmentation results for the placenta obtained using CRF-Post, CRF-Net(g) and CRF-Net(f).

Based on P-Net, the performance of different CRFs was investigated. FIG. 9 shows a visual comparison of segmentation results obtained by CRF-Post, CRF-Net(g) and CRF-Net(f) (in conjunction with P-Net). As for FIG. 8, each row in FIG. 9 corresponds to a different segmentation system, with the final (bottom) row of FIG. 9 showing the refined segmentation benefiting from user interactions, and each column of FIG. 9 corresponds to a different image (or different image slice). The coloured markings (green, yellow, red and cyan) are utilised in the same manner as set out above for FIG. 8, i.e. green is the machine segmentation, yellow is ground truth, red is foreground, cyan is background.

It can be seen from the first column that the placenta is under-segmented by P-Net (i.e. the green segmentation generally lies within the yellow ground truth). CRF-Post leads to very small improvements on the result, while CRF-Net(g) and CRF-Net(f) improve the result by preserving more placenta regions, the latter generally showing the better segmentation. In the second column, P-Net obtains an over-segmentation of adjacent fetal brain and maternal tissues. CRF-Post does not improve this (over)segmentation noticeably, but CRF-Net(g) and CRF-Net(f) remove some of the over-segmented areas. Overall, CRF-Net(f) shows a better performance than the other two CRFs.

A quantitative evaluation of these three CRFs is also presented in Table 1, which shows CRF-Post leads to a result that is very close to that of P-Net (p-value>0.05), while the last two CRFs significantly improve the segmentation (p-value<0.05). In addition, CRF-Net(f) is better than CRF-Net(g). However, although using CRF-Net(f) leads to better segmentation, both FIG. 9 and Table 1 indicate that significant mis-segmentation remains in some images.

Figure 10:
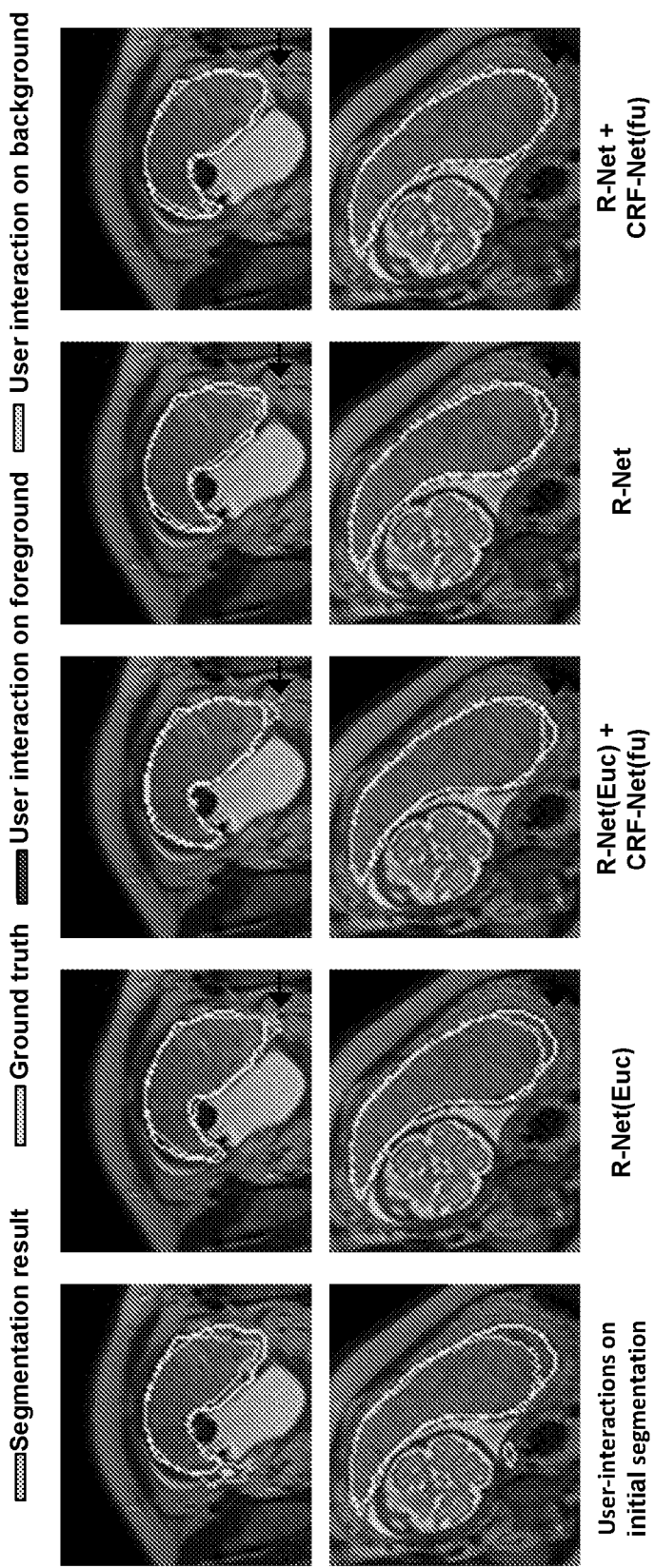
FIG. 10 shows a comparison of segmentation results for the placenta obtained via an interactive refinement using R-Net and certain variations thereof.

Accordingly, the segmentation was interactively refined by obtaining user indications, which were then provided to R-Net with CRF-Net(fu) to refine the segmentations. FIG. 10 shows examples of interactive refinement using R-Net with CRF-Net(fu) (using the same colour coding for lines as set out above for FIGS. 8 and 9). Each row of FIG. 10 corresponds to a different image (or different image slice) of the placenta. The first column in FIG. 10 shows initial segmentation results obtained by P-Net+CRF-Net(f), superimposed with user indications to indicate the foreground (red) or the background (cyan). The second to fifth columns in FIG. 10 show the results for four variations of refinement, based on R-Net using a geodesic or Euclidean distance transform, and with or without CRF-Net(fu). These four variations correct most of the mis-segmented areas, but perform at different levels in dealing with local details, as high-lighted by the by white arrows. FIG. 10 shows that using a geodesic distance performs better than using a Euclidean distance, and both of them achieve higher accuracy by working with CRF-Net(fu) (than without).

For a quantitative comparison, we measured the segmentation accuracy after the first iteration of user refinement (giving user interactions to mark all the main mis-segmented regions and applying R-Net once). The same initial segmentation and the same set of user interactions were used for the four variations of refinement (the input is from the segmentation obtained by P-Net+CRF-Net(f)).

Table 2 presents a quantitative evaluation of placenta segmentation by R-Net with CRF-Net(fu) after the first iteration of refinement in comparison with the same four variations shown in FIG. 10 (in which R-Net(Euc) uses Euclidean distance instead of geodesic distance). The use of R-Net with CRF-Net(fu) provides a significant improvement with respect to the use of R-Net alone (p-value<0.05), as indicated in Table 2 by the bold font. In particular, the combination of R-Net using geodesic distance and CRF-Net(fu) as described herein leads to more accurate segmentation (higher Dice score and lower ASSD) than other variations presented with the same set of user interactions. The Dice score and ASSD of R-Net+CRF-Net(fu) are 89.31±5.33% and 1.22±0.55 pixels, respectively.

TABLE 2

| Method | Dice (%) | ASSD (pixels) |
| --- | --- | --- |
| P-Net + CRF-Net(f) | 85.86 ± 11.67 | 1.85 ± 1.30 |
| R-Net(Euc) | 88.26 ± 10.61 | 1.54 ± 1.18 |
| R-Net | 88.76 ± 5.56 | 1.31 ± 0.60 |
| R-Net(Euc) + CRF-Net(fu) | 88.71 ± 8.42 | 1.26 ± 0.59 |
| R-Net + CRF-Net(fu) | 89.31 ± 5.33 | 1.22 ± 0.55 |

Figure 11:
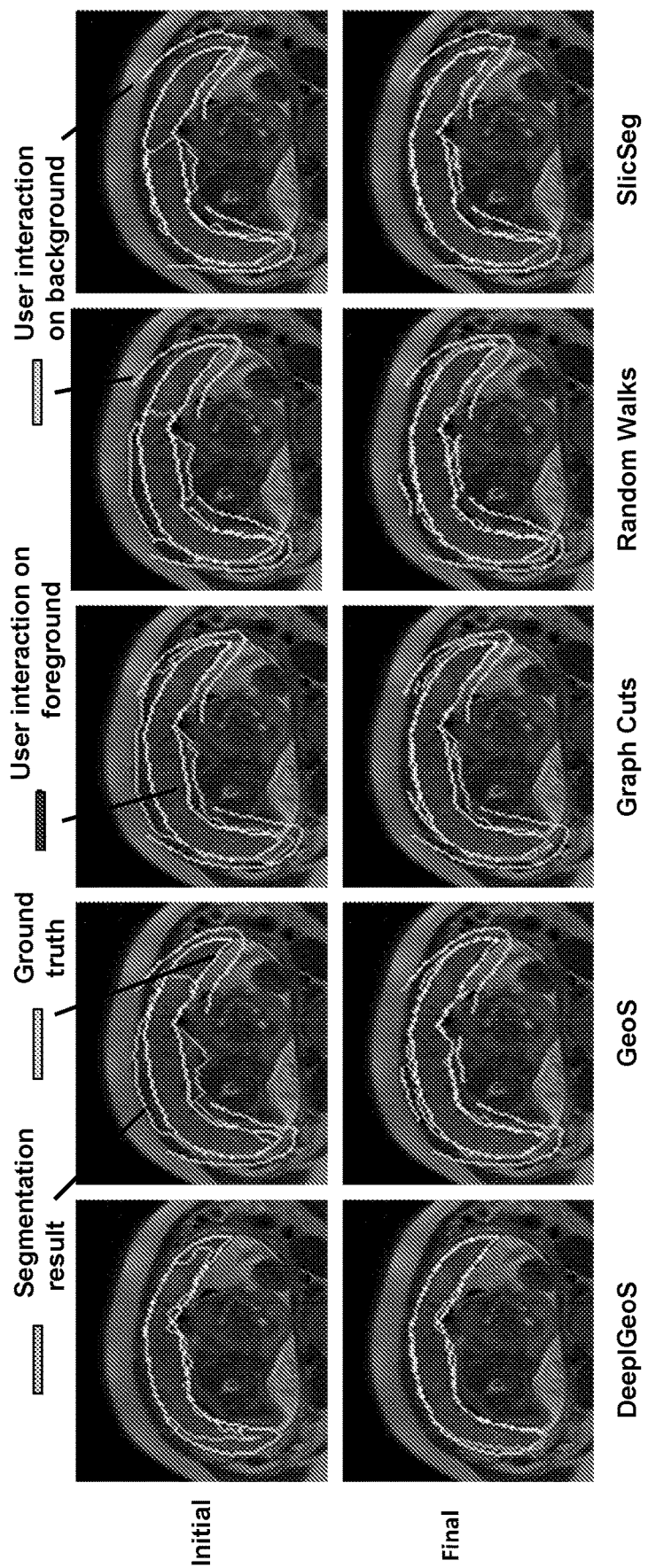
FIG. 11 shows a comparison of segmentation results for the placenta obtained by using DeeplGeoS (as described herein) and GeoS, Graph Cuts, Random Walks and SlicSeg.

FIG. 11 shows a visual comparison between DeepIGeoS and GeoS [6], Graph Cuts [3], Random Walks [5] and SlicSeg [8] for placenta segmentation. (The colour marking corresponds to that used in FIGS. 7-10). The first (top) row shows the initial scribbles and the resulting segmentation (N.B., no initial scribbles are needed for DeepIGeoS). The second (lower) row shows the final results after the refinement. It can be seen that DeepIGeoS was only provided with two short strokes (scribbles), shown in red, one at either end of the segment, to get an accurate segmentation. In contrast, the other methods require more scribbles (indications) to get similar results. It will be appreciated that this reduction in the number (and size) of user interactions helps to improve the efficiency of the overall segmentation (especially in respect of the amount of time needed from clinicians).

Figure 12:
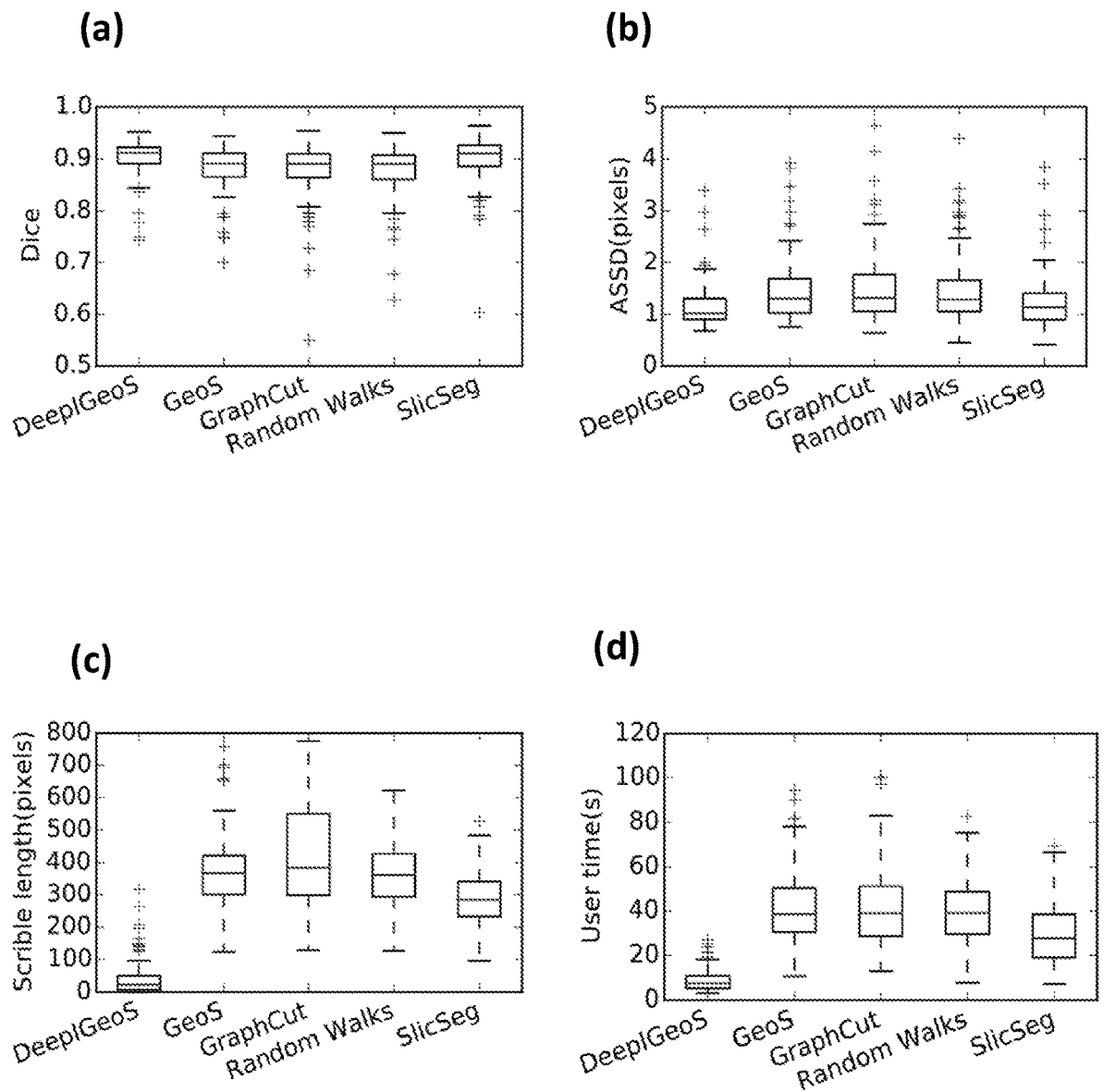
FIG. 12 shows a quantitative comparison of the methods of FIG. 11.

FIG. 12 provides a quantitative comparison of the segmentation methods shown in FIG. 11 in relation to a final segmentation of the placenta given by two users, each using the specified segmentation method. In particular, the different methods are compared based on Dice score (FIG. 12a), ASSD (FIG. 12b), total interaction (scribble length) (FIG. 12c) and user's time (FIG. 12d). From FIGS. 12a and 12b, it can be seen that the approach described herein, DeepIGeoS, achieves a similar accuracy to the other interactive methods. However, FIG. 12c shows that DeepIGeoS requires far less input from the user, i.e. the number of pixels indicated in the scribbles can be in the 10s rather than 100s. In other words, the user of the approach described herein is generally able to use smaller, and fewer, indications. As a consequence, it can be seen from FIG. 12d that the time taken by the user for DeepIGeoSis is substantially reduced in comparison to the time taken for the other methods, and hence user efficiency is correspondingly increased.

The second set of testing performed related to segmentation of the clavicle from radiographs. Chest radiographs are widely used for the detection and diagnosis of lung diseases such as lung cancer. Some findings on chest radiographs such as sharply circumscribed nodules or masses can indicate the presence of lung cancer. However, due to superposition of multiple structures including the ribs and clavicles, lung nodule detection and analysis is challenging. Segmenting the bone structures from chest radiographs can help to digitally suppress bones and thus increase the visibility of nodules [61]. In particular, clavicle suppression might aid radiologists in detecting pathologies in the lung apex for certain lung diseases such as tuberculosis. Thus, accurate clavicle segmentation is needed to help improve pathology detection, but this is hindered by low contrast and inhomogeneous appearance in the clavicle region resulting from the superimposition of several structures. In [62], it was shown that segmenting the clavicle is more difficult than segmenting the heart and the lungs. In [63], pixel classification was combined with an active shape model for automatic clavicle segmentation, although the result showed large mis-segmented areas in some images.

The publicly available JSRT database (see http://www.jsrt.or.jp/jsrt-db/eng.php) was used for testing segmentation of the clavicle. This database consists of 247 radiographs with image resolution 2048×2048 and pixel size 0.175 mm×0.175 mm. Ground truth of 93 images was given by the SCR database (http://www.isi.uu.nl/Research/Databases/SCR/) based on manual segmentation by an expert. The ground truth delineated the part of clavicle projected over the lungs and mediastinum.

For the present testing, data in the SCR database was split into two groups with 47 and 46 images respectively. For the first group, 40 images were used as training data and the other 7 images were used as validation data. All the images in the second group were used as testing data. Each original image was down-sampled into a size of 512×512 pixels and manually cropped with two 200×160 boxes covering the left and right clavicle respectively.

Figure 13:
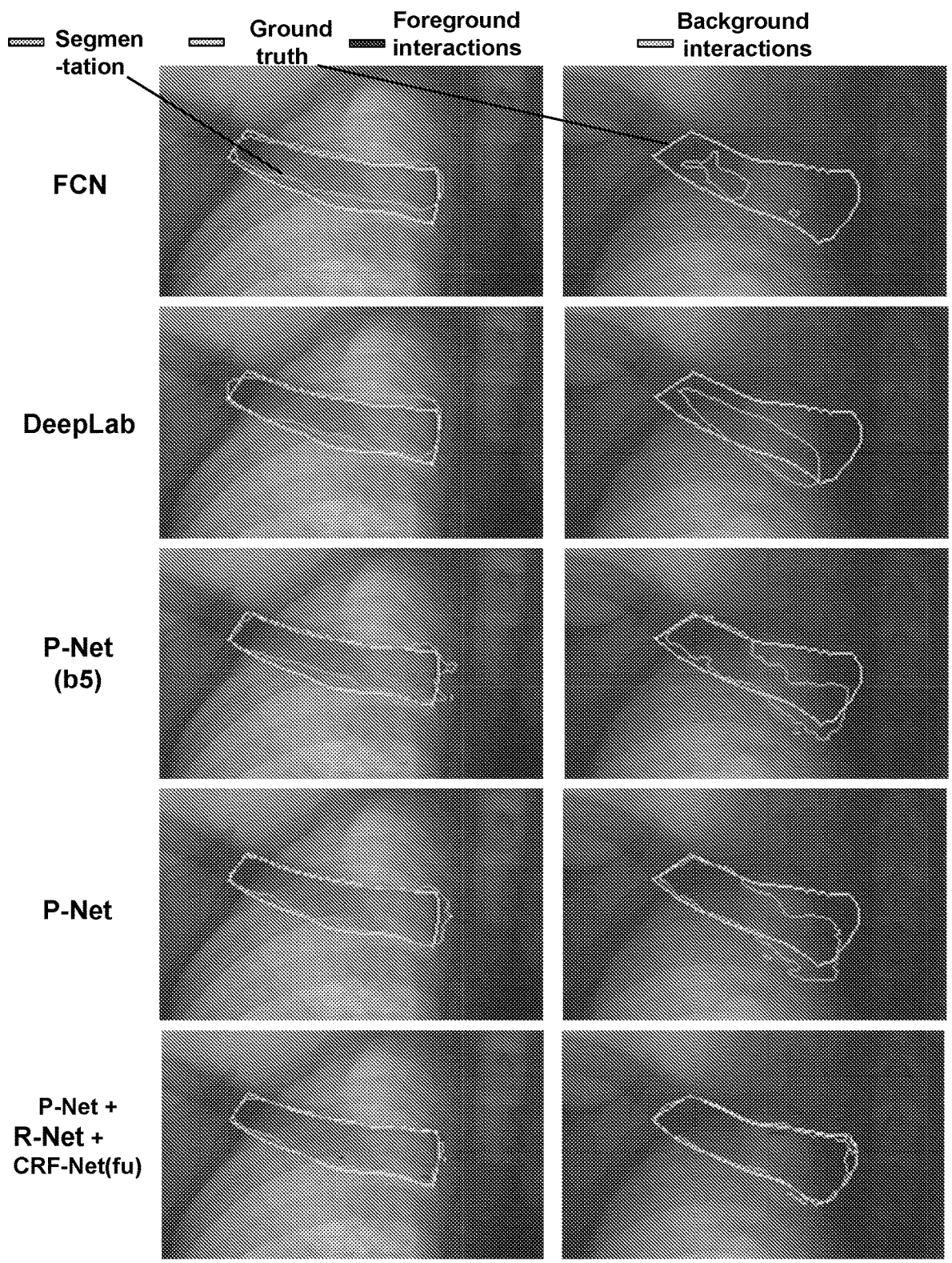
FIG. 13 shows a comparison of automatic segmentation of the clavicle by P-Net, FCN, DeepLab and P-Net(b5).

FIG. 13 shows examples of automatic segmentation of the clavicle by P-Net, which is compared with FCN, DeepLab and P-Net(b5). As for FIG. 8 and other such segmentation examples, each row in FIG. 13 corresponds to a different segmentation system, with the final (bottom) row of FIG. 13 showing the refined segmentation benefiting from user interactions, and each column of FIG. 13 corresponds to a different image (or different image slice). Likewise, the coloured markings (green, yellow, red and cyan) of FIG. 13 are utilised in the same manner as set out above for FIG. 8, i.e. green is the machine segmentation, yellow is ground truth, red is foreground, cyan is background.

For the first image (left-hand column), FCN segments the clavicle roughly, with some missed regions near the boundary, while DeepLab reduces the missed regions but leads to some over-segmentation. P-Net(b5) obtains a somewhat similar result to that of DeepLab. In contrast, P-Net achieves a more accurate segmentation, closer to the ground truth. In the second case, FCN only captures a small region of the clavicle, while DeepLab captures a larger region with both under-segmentation and over-segmentation. P-Net(b5) and P-Net both obtain better results than FCN and DeepLab.

Table 3 presents a quantitative comparison of clavicle segmentation using these four networks, and also using different CRFs (as described below). The comparison is based on Dice score and ASSD as defined above. A significant improvement from P-Net (p-value<0.05) is shown in bold font. It can be seen from Table 3 that FCN shows the worst performance, while P-Net achieves the most accurate segmentation compared with other three networks of FIG. 13, achieving 84.18±10.94% in terms of Dice and 2.79±1.78 pixels in terms of ASSD.

TABLE 3

| Method | Dice (%) | ASSD (pixels) |
| --- | --- | --- |
| FCN | 81.08 ± 13.73 | 3.38 ± 2.31 |
| DeepLab | 82.27 ± 10.80 | 3.09 ± 1.47 |
| P-Net(b5) | 82.15 ± 11.08 | 3.21 ± 1.91 |
| P-Net | 84.18 ± 10.94 | 2.79 ± 1.78 |
| P-Net + CRF-Post | 83.52 ± 11.69 | 2.84 ± 1.86 |
| P-Net + CRF-Net(g) | 84.51 ± 10.45 | 2.72 ± 1.57 |
| P-Net + CRF-Net(t) | 84.83 ± 10.52 | 2.65 ± 1.52 |

Figure 14:
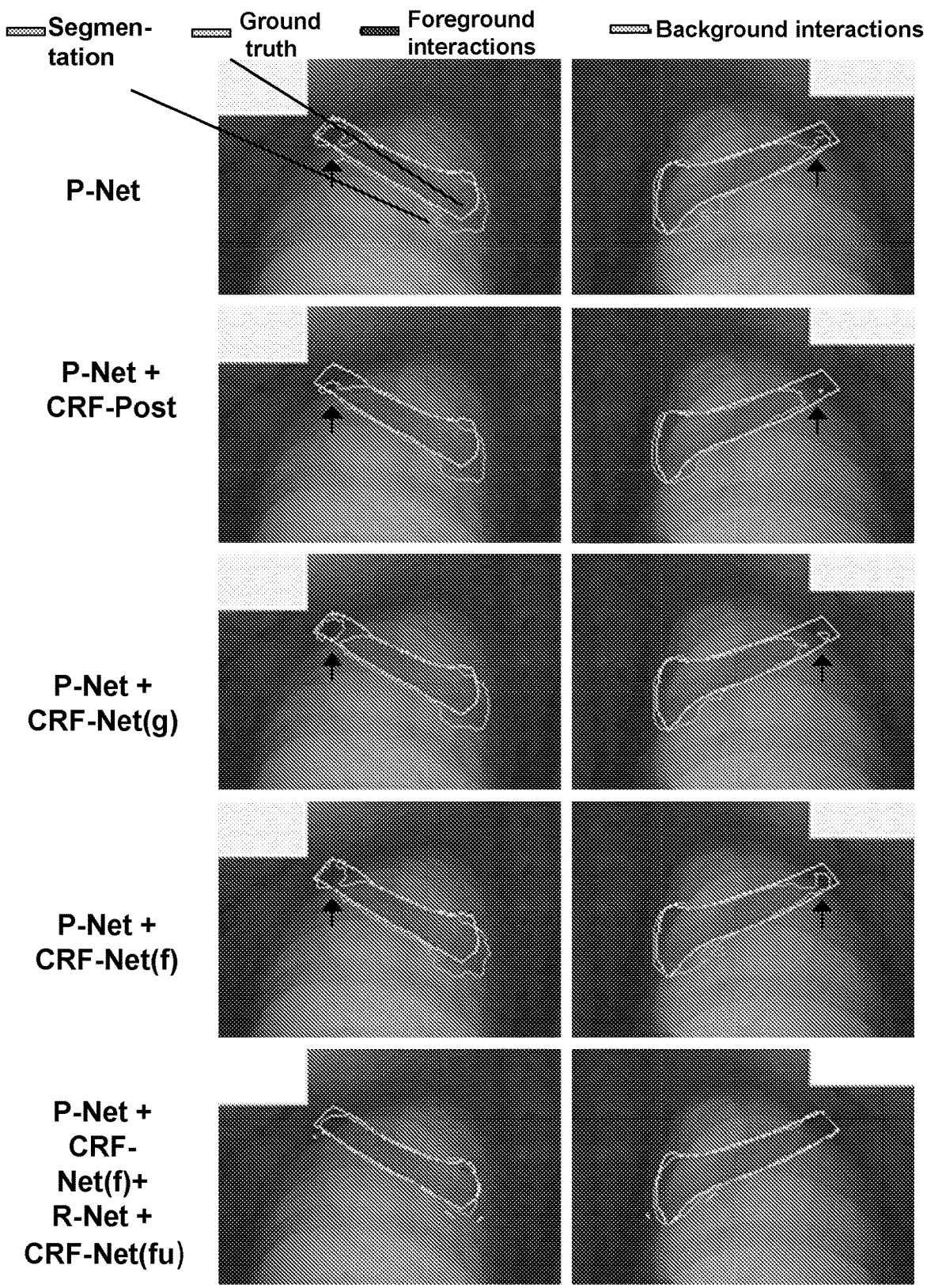
FIG. 14 shows a comparison of automatic segmentation of the clavicle using different types of CRFs.

FIG. 14 shows the effect of different types of CRFs working with an example P-Net. Again, each row in FIG. 14 corresponds to a different segmentation system, with the top row of FIG. 14 corresponding to P-Net, the middle three rows corresponding to P-Net with a specific CRF (as indicated), and the final (bottom) row of FIG. 14 showing the refined segmentation benefiting from user interactions. Each column of FIG. 14 corresponds to a different image (or different image slice). Likewise, the coloured markings (green, yellow, red and cyan) of FIG. 14 are utilised in the same manner as set out above for FIG. 8, i.e. green is the machine segmentation, yellow is ground truth, red is foreground, cyan is background. It can be observed that CRF-Net(f) improves the segmentation of P-Net better than CRF-Post and CRF-Net(g), as reflected also in the quantitative measurements of Table 3. In particular, these results show that only CRF-Net(f) obtains a significantly better segmentation than P-Net (by itself) with p-value<0.05.

Figure 15:
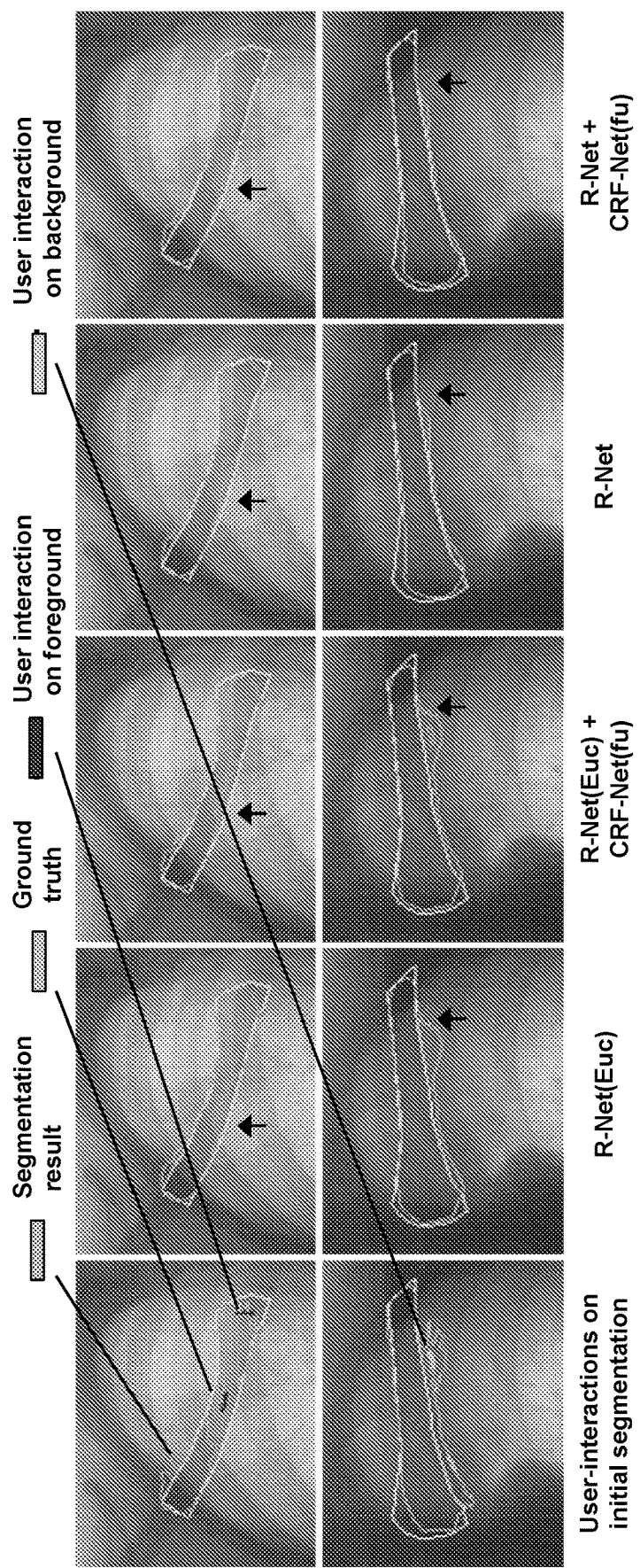
FIG. 15 shows a comparison of the interactive refinement of clavicle segmentation using different using R-Net and certain variations thereof.

FIG. 15 shows examples of interactive refinement of clavicle segmentation using R-Net. This diagram is analogous to FIG. 14, except that the two rows represent different images, and the columns (all but the first) show different segmentation systems for the second machine learning system, i.e. for performing the segmentation after the user interactions have been received. In all cases for FIG. 15, the initial segmentation is obtained by P-Net+CRF-Net(f) (the results of which are shown in the left-most column of FIG. 15), with the user interactions (red/cyan) provided to indicate mis-segmented areas. With the same set of user interactions, the results show four variations of refinement based on R-Net using geodesic or Euclidean distance transforms with or without CRF-Net(fu).

FIG. 15 shows that the segmentation is largely improved by refinements. The white arrows show the local differences between these four variations of refined segmentation. Overall, more accurate results are obtained by using geodesic distance rather than using Euclidean distance for the distance map, and including CRF-Net(fu) can further help to improve the segmentation.

For a quantitative comparison of the approaches shown in FIG. 15, the segmentation accuracy was measured after the first iteration of user refinement (applying R-Net once) and using the different (refined) segmentation methods with the same set of scribbles. Table 4 presents the results of this quantitative evaluation of clavicle segmentation by different interactive methods in terms of Dice score, ASSD, total interactions (scribble length) and user's time. Again, the input is from the segmentation obtained by P-Net+CRF-Net (f), and R-Net(Euc) indicates the use of a Euclidean distance instead of a geodesic distance. A significant improvement from the use of R-Net by itself (p-value<0.05) is shown in bold font. The method involving the combination of R-Net with geodesic distance plus CRF-Net(fu) achieves a higher accuracy than other approaches, with a higher Dice score of 90.22±6.41% and a lower ASSD of 1.73±0.87 pixels. The R-Net+CRF-Net(fu) approach is indicated in Table 4 as providing a significant improvement over the use of R-Net by itself.

TABLE 4

| Method | Dice (%) | ASSD (pixels) |
| --- | --- | --- |
| P-Net + CRF-Net(f) | 84.83 ± 10.52 | 2.65 ± 1.52 |
| R-Net(Euc) | 88.34 ± 8.91 | 2.20 ± 2.17 |
| R-Net | 89.33 ± 7.85 | 1.86 ± 1.02 |
| R-Net(Euc) + CRF-Net(fu) | 88.83 ± 8.32 | 1.96 ± 1.09 |
| R-Net + CRF-Net(fu) | 90.22 ± 6.41 | 1.73 ± 0.87 |

Figure 16:
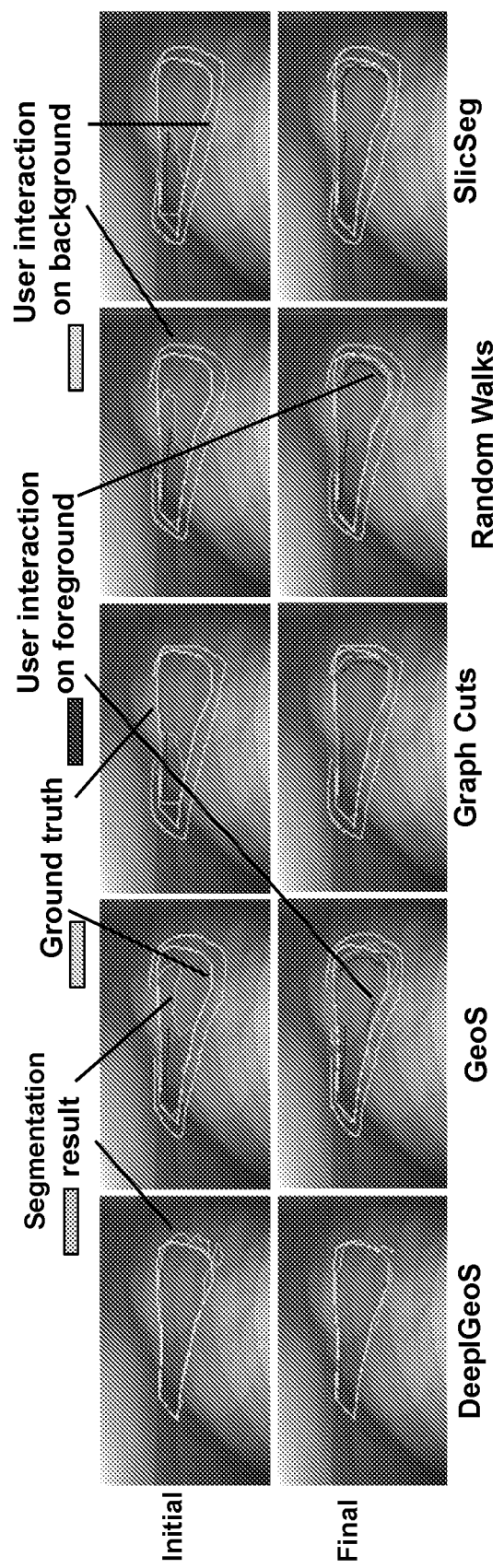
FIG. 16 shows a comparison of segmentation results for the clavicle obtained by using DeeplGeoS (as described herein) and GeoS, Graph Cuts, Random Walks and SlicSeg.
Figure 17:
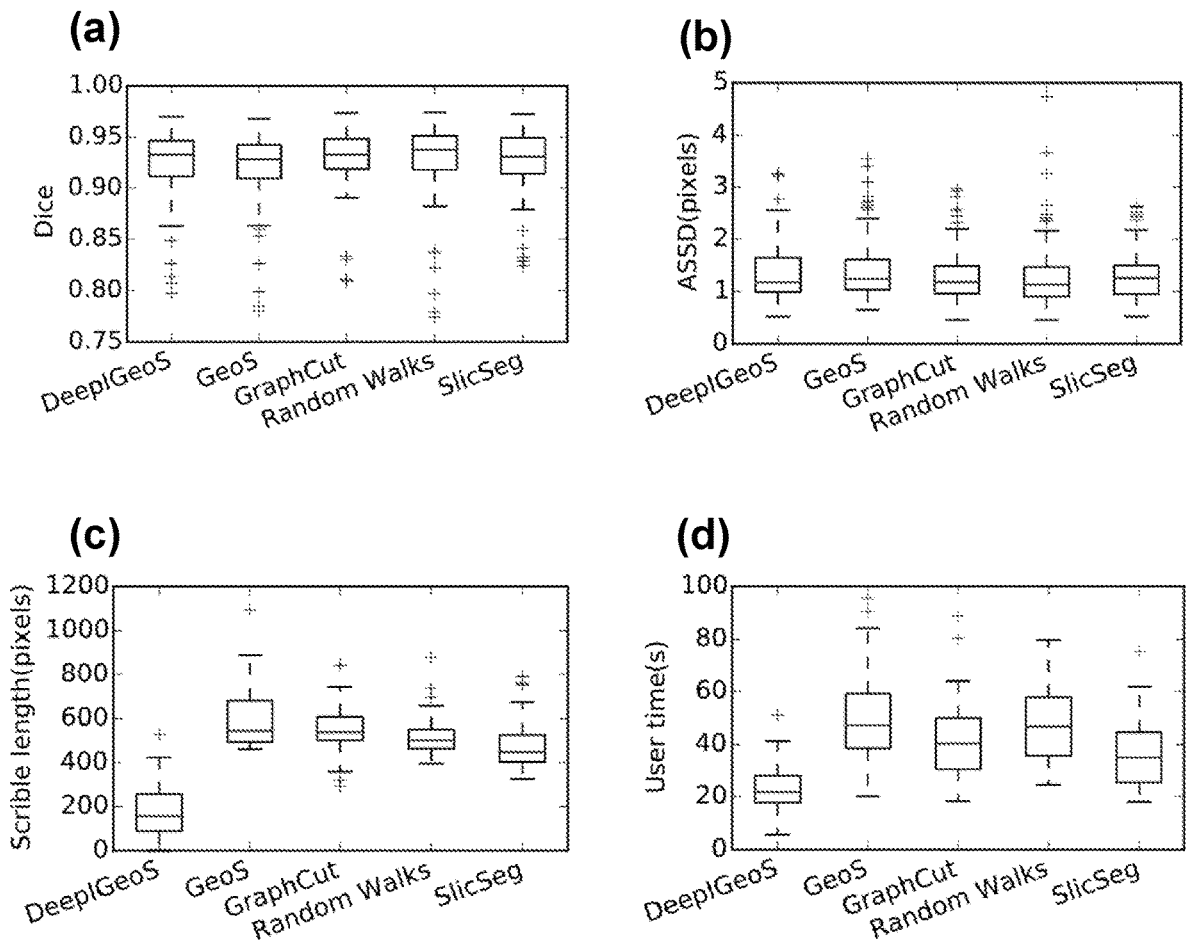
FIG. 17 shows a quantitative comparison of the methods of FIG. 16.

FIG. 16 shows a visual comparison between DeepIGeoS and GeoS [6], Graph Cuts [3], Random Walks [5] and SlicSeg [8] for clavicle segmentation. (The colour marking corresponds to that used in FIGS. 7-10). The first (top) row shows the initial scribbles and the resulting segmentation (N.B., no initial scribbles are needed for DeepIGeoS). The second (lower) row shows the final results after the refinement. It can be seen in FIG. 16 that the initial automatic segmentation by DeepIGeoS has some errors at the head of the clavicle, and it is refined by just two short strokes from the user. In contrast, other interactive methods tend to rely on a large number of interactions for the initial segmentation, and the additional scribbles given for subsequent refinement can also be quite long. It will be appreciated that this reduction in the number (and size) of user interactions shown in FIG. 16 helps to improve the efficiency of the overall segmentation (especially in respect of the amount of time needed from clinicians). FIG. 17 shows a quantitative comparison between the methods of FIG. 16 based on the results given by two users fora final segmentation of the clavicle. In particular, the different methods are compared based on Dice score (FIG. 17a), ASSD (FIG. 17b), total interaction (scribble length) (FIG. 17c) and user's time (FIG. 17d). From FIGS. 17a and 17b, it can be seen that the approach described herein, DeepIGeoS, achieves a similar accuracy to the other interactive methods. However, FIG. 17c shows that DeepIGeoS requires far less input from the user, i.e. the number of pixels indicated in in scribbles is much lower. In other words, the user of the approach described herein is generally able to use smaller, and fewer, indications. As a consequence, it can be seen from FIG. 17d that the time taken by the user for DeepIGeoS is reduced in comparison to the time taken for the other methods, and hence user efficiency is correspondingly increased.

Figure 18:
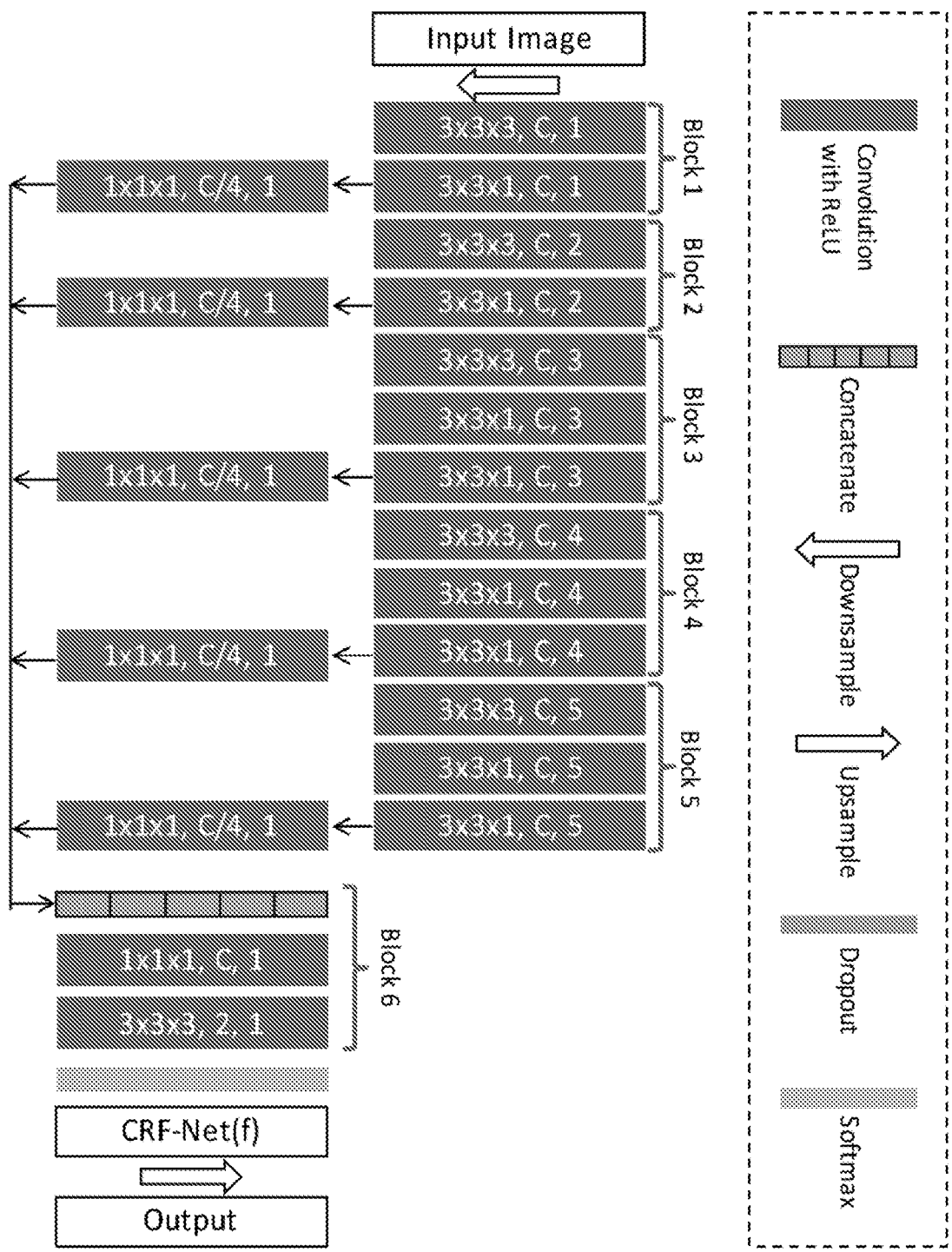
FIG. 18 shows another example structure for the first segmentation network, denoted 3-D P-Net, such as may be used in accordance with the example method of FIG. 1.

FIG. 18 shows an example structure for a first 3D segmentation network, 3D P-Net, which can be regarded as an extension of, and analogous to, the 2D P-Net 110 described above (see for example FIG. 1). This network comprises a resolution preserving 3D convolutional neural network (CNN) structure and a conditional random field (CRF). There are five blocks of convolutional layers. To reduce the memory consumption for 3D images, one downsampling layer is used before the resolution-preserving layers and the output features of blocks 1 to 5 are compressed by a factor four via 1×1×1 convolutions before the concatenation layer.

In FIG. 18, the convolutional layer parameters are represented as (r×r×r, C, I), where r is the convolutional kernel size, C is the number of output channels, and I is the dilation parameter as well as the padding size. The stride of each convolutional layer is set to 1 so that the resolution is kept the same for each of blocks 1 to 6.

A second 3D segmentation network is provided as 3D-R-Net, which can be regarded as analogous to the 2D R-Net 150 described above (see for example FIG. 1). In some implementations, the second machine learning system for 3D images, 3D R-Net, is the same as 3D P-Net, except for the additional input channels, and the use of the user interactions (indications) in CRf-Net (as described above). However, other implementations may use a different configuration or structure for 3D R-Net compared with 3D P-Net.

In one example, 3D P-Net and 3D R-Net with CRF-Net as described above were implemented using the TensorFlow deep learning library (see https://www.tensorflow.orgf). The training process was performed using a system with two 8-core E5-2623v3 Intel processors having a Haswell architecture, two K80 NVIDIA GPUs, and 128 GB memory. The testing process with user interactions was performed on a MacBook Pro (OSX 10.9.5) with 16 GB RAM and an Intel Core i7 CPU running at 2.5 GHz and an NVIDIA GeForce GT 750M GPU. A PyQt GUI graphical user interface (GUI) was developed for user interactions (see https://wiki.python.org/moin/PyQt). It will be appreciated that these computing platforms are provided merely by way of example, and any other suitable computing systems could be used instead.

To evaluate the performance of the above approach, an example implementation of 3D P-Net was compared with DeepMedic[14] and HighRes3DNet[90]. DeepMedic and HighRes3DNet were originally designed for multi-modality or multi-class 3D segmentation, but were adapted them for single modality binary segmentation. 3D P-Net was also compared with a variant, 3D P-Net(b5), which only uses the features from block 5 instead of the concatenated multi-scale features.

To evaluate the user interaction efficiency of the above approach, an example implementation (referred to as DeepIGeoS 3D) was compared with two other interactive segmentation methods:
1) GeoS [6], which computes a probability based on the geodesic distance from user-provided scribbles for pixel classification; and
2) ITK-SNAP [91].
The testing was performed using 3D brain tumor segmentation from FLAIR images, in particular the 2015 Brain Tumor Segmentation Challenge (BraTS) [92] training set with images of 274 cases.

With the development of medical imaging, brain tumors can be imaged by different MR protocols with different contrasts. For example, T1-weighted images highlight part of the tumor and FLAIR acquisitions highlight the peritumoral edema. Segmentation of brain tumors can provide better volumetric measurements and therefore has great potential value for improved diagnosis, treatment planning, and follow-up of individual patients.

The ground truth for the training set was manually delineated by several experts. In contrast to previous work using this dataset for multi-label and multimodality segmentation [14], as a first demonstration of deep interactive segmentation in 3D, only FLAIR images were used from the dataset and only the whole tumor was segmented. 234 cases were randomly selected from the dataset for training and the remaining 40 cases were used for testing. All these images had been skull-stripped and resampled to size of 240×240× 155 with isotropic resolution 1 mm$^3$. Each image was cropped based on the bounding box of its non-zero region. The feature channel number of 3D P-Net and R-Net was C=16.

Figure 19:
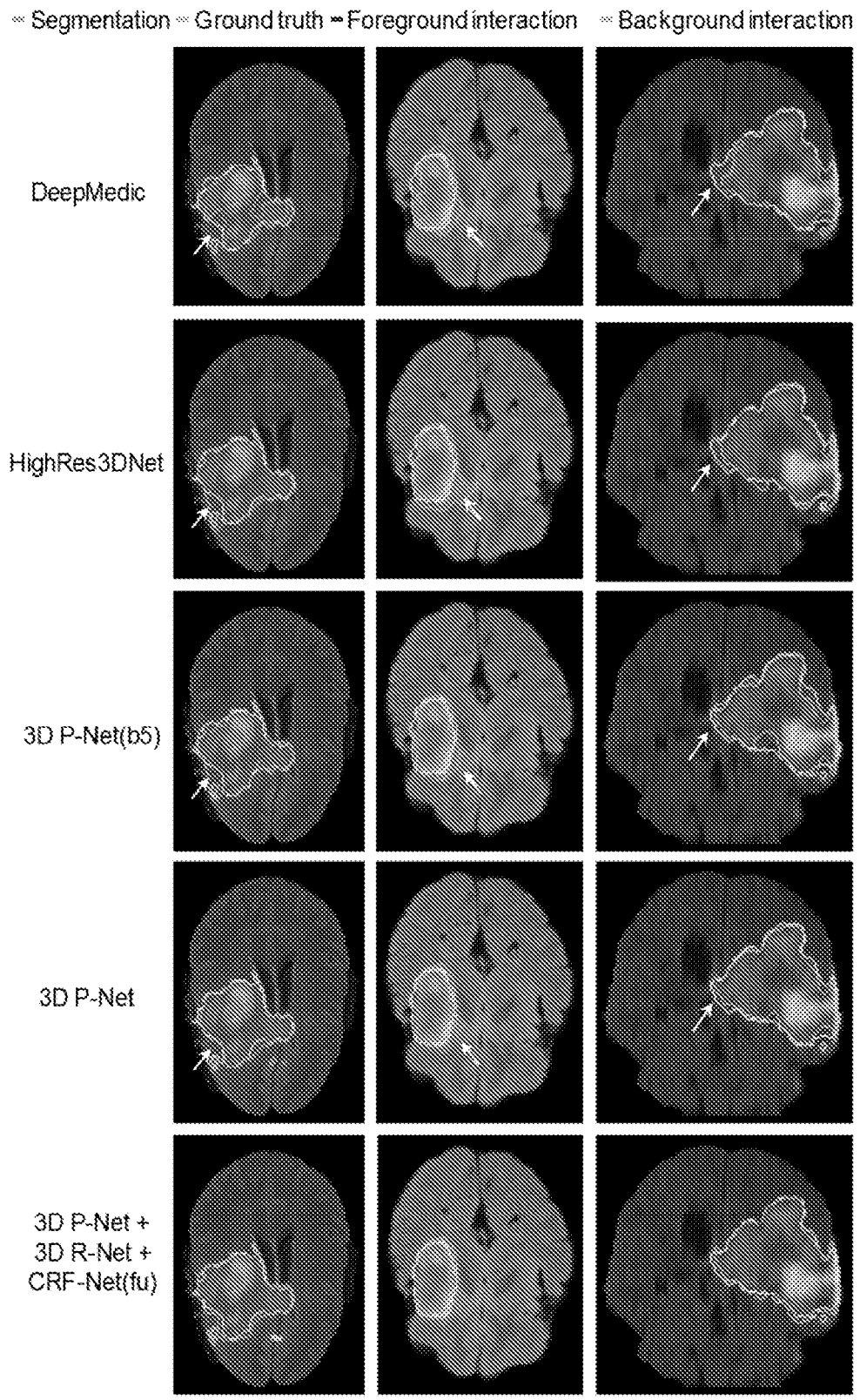
FIG. 19 shows examples of automatic segmentation of a brain tumour using the first segmentation network of FIG. 18.

FIG. 19 shows examples of automatic segmentation of brain tumor using 3D P-Net, in comparison with using DeepMedic, HighRes3DNet and 3D P-Net(b5). In the first column, DeepMedic segments the tumor roughly, with some missed regions near the boundary. HighRes3DNet reduces the missed regions but leads to some over-segmentation. 3D P-Net(b5) obtains a similar result to that of HighRes3DNet. In contrast, 3D P-Net achieves a more accurate segmentation, which is closer to the ground truth. More examples in the second and third columns in FIG. 19 also show 3D P-Net outperforms the other networks.

A quantitative evaluation of these four networks is presented in Table 5. DeepMedic achieves an average Dice score of 83.87%; HighRes3DNet and 3D P-Net(b5) achieve similar performance (to each other), and they both are better than DeepMedic; 3D PNet outperforms all three counterparts with 86.68±7.67% in terms of Dice score and 2.14±2.17 pixels in terms of ASSD. Note also that the proposed 3D P-Net has fewer parameters than HighRes3DNet and is also more memory efficient; 3D P-Net is therefore able to perform inference on a 3D volume in interactive time.

TABLE 5

| Method | Dice (%) | ASSD |
| --- | --- | --- |
| DeepMedic | 83.87 ± 8.72 | 2.38 ± 1.52 |
| HighRes3DNet | 85.47 ± 8.66 | 2.20 ± 2.24 |
| 3D P-Net(b5) | 85.36 ± 7.34 | 2.21 ± 2.13 |
| 3D P-Net | 86.68 ± 7.67 | 2.14 ± 2.17 |
| 3D P-Net + Dense CRF | 87.06 ± 7.23 | 2.10 ± 2.02 |
| 3D P-Net + CRF-Net(f) | 87.55 ± 6.72 | 2.04 ± 1.70 |

Since CRF-RNN [17] was only implemented for 2D, in the context of 3D segmentation 3D CRFNet(f) was compared with 3D Dense CRF [14] that uses manually tuned parameters. A visual comparison between these two types of CRFs working with 3D P-Net is presented in FIG. 20. It can be observed that CRF-Net(f) achieves a more noticeable improvement than Dense CRF when they are used as post-processing without end-to-end learning. A quantitative measurement of Dense CRF and CRF-Net(f) is included in Table 5, and shows that CRF-Net(f) a obtains significantly better segmentation than 3D P-Net by itself, with p-value<0.05.

Figure 21:
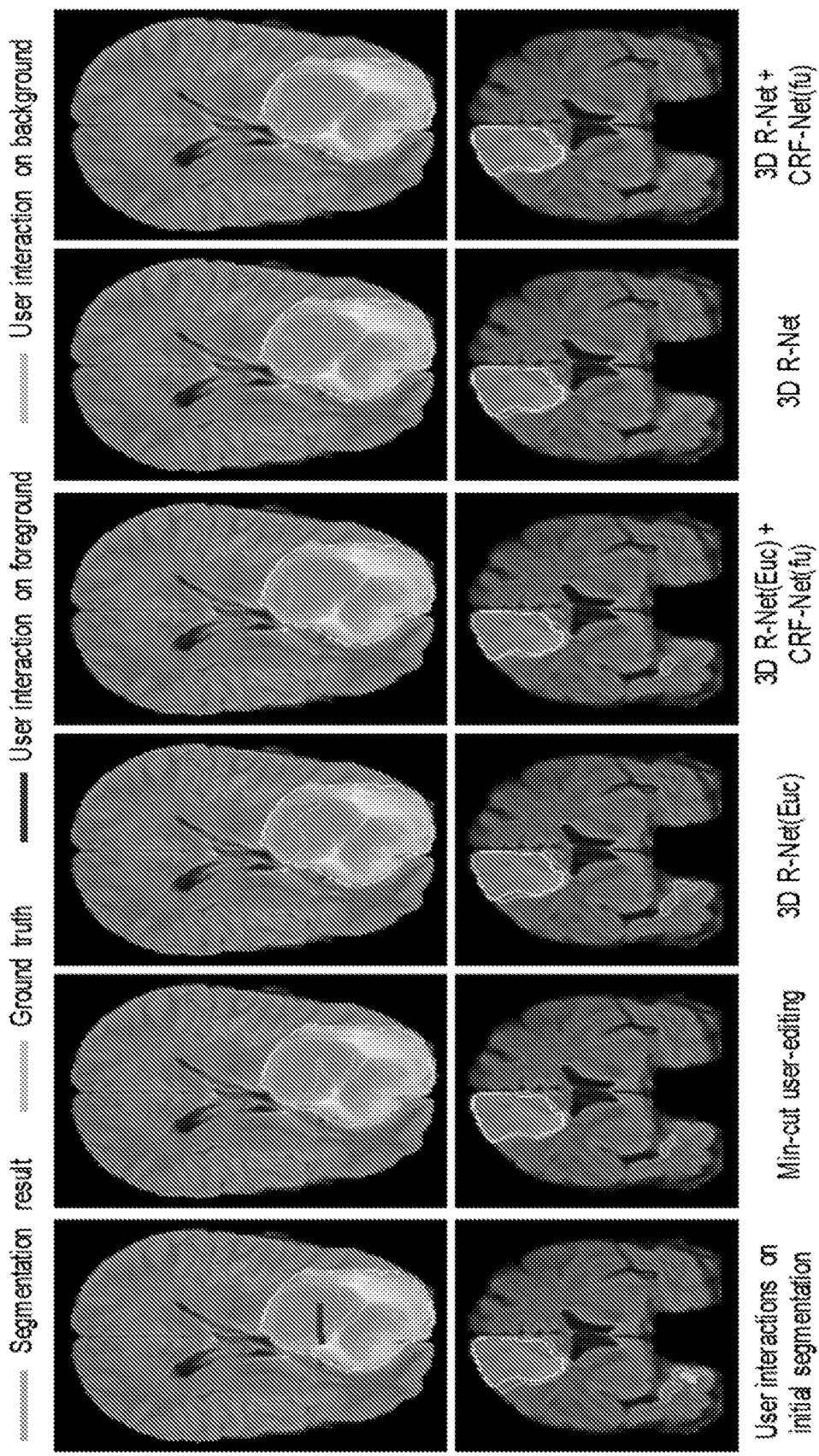
FIG. 21 shows examples of interactive refinement using the first segmentation network of FIG. 18 in conjunction with a conditional random filed (CRF).

FIG. 21 shows examples of interactive refinement of brain tumor segmentation using 3D R-Net in combination with CRF-Net(fu). The initial segmentation is obtained by 3D P-Net+CRF-Net(f). For the same set of user interactions, a comparison was performed with respect to the refined results of min-cut user-editing and four variations of 3D R-Net: using geodesic or Euclidean distance transforms, with or without CRF-Net(fu).

As can be seen in FIG. 21, min-cut user-editing achieves a small improvement, while more accurate results are obtained by using geodesic distance than by using Euclidean distance, and CRF-Net(fu) can further help to improve the segmentation. For quantitative comparison, the segmentation accuracy was measured after the first iteration of refinement, with the same set of scribbles being used for the different refinement methods. The results of this quantitative evaluation are listed in Table 6, and show that the proposed combination of 3D R-Net with geodesic distance and CRF-Net(fu) achieves higher accuracy than the other variations, with a Dice score of 89.93±6.49% and ASSD of 1.43±1.16 pixels.

TABLE 6

| Method | Dice (%) | ASSD |
| --- | --- | --- |
| Before refinement | 87.55 ± 6.72 | 2.04 ± 1.70 |
| Min-cut user-editing | 88.41 ± 7.05 | 1.74 ± 1.53 |
| 3D R-Net(Euc) | 88.82 ± 7.68 | 1.60 ± 1.56 |
| 3D R-Net | 89.30 ± 6.82 | 1.52 ± 1.37 |
| 3D R-Net(Euc) + CRF-Net(fu) | 89.27 ± 7.32 | 1.48 ± 1.22 |
| 3D R-Net + CRF-Net(fu) | 89.93 ± 6.49 | 1.43 ± 1.16 |

Figure 22:
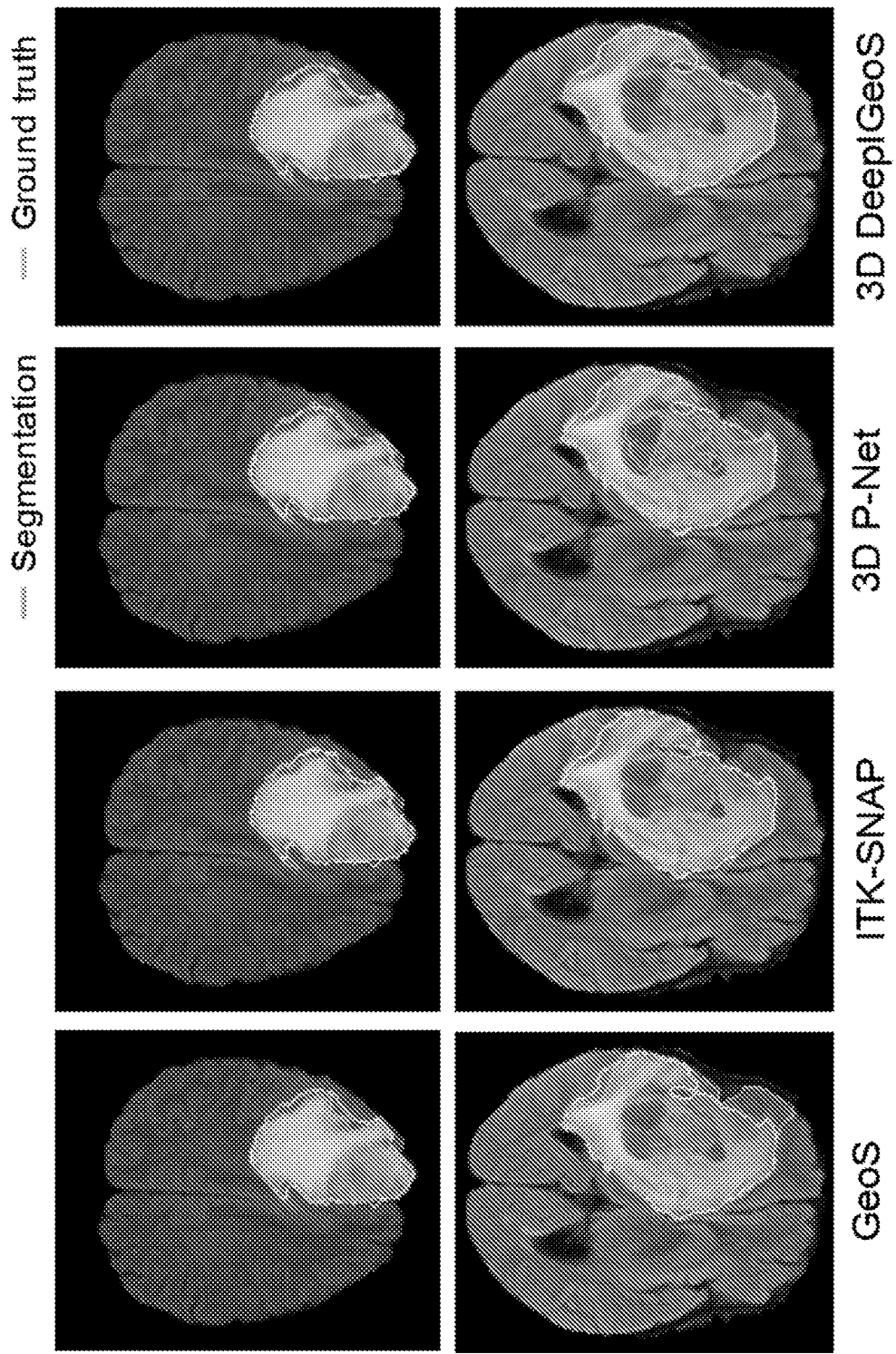
FIG. 22 shows a visual comparison of segmentation results for GeoS, ITKSNAP, 3D-PNET and 3D DeeplGeoS (the latter two as described herein).

FIG. 22 presents a visual comparison between GeoS [6], ITKSNAP [91] and 3D DeeplGeoS.

In the first row, the tumor has a good contrast with the background, and all the compared methods achieve very accurate segmentations. In the second row, a lower contrast makes it difficult for the user to identify the tumor boundary. For this example, DeeplGeoS outperforms GeoS and ITK-SNAP, benefitting from the initial tumor boundary that is automatically identified by 3D P-Net.

Figure 23:
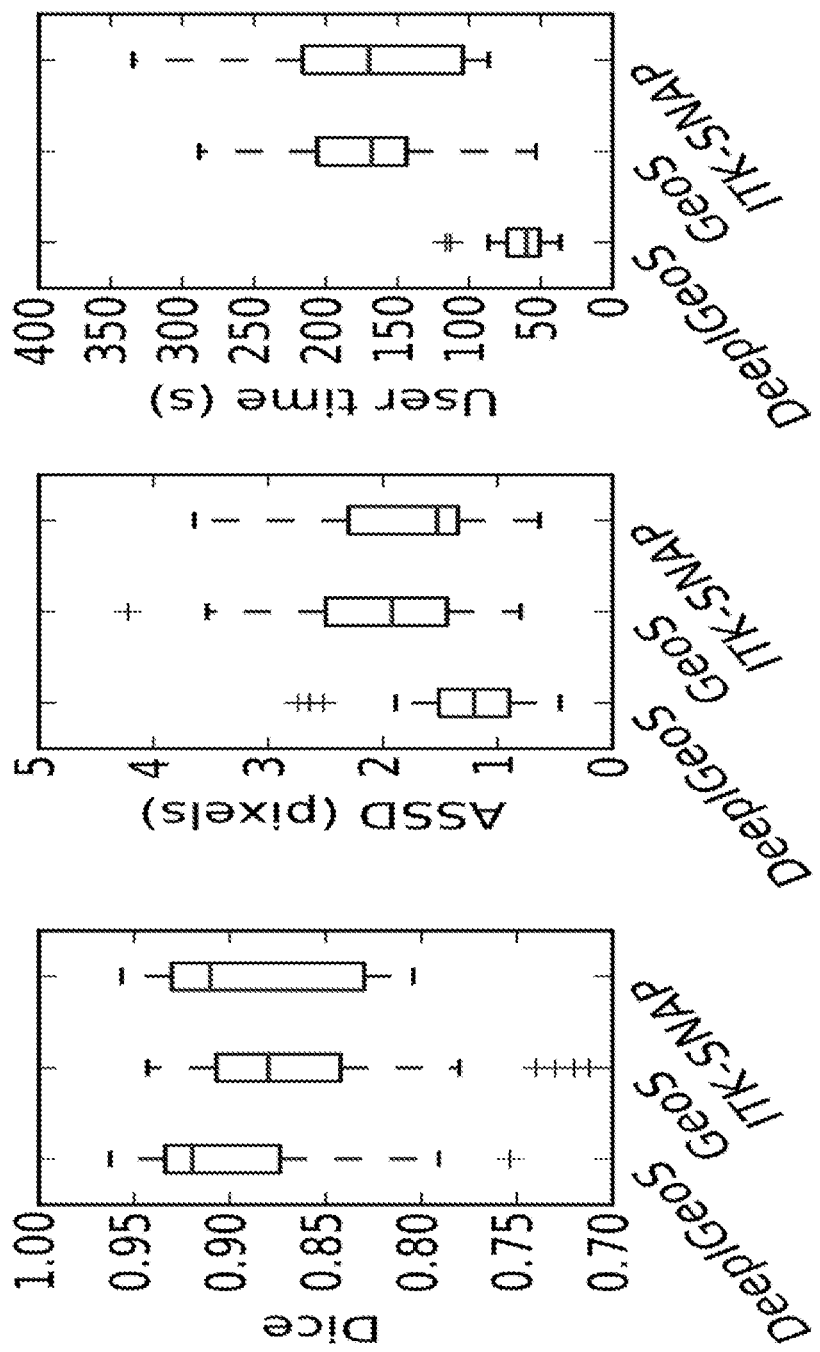
FIG. 23 presents a numerical comparison of segmentation results for GeoS, ITKSNAP, 3D-PNET and 3D DeeplGeoS (the latter two as described herein).

A quantitative comparison of these three approaches is presented in FIG. 23, which confirms that 3D DeeplGeoS achieves higher accuracy compared with GeoS and ITK-SNAP. In addition, the user time required for 3D DeeplGeoS is about one third of that for the other two methods.

Thus DeeplGeoS provides a deep learning-based interactive framework for medical image segmentation. In this approach, a first machine learning system, P-Net, obtains an initial automatic segmentation and a second machine learning system, R-Net, refines the result based on user interactions that are transformed into geodesic distance maps and then integrated into the input for R-Net. A resolution-preserving network structure with dilated convolution is used for dense prediction, and the existing RNN-based CRF has been extended so that it can learn freeform pairwise potentials and take advantage of user interactions as hard constraints. Segmentation results of the placenta from fetal MRI and the clavicle from chest radiographs show that the method described herein achieves better results than automatic CNNs, and obtains similar accuracy with fewer user interactions and less time compared with traditional interactive methods.

Section 2

Convolutional neural networks (CNNs) have achieved state-of-the-art performance for automatic image segmentation. However, they are limited by 1) not being able to generalize well to previously unseen objects as they require labeled instances of an object to be present in the training set; 2) lack of image-specific adaptation and 3) lack of robustness for clinical use. To address these problems, a new interactive segmentation method is proposed that combines CNNs with user-provided bounding boxes and optional scribbles. The method allows supervised and unsupervised image-specific fine-tuning and can segment previously unseen objects. This method is applied to segment multiple organs from fetal MR images. Experiments presented herein show that: 1) this model, trained on the placenta and fetal brain images, can be directly used to segment fetal lungs and maternal kidneys with good performance; 2) image-specific fine-tuning helps to improve segmentation accuracy; 3) this method leads to accurate results with fewer user interactions in less time than GrabCut which is a state-of-the-art bounding box-based interactive segmentation method.

Reviewing in more detail, although convolutional neural networks (CNNs) have become increasingly popular for image segmentation [11], learning from a large number of annotated images to achieve state-of-the-art performance for automatic segmentation of medical images, as exemplified by systems such as U-Net [29], V-Net [30] and DeepMedic [14], three issues still limit the application and performance of CNNs. Firstly, current CNNs used for segmentation do not generalize well to previously unseen objects, as they require labeled instances of each object to be present in the training set. For medical images, annotations are often expensive to acquire as both expertise and time are needed to produce good annotations. Additionally, gathering large sets of images for training can be difficult in some cases. This problem can be alleviated, to some degree, by transfer learning [65] or weakly supervised learning [20]. However, these methods still require a considerable number of annotated instances for every target object and do not allow applying a trained model to segment previously unseen objects directly. Secondly, current CNNs are not adaptive to different test images as parameters of the model are fixed during testing without image-specific adaptation. This can result in a reduction of segmentation accuracy in complex cases. Although it has been shown that image-specific adaptation of a pre-trained model can help to improve segmentation accuracy [87], this has not yet been integrated in CNN-based models. Thirdly, CNNs also suffer from a lack of robustness and unsatisfactory accuracy for clinical use due to the large variations among patients, difficulties in gathering large training datasets, different definitions of anatomical regions across medical centers, and so on. Interactive methods are commonly used to overcome such issues [3, 7], so integrating user interactions into CNNs can potentially lead to more robust results.

A CNN-based method described herein allows segmentation of previously unseen objects and uses image-specific fine-tuning (i.e. adaptation) to further improve accuracy. The CNN is incorporated into an interactive, optionally bounding box-based, binary segmentation and employed to segment a range of different organs, for example, in fetal magnetic resonance (MR) images. By way of example, the model is trained with the placenta and fetal brain only, but as shown herein, the model can also be applied to segment fetal lungs and maternal kidneys that are not present in the training set. It is further demonstrated that image-specific fine-tuning improves segmentation accuracy, and that the method described herein outperforms GrabCut [7], which uses the same interaction style.

Figure 24:
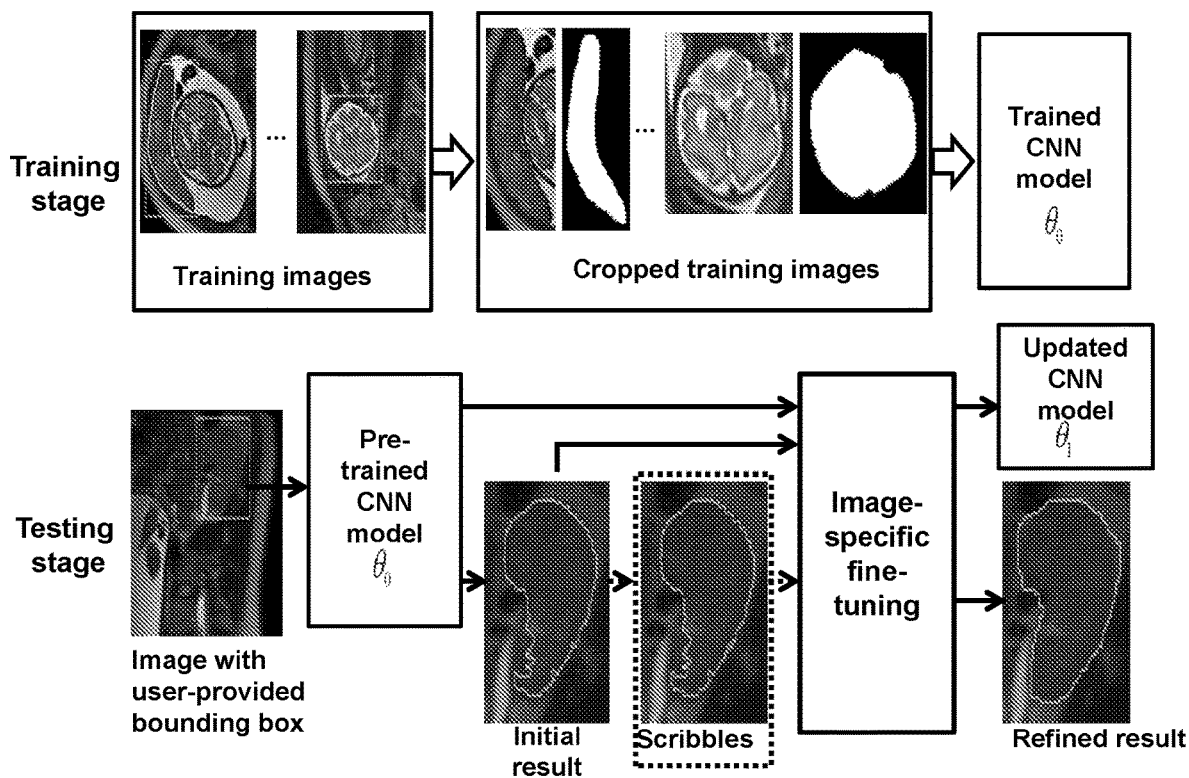
FIG. 24 is a schematic diagram of the training (top) and testing (bottom) stages of a segmentation system as described herein.

An interactive segmentation method described herein using an optional bounding box and image-specific fine-tuning (BIFSeg) is depicted in FIG. 24. To deal with different (including previously unseen) objects in a uniform framework, the present approach uses a CNN that takes as input the content of a bounding box (or the entire image) of one instance (object image) and gives a segmented output. During a training stage, the CNN is trained to segment particular objects within a bounding box. During a test stage, the bounding box is provided by the user, and the segmentation and the CNN are refined through unsupervised (no further user interactions) or supervised (with user-provided scribbles) image-specific fine-tuning.

Figure 25:
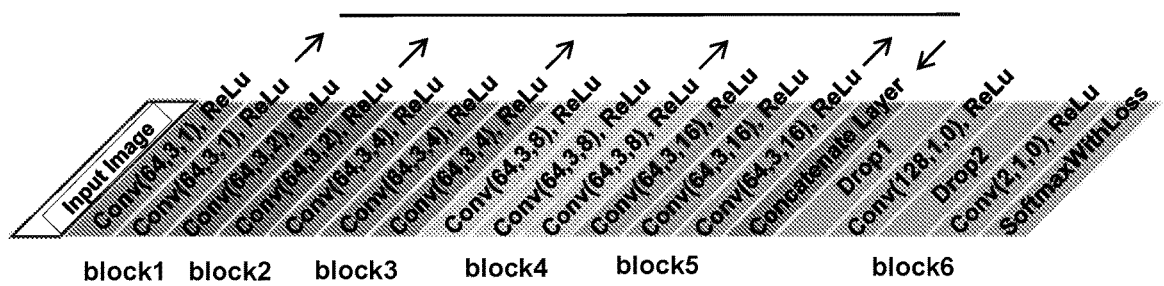
FIG. 25 is a schematic diagram of the network structure of the segmentation system of FIG. 18.

In accordance with some implementations of the present approach, a resolution-preserving network, P-Net, which is a slight variant of the P-Net CNN described above in section 1, is utilised for the bounding box-based binary segmentation. As shown in FIG. 25, P-Net (for this particular implementation) has six blocks: the first five blocks use dilated convolution with 64 output channels, stride 1×1 and convolutional kernel size 3×3; the dilation factor is set to 1, 2, 4, 8 and 16 for these blocks respectively so that they can capture features at different scales; features from block1 to block5 are concatenated and fed into block6, which serves as a pixel-wise classifier. Block6 has two convolutional layers with kernel size 1×1 and dilation factor 0.

We now consider a training set $T=\{(X_1; Y_1), (X_2, Y_2), \ldots\}$ containing K types of objects, where $X_p$ is one training image and $Y_p$ is the corresponding label map. The label set of T is $\{0, 1, 2, \ldots, K\}$ with the background being labelled as 0. Let $N_k$ denote the number of instances of the kth object, so the total number of instances is $N=\sum_k N_k$. Supposing the label of the qth instance in $X_p$ is $I_{pq}$, $Y_p$ may be converted into a binary image $Y_{pq}$ based on whether the value of each pixel in $Y_p$ is equal to $I_{pq}$. The bounding box, $B_{pq}$, of that training instance may be automatically calculated based on $Y_{pq}$ and typically expanded by a given (e.g. fixed or random) margin. $X_p$ and $Y_{pq}$ are cropped based on $B_{pq}$, and so T is converted into a cropped set $\hat{T}=\{(\hat{X}_1, \hat{Y}_1) (\hat{X}_2, \hat{Y}_2), \ldots\}$ with size $\hat{N}$ and label set $\{0,1\}$, where 1 is the label of the instance foreground and 0 the background. The set T can then be used to train the machine learning system (P-Net in the current example) to segment the target inside a bounding box as a binary segmentation problem.

The present approach supports both unsupervised and supervised image-specific fine-tuning for testing. In the testing stage, let X denote the sub-image inside a user-provided bounding box and Y be the target label of X. The set of parameters for the machine learning system (P-Net in this example) is denoted by θ. After obtaining an initial segmentation $Y_0$ given by P-Net, the user may provide (i.e. supervised) or not provide (i.e. unsupervised) a set of scribbles S or other user indications (e.g. clicks) to guide the solving for Y. The approach described herein minimizes an objective function that is similar to GrabCut [7], but uses P-Net instead of Gaussian Mixture Models (GMM).

$$E(Y, \theta) = \sum_i \varphi_u(y_i \mid X, \theta, S) + \lambda \sum_{(i,j)} \varphi_b(y_i, y_j \mid X) \quad (14)$$

where $\varphi_u$ and $\varphi_b$ are the unary and binary energy terms respectively but other objective functions may be used, such as those used in Lazy Snapping [84] or region growing [85], [86]. λ is the weight of $\varphi_b$. $E(Y, \theta)$ is also used by [20] for weakly supervised learning (which is a different task from ours). A typical definition of $\varphi_b$ may be used [3]:

$$\varphi_b(y_i, y_j \mid X) = [y_i \neq y_j] \exp\left(-\frac{(X(i) - X(j))^2}{2\sigma^2}\right) \cdot \frac{1}{d_{ij}} \quad (15)$$

where [•] is $y_i \neq y_j$ is true and 0 otherwise, $d_{ij}$ is the distance between pixel i and pixel j, and σ controls the effect of intensity difference. $\varphi_u$ may also be defined as:

$$\varphi_u(y_i \mid X, \theta, S) = \begin{cases} +\infty & \text{if } i \in S \text{ and } y_i = s_i \\ 0 & \text{if } i \in S \text{ and } y_i \neq s_i \\ -\log P(y_i \mid X, \theta) & \text{otherwise} \end{cases} \quad (16)$$

where $P(y_i|X,\theta)$ can be the softmax output of P-Net considered as a probability or could be computed using other uncertainty measures such as by test time dropout (cite [64]). $s_i$ denotes the user-provided label of a pixel i in S (S might be empty).

The optimization of Equation 14 can be performed as a joint optimisation or can be decomposed into steps that alternatively update label Y and segmentation network θ [20, 7]. In the label update step 370, we fix θ and solve for Y. Since θ and therefore $\varphi_u$ are fixed, Equation 14 can be solved by Graph Cuts [3] (but other solvers may be used depending on the choice of objective function).

In the network update step, Y is typically fixed and we solve for θ. This is equivalent to optimizing P-Net using a single image dataset (X, Y). Let $p_i$ denote the probability of i belonging to the foreground. For the network output, since $y_i$ is set to 1 if $p_i=P(y_i=1|X,\theta)>P(y_i=0|X,\theta)$ and 0 otherwise, there is a high uncertainty (low confidence) of $y_i$ if $p_i$ is close to 0.5. In addition, when S (a user indication such as a scribble) is given to correct $Y_0$, it is likely that pixels close to S have been incorrectly labelled. Such pixels with low confidence or close to a user indication may mislead the update of P-Net. Thus, we penalize such pixels and set the loss function (for example) as:

$$L = \sum_i -w_i(y_i \log p_i + (1 - y_i)\log(1 - p_i)) \quad (17)$$

where $w_i$ is a weighting function defined as:

$$w_i = \begin{cases} \omega & \text{if } i \in S \\ 0 & \text{if } i \notin S \text{ and } (p_0 < p_i < p_1 \text{ or } g_{i,S} < \epsilon) \\ 1 & \text{otherwise} \end{cases} \quad (18)$$

where ω is the weight of scribbles. Pixels with a foreground probability between $p_0$ and $p_1$ are taken as data with low confidence; $g_{i,S}$ is the geodesic distance between i and S, and ϵ is a threshold value. With fixed (X, Y) and the weighted loss function, θ is updated by gradient descent or any other suitable method such as LBFGS (limited memory Broyden-Fletcher-Goldfarb-Shanno). For efficiency reason, it may be advantageous to fix the feature extraction part (block1 to block5) and only update the classifier (block6).

In order to further investigate the method described herein, stacks of T2-weighted MR images from 18 pregnancies in the second trimester were acquired with pixel size 0.74 to 1.58 mm and slice thickness 3 to 4 mm. The placenta and fetal brain from ten volumes were used as the training set. The other eight volumes were used as the testing set, from which it was aimed to segment the placenta, fetal brain, and previously unseen organs such as fetal lungs and maternal kidneys, for which labelled instances were not present in the training set. Due to the large slice thickness and inter-slice motion, the machine learning segmentation was implemented in 2D slices. Manually segmented results (performed by a radiologist) were used as the ground truth. Images were normalized by the mean value and standard variation of training data. To improve segmentation of organs at different scales, the input of P-Net was resized so that the minimal value of width and height was 128 pixels. In the example implementation, P-Net was implemented in Caffe1 (see http://caffe.berkeleyvision.org/) and trained by Stochastic Gradient Decent, with (by way of example) momentum 0.99, batch size 1, weight decay $5\times10^{-4}$, maximal number of iterations 60 k, and initial learning $10^{-3}$ that was halved every 5 k iterations. Training was implemented on a cluster and testing with user interactions was performed on a similar test system as used in section 1, namely a MacBook Pro (OS X 10.9.5) with an NVIDIA GeForce GT 750M GPU. A Matlab graphical user interface (GUI) was again utilised for user interactions.

For image-specific fine-tuning, Y and θ were alternatively updated in four iterations. In each network update step, a learning rate of $10^{-3}$ and iteration number of 20 were used (by way of example). Other parameters were set based on a grid search: λ=3.0, σ=0.1, $p_0$=0.2, $p_1$=0.7, ϵ=0.2.

We compared method described above with GrabCut [7], which is a state-of-the-art bounding box-based interactive segmentation method. GrabCut alternatively updates the Gaussian Mixture Model (GMM) and the image labels, and it also accepts additional scribbles for refinement. For the comparison, the number of components of the GMM was set to 3 and 5 for the foreground and background respectively, while the iteration number was set to 4. We also investigated (i) the initial P-Net output; (ii) the initial P-Net output post-processed with a CRF, i.e., P-Net+CRF, that optimizes Equation 14 by updating Y using a fixed θ; (iii) BIFSeg(−w), in which $w_i$ is fixed to 1 instead of using a weighted loss function (such as in Equations 17 and 18). For a given instance, the same input image was used by all methods. A Dice score between segmentation and the ground truth was used for quantitative evaluation.

Figure 26:
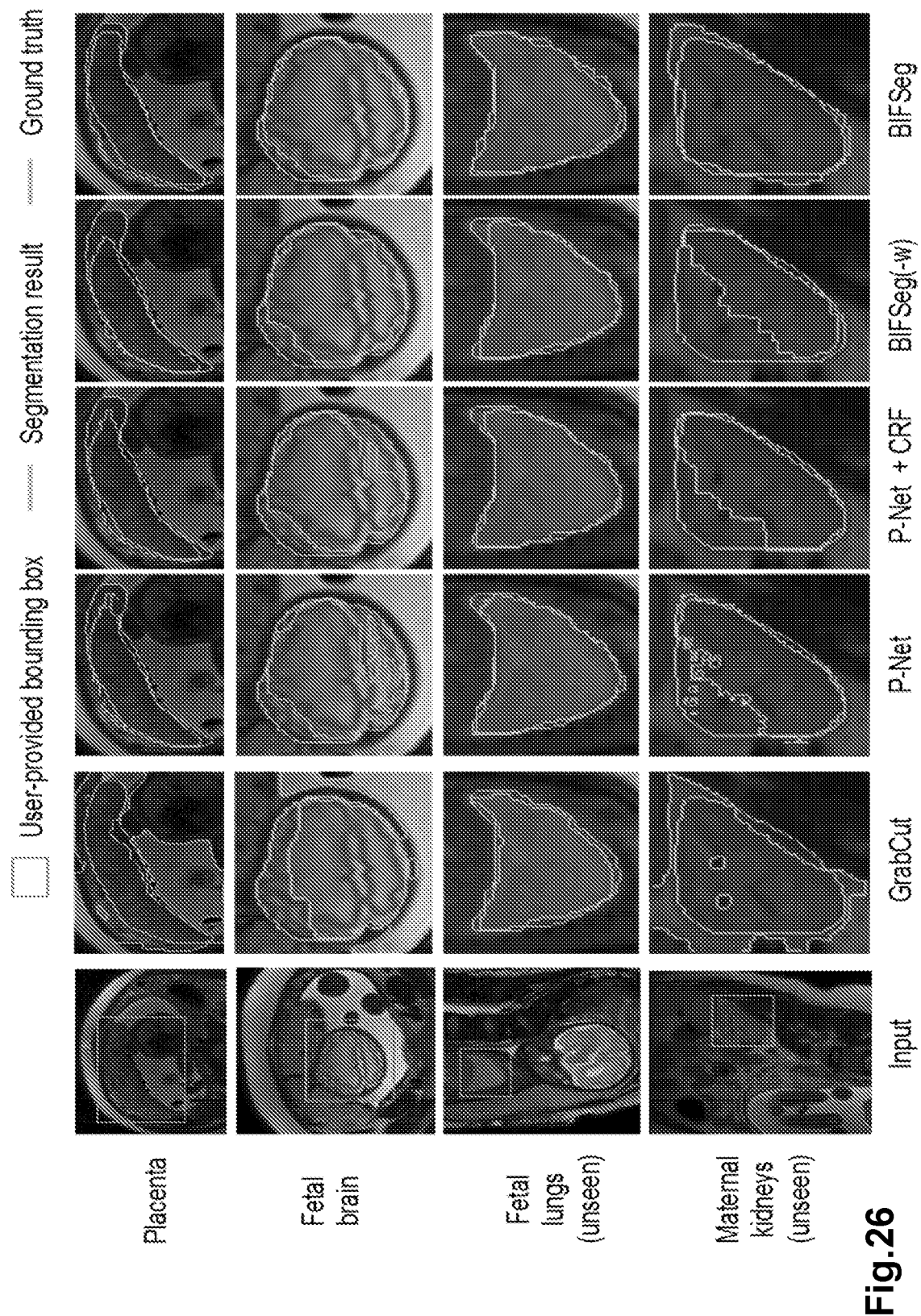
FIG. 26 shows segmentation of the placenta, fetal brain, fetal lungs and maternal kidneys with a user-provided bounding box obtained using different segmentation systems, including that shown in FIG. 24.

FIG. 26 shows the results of segmentation and unsupervised fine-tuning. In particular, FIG. 26 shows rows for the placenta, fetal brain, fetal lungs and maternal kidneys with a user-provided bounding box. The first column presents the bounding box in red for each test image. The second and third columns show the results of GrabCut and P-Net respectively, with a ground truth (yellow-green) and an automated segmentation result (green). It can be observed that GrabCut achieves a good segmentation only for the fetal lung, where there is a good contrast between the lung and the background, and but there are large mis-segmentations for the other three organs. In contrast, P-Net performs noticeably better than GrabCut.

Figure 20:
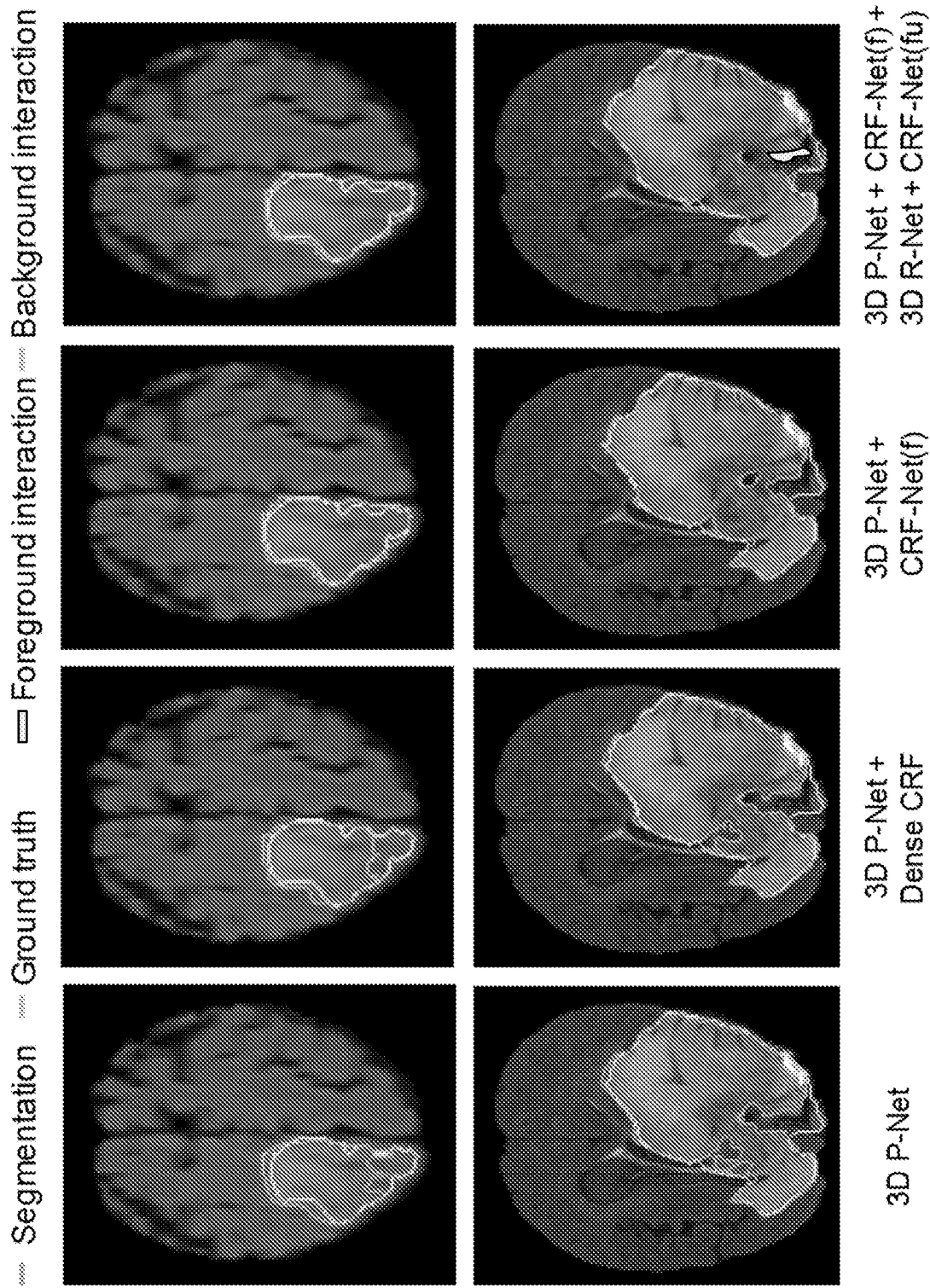
FIG. 20 provides a visual comparison between results obtained using two different types of conditional random filed (CRF) working in conjunction with the first segmentation network of FIG. 18.

Based on the initial output from P-Net, CRF, BIFSeg(−w) and BIFSeg were then used to refine the segmentation without additional scribbles (i.e. unsupervised fine-tuning). FIG. 20 shows that P-Net+CRF and BIFSeg(−w) obtain smoother results than P-Net, but BIFSeg achieves a more noticeable improvement. A quantitative comparison between these algorithms using the same bounding box is presented in Table 7. In particular, Table 7 shows the Dice score and runtime duration of different segmentation methods using a user-provided input image without additional scribbles. A significant improvement of accuracy from P-Net (p-value of Student's t-test<0.05) is shown in bold font. It can be seen from Table 7 that BIFSeg performs better than the other techniques, without any significant increase in runtime duration. It should also be noted that the fetal lungs and maternal kidneys are not seen in the training set.

TABLE 7

|  |  | GrabCut | P-Net | P-Net + CRF | BIFSeg(−w) | BIFSeg |
|---|---|---|---|---|---|---|
| Dice(%) | Placenta | 62.90 ± 12.79 | 84.57 ± 8.37 | 84.87 ± 8.14 | 82.74 ± 10.91 | 86.41 ± 7.50 |
|  | Brain | 83.86 ± 14.33 | 89.44 ± 6.45 | 89.55 ± 6.52 | 89.09 ± 8.08 | 90.39 ± 6.44 |
|  | Lungs | 63.99 ± 15.86 | 83.59 ± 6.42 | 83.87 ± 6.52 | 82.17 ± 8.87 | 85.35 ± 5.88 |
|  | Kidneys | 73.85 ± 7.77 | 85.29 ± 5.08 | 85.45 ± 5.21 | 84.61 ± 6.21 | 86.33 ± 4.28 |
| Runtime(s) |  | 1.62 ± 0.42 | 0.16 ± 0.05 | 0.17 ± 0.05 | 0.87 ± 0.17 | 0.88 ± 0.16 |

Figure 27:
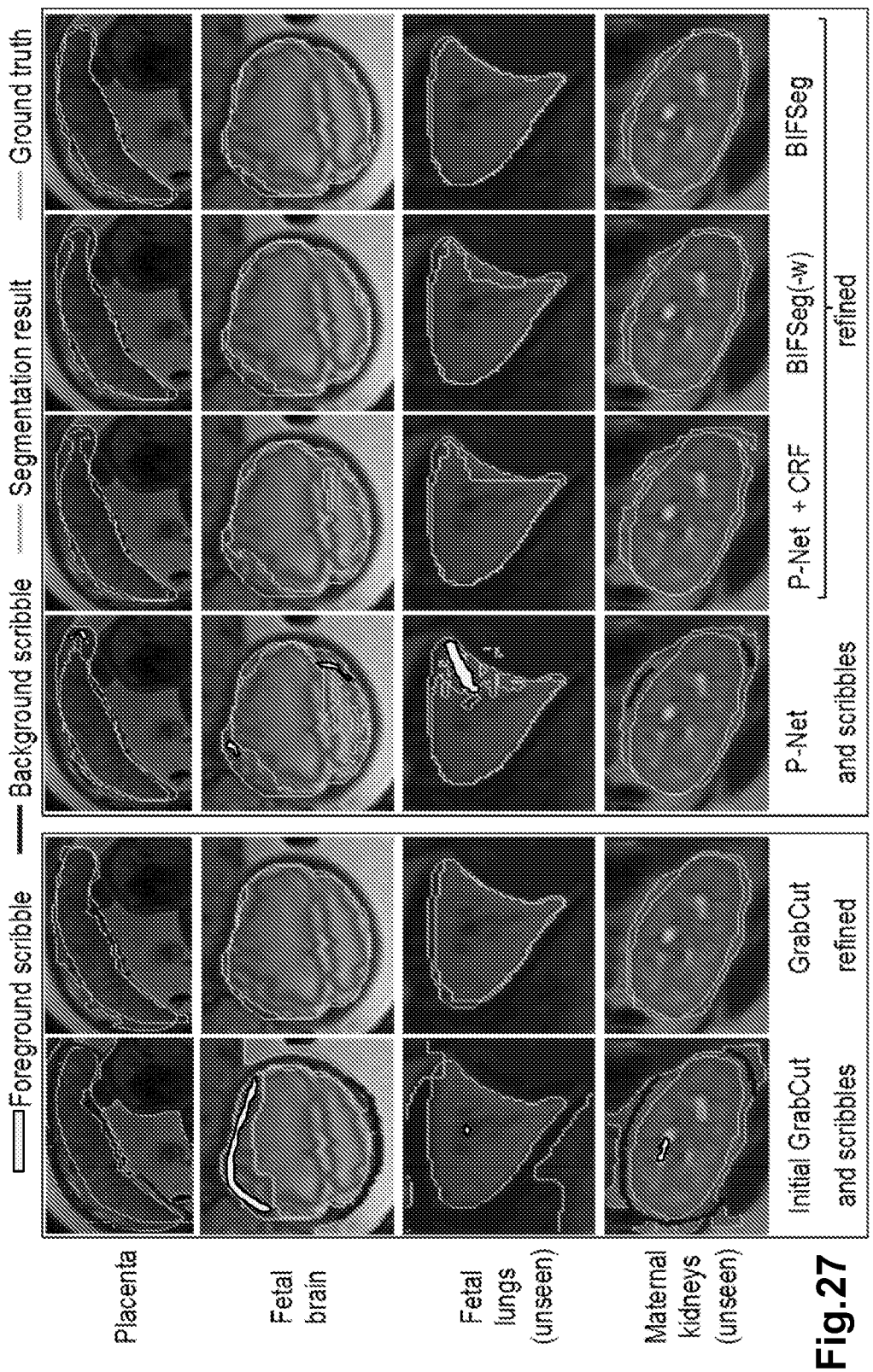
FIG. 27 shows examples of further refinements of the images of FIG. 26 after user indications have been provided.

To investigate supervised fine-tuning, two users (an obstetrician and a radiologist) provided additional scribbles to refine the initial segmentation until a visually acceptable result was achieved. FIG. 27 shows examples of this refinement process, with the rows of FIG. 27 presenting results for the placenta, fetal brain, fetal lungs and maternal kidneys respectively. The first and third columns in FIG. 27 show the initial segmentation and user-provided scribbles for GrabCut and P-Net respectively (again yellow-green represents ground truth and green represents the segmentation produced, with red denoting a foreground scribble, and blue a background scribble. The refined results for GrabCut and BIFSeg are shown in the second and last columns respectively. These two methods achieve similar final results, but BIFSeg uses far fewer scribbles than GrabCut. The same initial segmentation and set of scribbles were used for the comparison of P-Net+CRF, BIFSeg(−w) and BIFSeg (the last three columns in FIG. 27).

Table 8 shows a quantitative evaluation of the Dice score and runtime duration for different segmentation methods using a user-provided bounding box and additional scribbles for refinement. P-Net+CRF, BIFSeg(−w) and BIFSeg all use the same set of scribbles. The runtime duration is measured between the input image being given and the user finishing the segmentation (i.e. the supervised refinement). Significant higher performance, compared with GrabCut (p-value of Student's t-test<0.05) is shown in the bold font.

TABLE 8

|  | Dice(%) | | | | Runtime(s) | |
|---|---|---|---|---|---|---|
|  | GrabCut | P-Net + CRF | BIFSeg(−w) | BIFSeg | GrabCut | BIFSeg |
| Placenta | 89.72 ± 4.18 | 90.13 ± 4.89 | 90.51 ± 4.33 | 92.28 ± 2.47 | 44.71 ± 17.83 | 24.44 ± 13.11 |
| Brain | 95.29 ± 3.48 | 94.45 ± 3.82 | 95.26 ± 3.40 | 95.32 ± 2.39 | 18.84 ± 9.74 | 13.69 ± 6.44 |
| Lungs | 91.91 ± 3.03 | 90.77 ± 4.89 | 90.08 ± 4.96 | 92.45 ± 3.45 | 13.25 ± 7.61 | 9.82 ± 7.50 |
| Kidneys | 91.85 ± 2.48 | 90.84 ± 2.87 | 91.01 ± 2.52 | 92.31 ± 2.52 | 25.49 ± 8.78 | 18.56 ± 7.50 |

It can be seen from Table 8 that, for the fetal brain, fetal lungs and maternal kidneys, GrabCut and BIFSeg achieve similar final Dice scores. For the placenta, however, BIFSeg significantly outperforms GrabCut. In addition, BIFSeg takes significantly less time than GrabCut. The length of scribbles used by GrabCut and BIFSeg is 154.03±83.16 mm and 53.69±44.55 mm respectively, which is also a significant difference. Thus BIFSeg can be seen to achieve similar or even higher accuracy than GrabCut, with fewer user interactions in less time. FIG. 27 and Table 8 also show that BIFSeg outperforms P-Net+CRF and BIFSeg(-w) with the same set of scribbles.

In general terms, the results presented herein show that BIFSeg is able to achieve more accurate initial results in less time than GrabCut when only a bounding box is provided by a user (as per FIG. 26 and Table 7). By receiving additional scribbles from a user for refinement, the results are improved for both (FIG. 27 and Table 8), but BIFSeg requires fewer scribbles and is more efficient.

Figure 28:
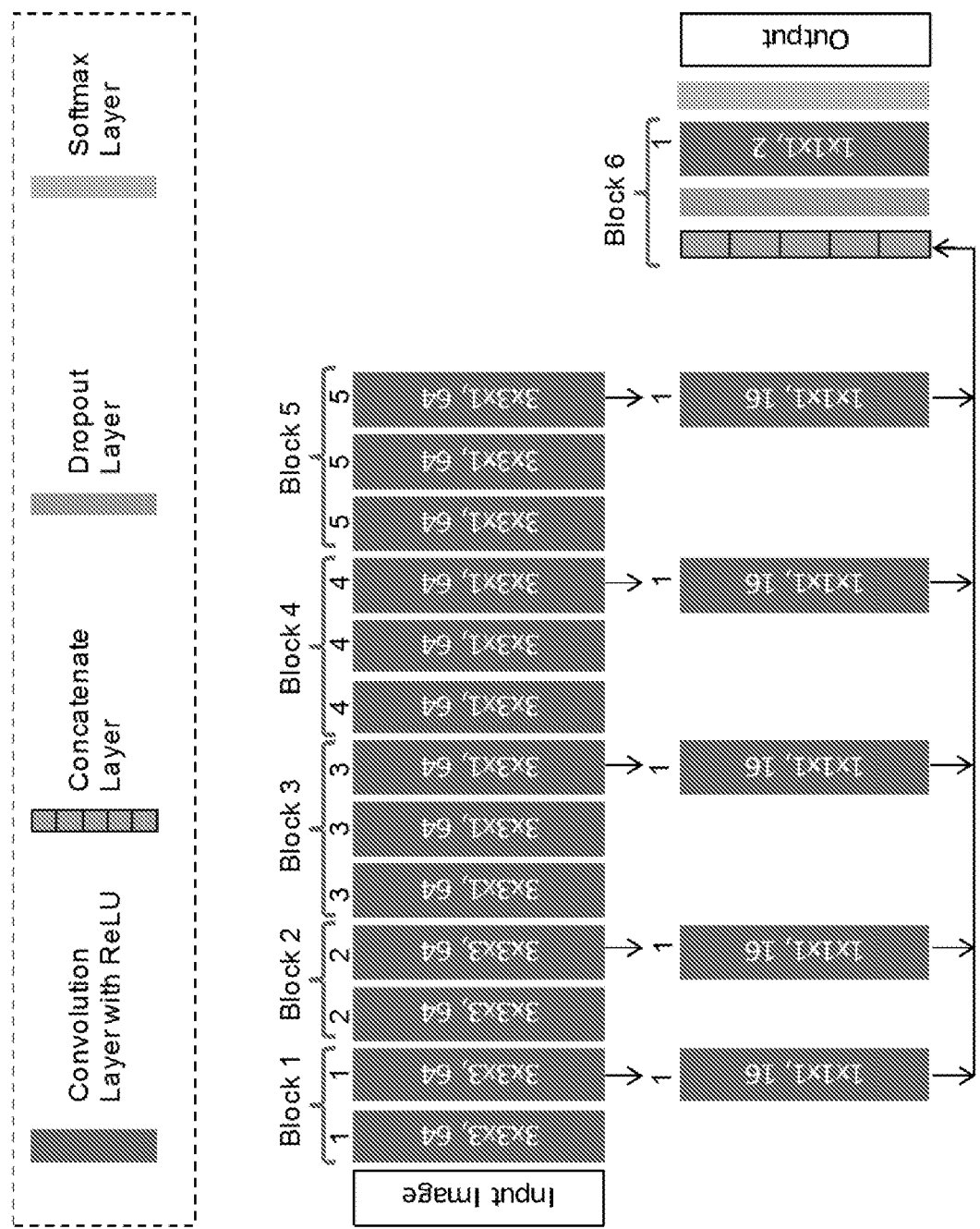
FIG. 28 is a schematic illustration of a resolution-preserving network referred to herein as 3D PC-Net.

The CNN model of BIFSeg is trained with the annotated placenta and fetal brain only, but performs well on previously unseen fetal lungs and maternal kidneys. This is a major advantage compared with traditional CNNs and even transfer learning [65] or weakly supervised learning [20], since for segmenting some objects at least, the system does not require annotated instances for training at all, and so saves time that would otherwise be spent gathering and annotating training data. Although the bounding boxes in the test images used herein were provided by the user, they could also be obtained by automatic detection to further increase efficiency. The uncertainty used by image-specific fine-tuning is based on softmax probability, but it could also be calculated by test-time dropout [64] (although that would be less efficient for the interactive segmentation since it takes longer time for the label update step). In some implementations, a resolution-preserving network, 3D PC-Net, is utilised, as shown in FIG. 28. 3D PC-Net is a slight variant of the 3D P-Net CNN described above in section 1, and is utilised for bounding box-based binary 3D segmentation. 3D PC-Net represents a trade-off between receptive field, inference time and memory efficiency. The network has an anisotropic receptive field of 85×85×9. In contrast to slice-based networks, 3D PC-Net employs 3D contexts. Compared with the use of large isotropic 3D receptive fields, 3D PC-Net has significantly lower memory consumption (especially considering that anisotropic acquisition is often used in Magnetic Resonance (MR) imaging).

3D PC-Net uses 3×3×3 kernels in the first two blocks and 3×3×1 kernels in block 3 through to block 5. Similar to P-Net (see FIG. 1), the classifier (block 6) is fine-tuned with pre-computed concatenated features. To save space for storing the concatenated features, 1×1×1 convolutions are used to compress the features in block 1 through to block 5 and then the features are concatenated. This 3D network with feature compression is referred to herein as (3D) PC-Net.

In order to investigate the method described herein for 3D segmentation, tests were performed using 3D segmentation of brain tumors from T1c and FLAIR images, in particular, the 2015 Brain Tumor Segmentation Challenge (BRATS) training set [92]. The ground truth for these images was manually delineated by experts. The dataset included 274 scans from 198 patients. Each scan incorporated multiple MR sequences with different contrasts. The T1c images highlight the tumor without peritumoral edema, which is designated as the tumor core as per [92]. The FLAIR images highlight the tumor with peritumoral edema, which is designated the whole tumor as per [92]. An investigation was performed of interactive segmentation of the tumor core from T1c images and of the whole tumor from FLAIR images (this is different from previous work on automatic multi-label and multi-modal segmentation [14]).

For this testing, T1c and FLAIR images were randomly selected from 19 patients with a single scan for validation and from 25 patients with a single scan for testing. The T1c images of the remaining patients were used for training, so that the tumor cores in the T1c images were previously seen, while the whole tumors in there FLAIR images were previously unseen for the CNNs. All these images had been skull-stripped and were resampled to isotropic 1 $mm^3$ resolution. The maximal side length of the bounding boxes of the tumor core and the whole tumor ranged from 40 to 100 voxels. The cropped image region inside the bounding box was re-sized so that its maximal side length was 80 voxels. Parameter setting was $\lambda=10.0$, $\sigma=0.1$, $p0=0.2$, $p1=0.6$, $\epsilon=0.2$, $w=5.0$ based on a grid search with the training data—i.e., whole tumor images were not used for parameter learning.

A comparison was performed between the method described above and certain existing approaches, namely 3D GrabCut [93], GeoS[17] and GrowCut [94]. The 3D GrabCut used the same bounding box as used by BIFSeg, with 3 and 5 components for the foreground and background GMMs, respectively. GeoS and GrowCut require scribbles without a bounding box for segmentation. The segmentation results provided by an obstetrician and a radiologist were used for evaluation. For each method, each user provided scribbles to update the result multiple times until the user accepted it as the final segmentation. PC-Net was implemented in Caffe (see http://caffe.berkeleyvision.org/) and trained by Stochastic Gradient Decent, with (by way of example) momentum 0.99, batch size 1, weight decay $5\times10^{-4}$, maximal number of iterations 80 k, and initial learning $10^{-3}$ that was halved every 5 k iterations. Training was implemented on a cluster and testing with user interactions was performed on a similar test system as used in section 1, namely a MacBook Pro (OS X 10.9.5) with an NVIDIA GeForce GT 750M GPU. A PyQt graphical user interface (GUI) was again utilised for user interactions.

Figure 29:
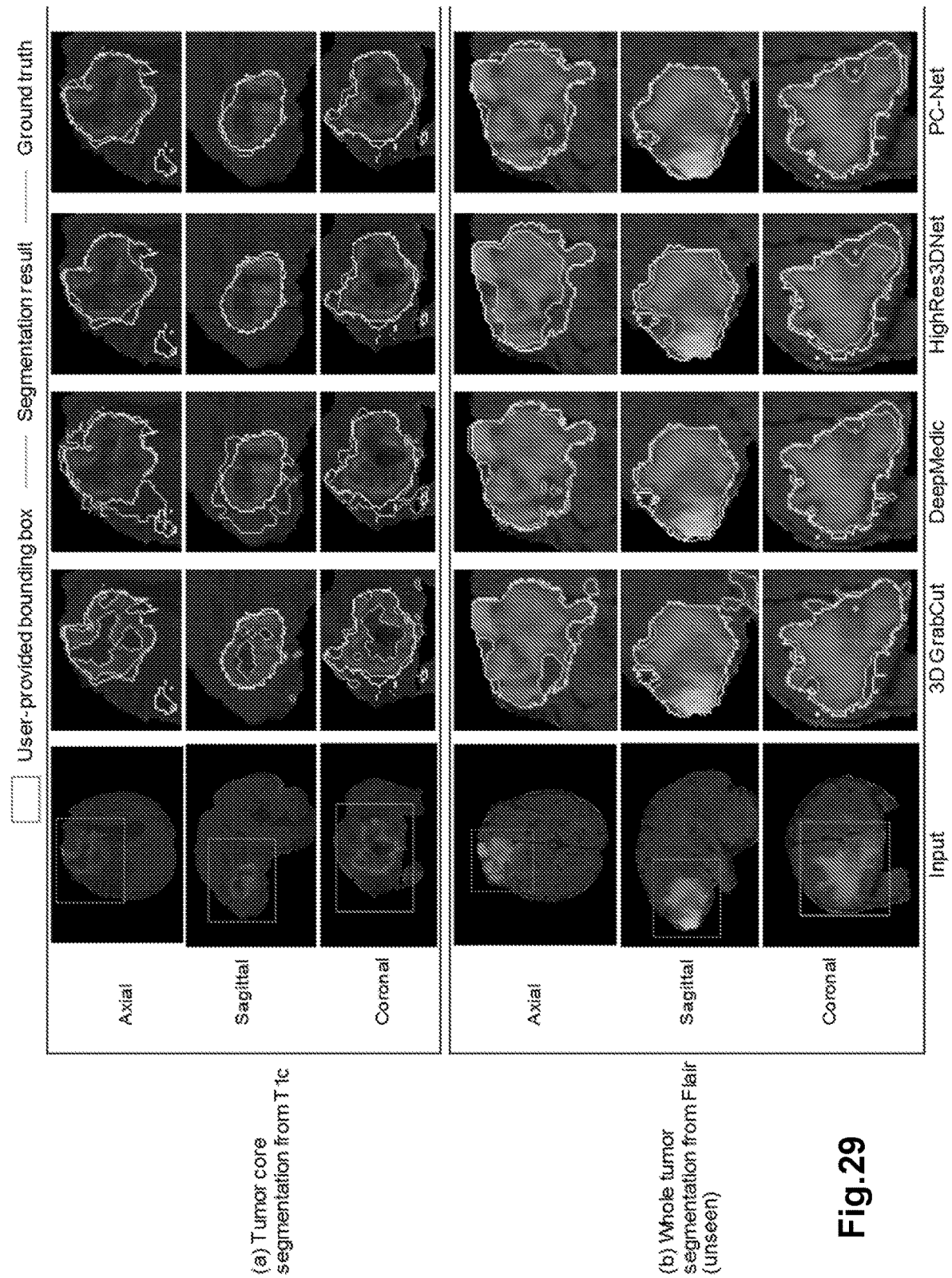
FIG. 29a presents a comparison of the initial result of tumour core segmentation using various approaches.
FIG. 29b shows the initial result of segmentation of a previously unseen whole tumour.

FIG. 29(a) shows an initial result of tumor core segmentation from T1c with a user-provided bounding box. Since the central region of the tumor has a low intensity that is similar to the background, 3D GrabCut obtains large under-segmentations, while DeepMedic produces some over-segmentations. HighRes3DNet and PCNet obtain similar results to one another, but PC-Net is less complex and has lower memory consumption.

FIG. 29(b) shows an initial segmentation result of a previously unseen whole tumor from FLAIR. 3D GrabCut fails to achieve high accuracy due to intensity inconsistency in the tumor region. The CNNs outperform 3D GrabCut, with DeepMedic and PC-Net performing better than HighRes3DNet.

A quantitative comparison based on Dice score is presented in Table 9. It shows that the performance of DeepMedic is low for T1 c but high for FLAIR, and that of HighRes3DNet is the opposite. The average machine time for 3D GrabCut, DeepMedic, and PC-Net is 3.87 s, 65.31 s and 3.83 s, respectively (on the laptop), and that for HighRes3DNet is 1.10 s (on a cluster).

TABLE 9

| Method | DeepMedic | HighRes3DNet | PC-Net | 3D GrabCut |
|---|---|---|---|---|
| Tumor core in T1c | 76.68 ± 11.83 | 83.45 ± 7.87 | 82.66 ± 7.78 | 69.24 ± 19.20 |
| Whole tumor in FLAIR (previously unseen) | 84.04 ± 8.50 | 75.60 ± 8.97 | 83.52 ± 8.76 | 78.39 ± 18.66 |

Figure 30:
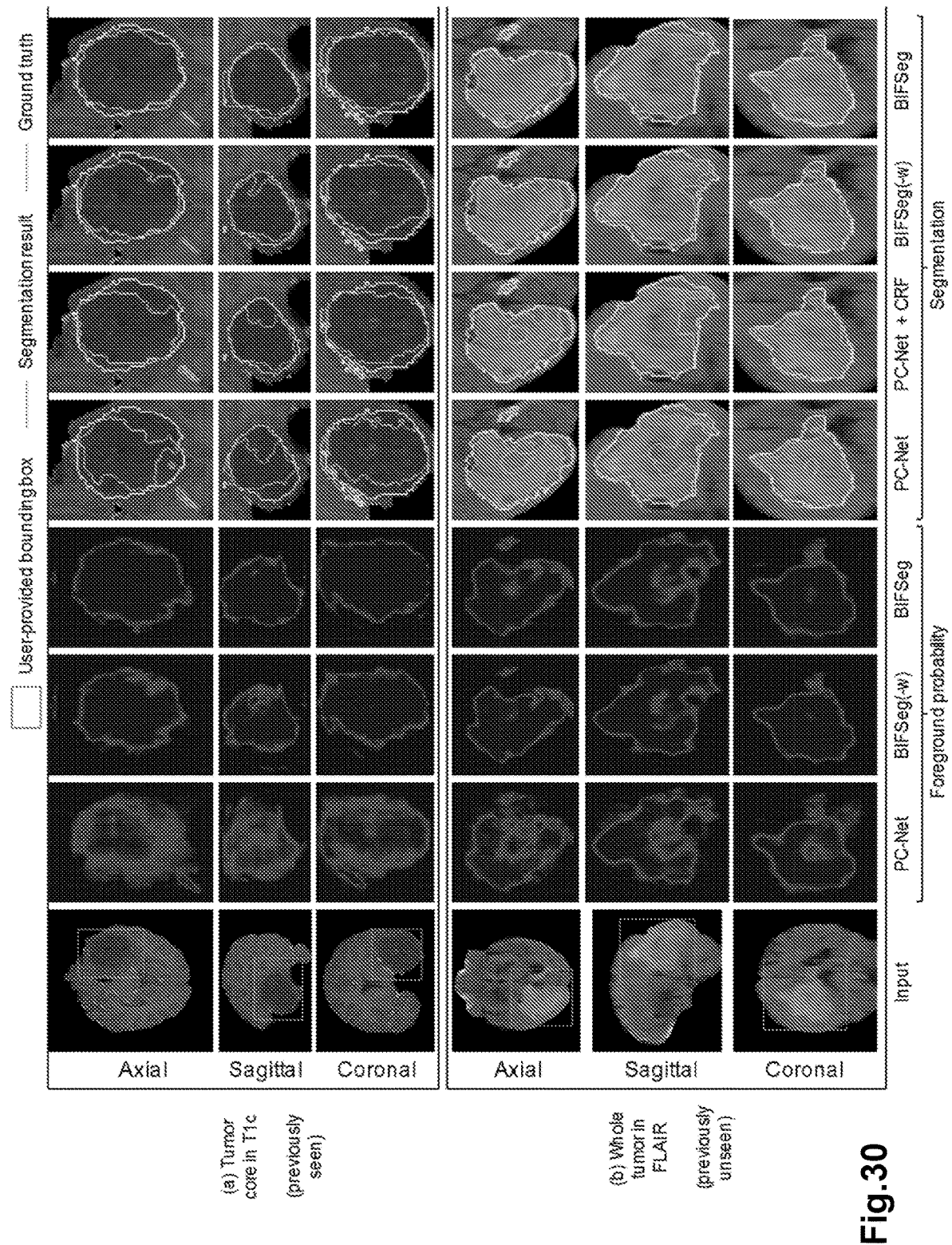
FIG. 30 illustrates results from unsupervised fine-tuning of brain tumor segmentation without additional user interactions.

FIG. 30 shows unsupervised fine-tuning for brain tumor segmentation without additional user interactions. In FIG. 30(a), the tumor core is under-segmented in the initial output of PC-Net. CRF improves the segmentation to some degree, but large areas of under-segmentation still exist. The segmentation result of BIFSeg(-w) is similar to that of CRF. In contrast, BIFSeg performs better than CRF and BIFSeg(-w). A similar situation is observed in FIG. 30(b) for segmentation of a previously unseen whole tumor.

A quantitative comparison of these methods is shown in Table 10. BIFSeg improves the average Dice score from 82.66% to 86.13% for the tumor core, and from 83.52% to 86.29% for the whole tumor.

TABLE 10

| | Method | PC-Net | PC-Net + CRF | BIFSeg(-w) | BIFSeg |
|---|---|---|---|---|---|
| Dice (%) | Tumor core in T1c | 82.66 ± 7.78 | 84.33 ± 7.32 | 84.67 ± 7.44 | 86.13 ± 6.86* |
| | Whole tumor in FLAIR (previously unseen) | 83.52 ± 8.76 | 83.92 ± 7.33 | 83.88 ± 8.62 | 86.29 ± 7.31* |
| Time for refinement (sec) | Tumor core in T1c | — | 0.12 ± 0.04* | 3.36 ± 0.82 | 3.32 ± 0.82 |
| | Whole tumor in FLAIR (previously unseen) | — | 0.11 ± 0.05* | 3.16 ± 0.89 | 3.09 ± 0.83 |

Figure 31:
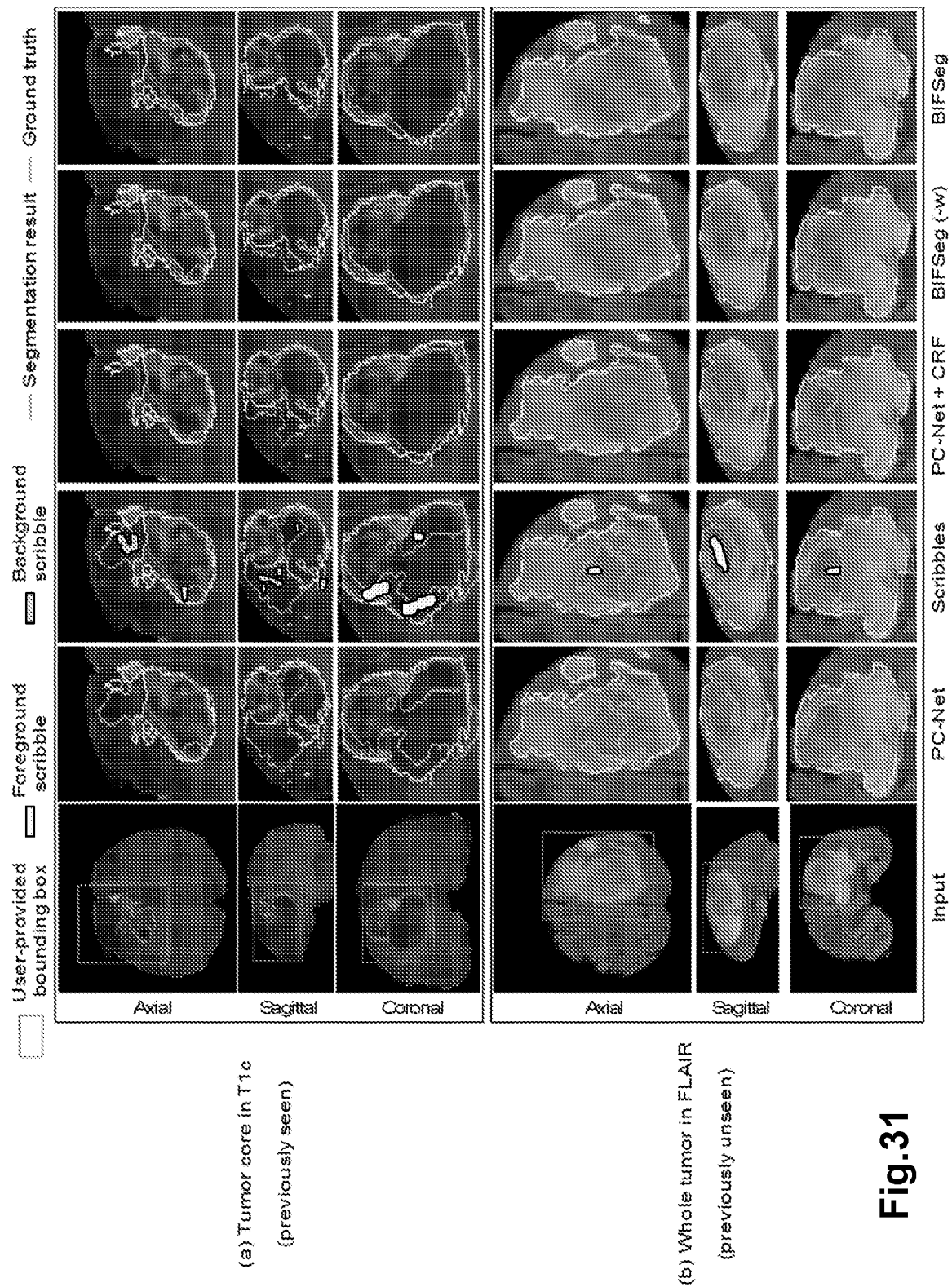
FIG. 31 illustrates refined results from brain tumor segmentation with additional scribbles provided by the user.

FIG. 31 shows refined results of brain tumor segmentation with additional scribbles provided by the user. The same initial segmentation based on PC-Net and the same scribbles are used by CRF, BIFSeg(-w) and BIFSeg. It can be observed that CRF and BIFSeg(-w) correct the initial segmentation moderately. In contrast, BIFSeg achieves better refined results for both the tumor core in T1c and the whole tumor in FLAIR. For a quantitative comparison, the segmentation accuracy was measured after a single round of refinement using the same set of scribbles based on the same initial segmentation. The results are presented in Table 11, showing BIFSeg significantly outperforms CRF and BIFSeg (-w) in terms of Dice score. Tables 10 and 11 therefore show that supervised fine-tuning achieves a Dice score which is 1.3-1.8 percentage points higher than achieved by unsupervised fine-tuning for brain tumor segmentation.

TABLE 11

| | Method | PC-Net | PC-Net + CRF | BIFSeg(-w) | BIFSeg |
|---|---|---|---|---|---|
| Dice (%) | Tumor core in T1c | 82.66 ± 7.78 | 85.93 ± 6.64 | 85.88 ± 7.53 | 87.49 ± 6.36* |
| | Whole tumor in FLAIR (previously unseen) | 83.52 ± 8.76 | 85.18 ± 6.78 | 86.54 ± 7.49 | 88.11 ± 6.09* |
| Time for refinement (sec) | Tumor core in T1c | — | 0.14 ± 0.06* | 3.33 ± 0.86 | 4.42 ± 1.88 |
| | Whole tumor in FLAIR (previously unseen) | — | 0.12 ± 0.05* | 3.17 ± 0.87 | 4.01 ± 1.59 |

Figure 32:
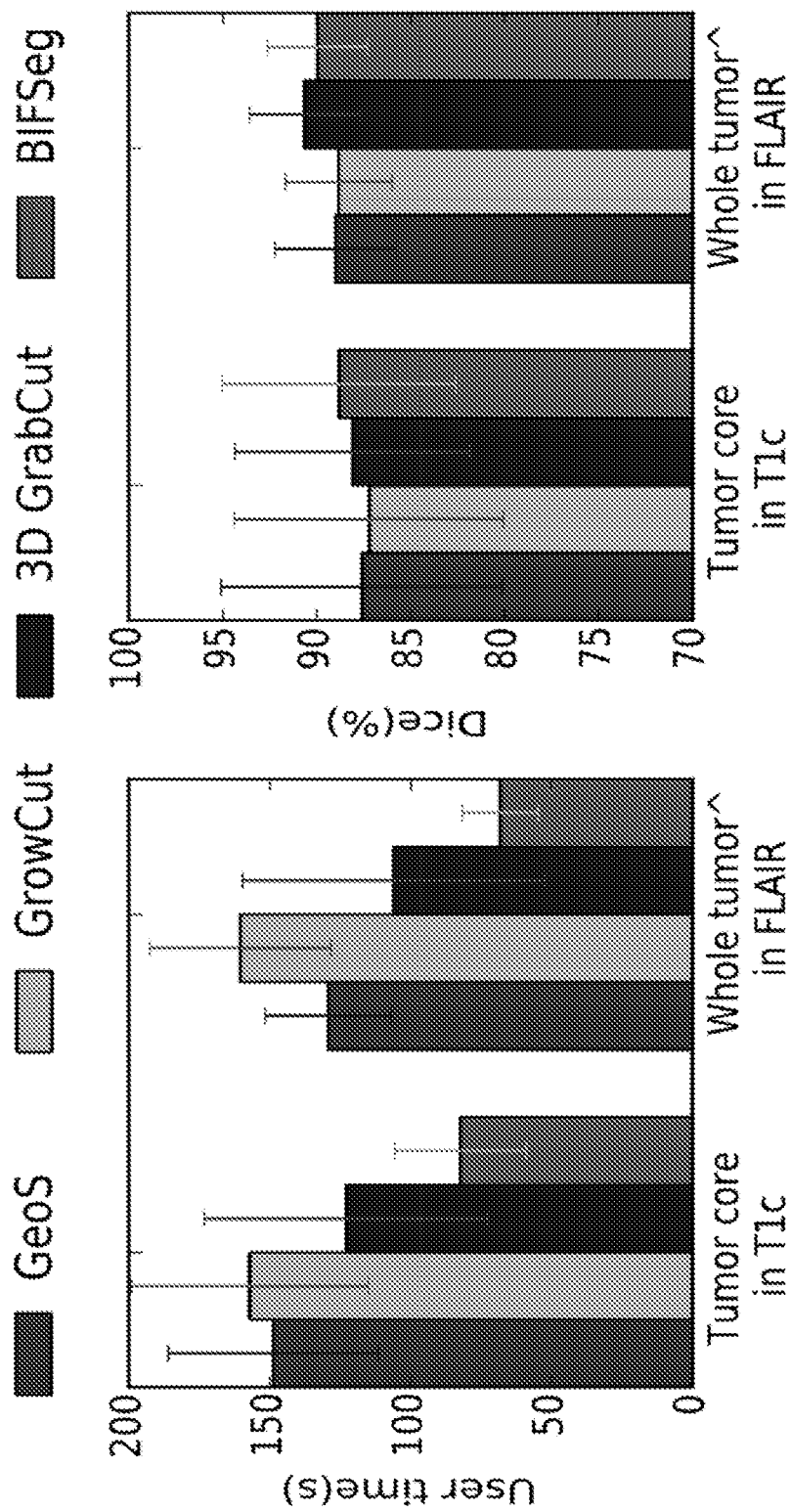
FIG. 32 shows the DICE score obtained for different types of interactive method.

The two users (the obstetrician and radiologist) used GeoS [6], GrowCut [94], 3D GrabCut [93] and BIFSeg for the brain tumor segmentation tasks. The user time and final accuracy of these methods are presented in FIG. 32, which shows that these interactive methods achieve similar final Dice scores for each task. However, BIFSeg takes significantly less user time, namely 82.3 s and 68.0 s on average for the tumor core and the whole tumor, respectively.

In summary, the example segmentation method that combines CNNs with user interactions has been shown to allow image-specific fine-tuning. As described herein, segmentation was performed on an input image using a CNN for binary segmentation, and it has been shown that this segmentation is operable to identify previously unseen objects. A uniform framework is proposed for both unsupervised and supervised refinement of initial segmentation, where image-specific fine-tuning is used for adaptation. The experiments on fetal MR images show that the method performs well on previously unseen objects, achieving similar or even higher accuracy with fewer user interactions in less time than GrabCut.

Section 3

Deep convolutional neural networks are powerful tools for learning visual representations from images. However, designing efficient deep architectures to analyse volumetric medical images remains challenging, especially in the context of 3D or higher dimensionality interactive segmentation. The present application investigates efficient and flexible elements of modern convolutional networks such as dilated convolution and residual connection. With these building blocks, a high-resolution, compact convolutional network is proposed for volumetric image segmentation. To illustrate the efficiency of this approach for learning 3D representation from large-scale image data, the proposed network is validated with the challenging task of parcellating 155 neuroanatomical structures from brain MR images. These experiments show that the proposed network architecture compares favourably with state-of-the-art volumetric segmentation networks while being an order of magnitude more compact. In addition, the brain parcellation task is considered as a pretext task for volumetric image segmentation; the trained network described herein provides a potentially good starting point for transfer learning. Additionally, the feasibility is shown of voxel-level uncertainty estimation using a sampling approximation through dropout.

Reviewing in more detail, convolutional neural networks (CNNs) have been shown to be powerful tools for learning visual representations from images. They often consist of multiple layers of non-linear functions with a large number of trainable parameters. Hierarchical features can be obtained by training the CNNs discriminatively. In the medical image computing domain, recent years have seen a growing number of applications using CNNs. Although there have been recent advances in tailoring CNNs to analyse volumetric images, most of the work to date studies image representations in 2D. While volumetric representations are more informative, the number of voxels scales cubically with the size of the region of interest. This raises challenges of learning more complex visual patterns as well as higher computational burden compared to the 2D cases. While developing compact and effective 3D network architectures is of significant interest, designing 3D CNNs remains a challenging problem.

The present approach provides a high-resolution and compact network architecture for the segmentation of fine structures in volumetric images. For this purpose, the simple and flexible elements of modern convolutional networks are investigated, such as dilated convolution and residual connection. Most existing network architectures follow a fully convolutional downsample-upsample pathway [14, 72, 73, 18, 30, 74]. Low-level features with high spatial resolutions are first downsampled for higher-level feature abstraction; then the feature maps are upsampled to achieve high-resolution segmentation. In contrast to these techniques, the approach described here provides a 3D architecture that incorporates high spatial resolution feature maps throughout the layers, and can be trained with a wide range of receptive fields.

The resulting network is validated on the challenging task of automated brain parcellation into 155 structures from T1-weighted MR images. It is shown that the proposed network, with twenty times fewer parameters, achieves competitive segmentation performance compared with state-of-the-art architectures. In addition, such a network could be trained with a large-scale dataset to enable transfer learning to other image recognition tasks [88]. In the field of computer vision, the well-known AlexNet and VGG net were trained on the ImageNet dataset. They provide general-purpose image representations that can be adapted for a wide range of computer vision problems. Given the large amount of data and the complex visual patterns of the brain parcellation problem, we consider it as a pretext task. The trained network described herein can be considered as a step towards a general-purpose volumetric image representation, potentially providing an initial model for transfer learning to other volumetric image segmentation tasks.

The uncertainty of the segmentation is also an important parameter for indicating the confidence and reliability of an algorithm [64, 75, 76]. The high uncertainty of a labelling can be a sign of an unreliable classification. The feasibility of voxel-level uncertainty estimation is demonstrated herein using Monte Carlo samples of the proposed network with dropout at test time. Compared to the existing volumetric segmentation networks, this compact network has fewer parameter interactions and thus potentially achieves better uncertainty estimates with fewer samples.

In relation to 3D convolutional networks, to maintain a relatively low number of parameters, the present approach uses small 3D convolutional kernels with only $3^3$ parameters for all convolutions. This is about the smallest kernel that can represent 3D features in all directions with respect to the central voxel. Although a convolutional kernel with 5×5×5 voxels gives the same receptive field as stacking two layers of 3×3×3-voxel convolution, the latter has approximately 57% fewer parameters. Using smaller kernels implicitly imposes more regularisation on the network while achieving the same receptive field.

To further enlarge the receptive field to capture large image contexts, most of the existing volumetric segmentation networks downsample the intermediate feature maps. This significantly reduces the spatial resolution. For example, 3D U-net [18] heavily employs 2×2×2-voxel max pooling with strides of two voxels in each dimension. Each max pooling reduces the feature responses of the previous layer to only ⅛ of its spatial resolution. Upsampling layers, such as deconvolutions, are often used subsequently to partially recover the high resolution of the input. However, adding deconvolution layers also introduces additional computational costs.

Recently, Chen et al. [16] used dilated convolutions with upsampled kernels for semantic image segmentation. The advantages of dilated convolutions are that the features can be computed with a high spatial resolution, and the size of the receptive field can be enlarged arbitrarily. Dilated convolutions can be used to produce accurate dense predictions and detailed segmentation maps along object boundaries.

In contrast to the downsample-upsample pathway, dilated convolutions for volumetric image segmentation are adopted herein. More specifically, the convolutional kernels are upsampled with a dilation factor r. For M-channels of input feature maps I, the output feature channel O generated with dilated convolutions is given by:

$$O_{x,y,z} = \sum_{m=0}^{M-1} \sum_{i=0}^{2} \sum_{j=0}^{2} \sum_{k=0}^{2} w_{i,j,k,m} I_{(x+ir),(y+jr),(x+kr),m}; \quad (19)$$

where the index tuple (x,y,z) runs through every spatial location in the volume; the kernels w consist of $3^3 \times M$ trainable parameters (although other approaches could be used, such as interpolating the kernel, rather than using zero filing). The dilated convolution in Equation 19 has the same number of parameters as the standard 3×3×3 convolution. It preserves the spatial resolution and provides a $(2r+1)^3$-voxel receptive field. Setting r to 1 reduces the dilated convolution to the standard 3×3×3 convolution. In practice, the 3D dilated convolutions were implemented with a split-and-merge strategy [16] to benefit from the existing GPU convolution routines.

Residual connections were first introduced and later refined by He et al. [26, 77] for the effective training of deep networks. The key idea of a residual connection is to create identity mapping connections to bypass the parameterised layers in a network. The input of a residual block is directly merged to the output by addition. The residual connections have been shown to make information propagation smoother and to help improve the training speed [26].

Figure 33:
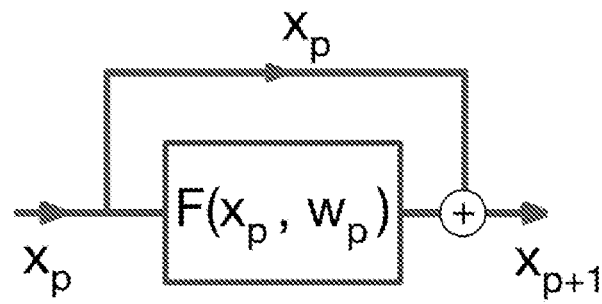
FIG. 33 is a schematic diagram of a residual connection pathway with non-linear functions in a block of a machine learning network.

More specifically, let the input to the p-th layer of a residual block as $x_p$, the output of the block $x_{p+1}$ has the form: $x_{p+1} = x_p + F(x_p, w_p)$; where $F(x_p, w_p)$ denotes the path with non-linear functions in the block (as shown in FIG. 33). If we stack the residual blocks, the last layer output $x_l$ can be expressed as: $x_l = x_p + \sum_{i=p}^{l-1} F(x_i, w_i)$. The residual connections enable direct information propagation from any residual block to another in both forward pass and back-propagation.

One interpretation of the residual network is that it behaves like an ensemble of relatively shallow networks. The unravelled view of the residual connections proposed by Veit et al. [78] suggests that the networks with n residual blocks have a collection of $2^n$ unique paths.

Figure 34:
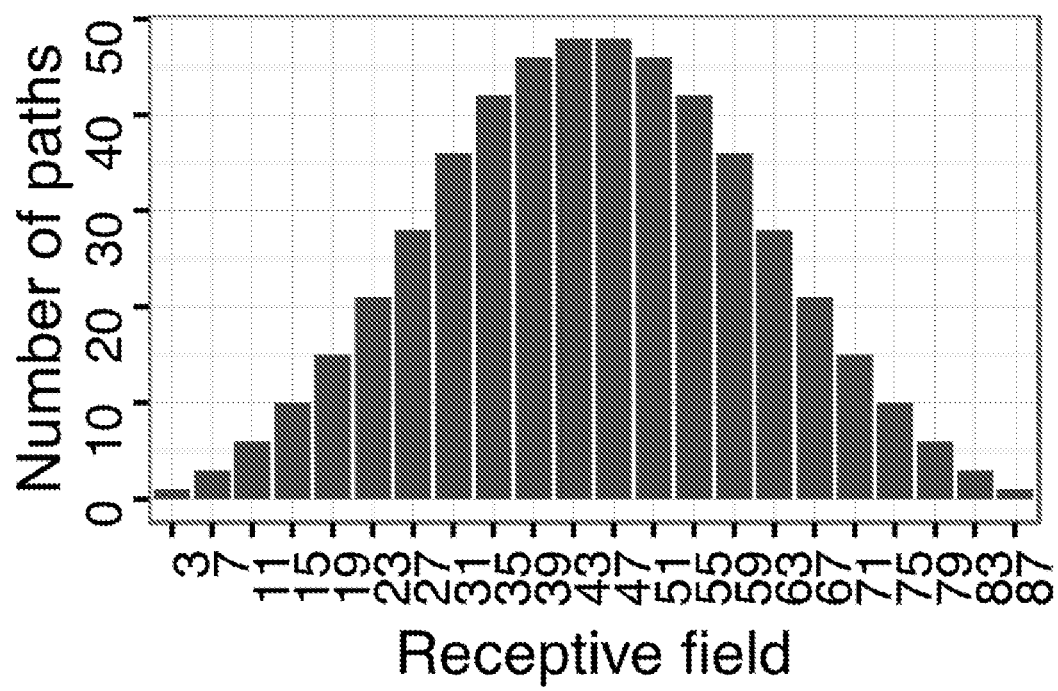
FIG. 34 is a graph showing the distribution of the number of receptive field of paths.

Without residual connections, the receptive field of a network is generally considered fixed. However, when training with n residual blocks, the networks utilise $2^n$ different paths and therefore features can be learned with a large range of different receptive fields. For example, the network proposed herein with 9 residual blocks has a maximum receptive field of 87×87×87 voxels. Following the unravelled view of the residual network, it therefore consists of $2^9$ unique paths. FIG. 34 shows the distribution of the receptive field of these paths. The receptive fields range from 3×3×3 to 87×87×87, following a binomial distribution.

This is different from the existing 3D networks. For example, the Deepmedic [14] model operates at two paths, with a fixed receptive field of 17×17×17 and 42×42×42 respectively. 3D U-net [18] has a relatively large receptive field of about 88×88×88 voxels, but there are only eight unique paths and receptive fields.

Intuitively, given that the receptive field of a deep convolutional network is relatively large, segmentation maps will suffer from distortions due to the border effects of convolution. That is, the segmentation results near the border of the output volume are less accurate due to the lack of input supporting window. Experiments are presented herein to demonstrate that the example networks generate only a small distortion near the borders. Training the example network with residual connections reduces the effective receptive field. The width of the distorted border is much smaller than the maximum receptive field. This phenomenon was also recently analysed by Luo et al. [79]. In practice, at test time we may pad each input volume with a border of zeros and discard the same amount of border in the segmentation output.

The last layer of an example network described herein may be a softmax (loss) function that gives scores over all labels for each voxel. Typically, an end-to-end training procedure minimises the cross entropy loss function using an N-voxel image volume $\{x_n\}_{n=1}^N$ and the training data of a C-class segmentation map $\{y_n\}_{n=1}^N$ where $y_n \in \{1, \ldots, C\}$ is: (20)
where $\delta$ corresponds to the Dirac delta function, and $F_c(x_n)$ is the softmax classification score of $x_n$ over the c-th class. However, when the training data are severely unbalanced (which is typical in medical image segmentation problems), this formulation leads to a strongly biased estimation towards the majority class. Instead of directly re-weighting each voxel by class frequencies, Milletari et al. [30] propose a solution by maximising the mean Dice coefficient directly, as per Equation 21 below, and this is the solution adopted herein.

$$\mathcal{D}(\{x_n\}, \{y_n\}) = \frac{1}{C} \sum_{c=1}^{C} \frac{2 \sum_{n=1}^{N} \delta(y_n = c) F_c(x_n)}{\sum_{n=1}^{N} [\delta(y_n = c)]^2 + \sum_{n=1}^{N} [F_c(x_n)]^2}. \quad (21)$$

Gal and Ghahramani demonstrated that the deep network trained with dropout can be cast as a Bayesian approximation of a Gaussian process [64]. Given a set of training data and their labels $\{X,Y\}$, training a network $F(\cdot,W)$ with dropout has the effect of approximating the posterior distribution $p(W|\{X,Y\})$ by minimising the Kullback-Leibler divergence term, i.e. $KL(q(W)\|p(W|\{X,Y\}))$; where $q(W)$ is an approximating distribution over the weight matrices W with their elements randomly set to zero according to Bernoulli random variables. After training the network, the predictive distribution of test data $\hat{x}$ can be expressed as $q(\hat{y}|\hat{x}) = \int F(\hat{x},W)q(W)dW$. The prediction can be approximated using Monte Carlo samples of the trained network:

$$\hat{y} = \frac{1}{M} \sum_{m=1}^{M} F(\hat{x}, W_m),$$

where $\{W_m\}_{m=1}^M$ is a set of M samples from $q(W)$. The uncertainty of the prediction can be estimated using the sample variance of the M samples.

With this theoretical insight, uncertainty of the segmentation map can be estimated at the voxel level. The segmentation network may be extended with a 1×1×1 convolutional layer before the last convolutional layer. The extended network is trained with a dropout ratio of 0.5 applied to the newly inserted layer. At test time, the network is sampled N times using dropout. The final segmentation can be obtained by majority voting. The percentage of samples which disagree with the voting results is typically computed at each voxel as the uncertainty estimate.

An example of a network structure for the approach described herein has 20 layers of convolutions. In the first seven convolutional layers, 3×3×3-voxel convolutions are adopted. These layers are designed to capture low-level image features such as edges and corners. In the subsequent convolutional layers, the kernels are dilated by a factor of two or four. These deeper layers with dilated kernels encode mid- and high-level image features. Residual connections are employed to group every two convolutional layers. Within each residual block, each convolutional layer is associated with an element-wise rectified linear unit (ReLU) layer and a batch normalisation layer [80]. The ReLU, batch normalisation, and convolutional layers are arranged in the pre-activation order [77].

Figure 35:
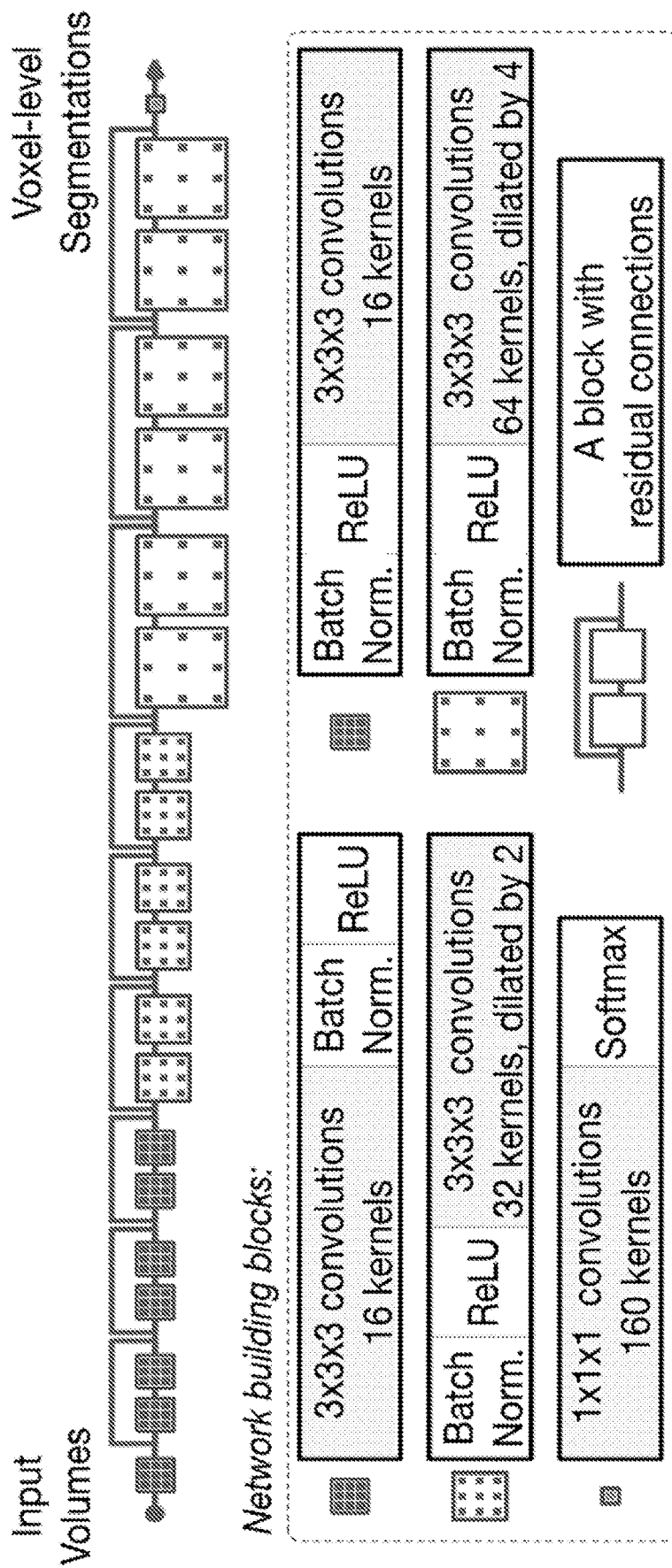
FIG. 35 is a schematic diagram of an example network architecture for volumetric image segmentation as described herein.

FIG. 35 shows an example of a network architecture for volumetric image segmentation. The network mainly utilises dilated convolutions and residual connections to make an end-to-end mapping from image volume to a voxel-level dense segmentation. To incorporate features at multiple scales, the dilation factor of the dilated convolutions is gradually increased as the layers go deeper. The residual blocks with identity mapping enable the direct fusion of features from different scales. The spatial resolution of the input volume is maintained throughout the network. The network can be trained end-to-end. In the training stage, the inputs to the specific example network are 96×96×96-voxel images. The final softmax layer gives classification scores over the class labels for each of the 96×96×96 voxels.

In the training stage, the pre-processing step is used for input data standardisation and augmentation at both image- and sub-volume-level. At image-level, we can adopt a simple pre-processing of the intensities as described above or use a histogram-based scale standardisation method [81] to normalise the intensity histograms. For data augmentation at image-level, randomisation can be introduced in the normalisation process, for example by randomly choosing a threshold of foreground between the volume minimum and mean intensity (at test time, the mean intensity of the test volume is used as the threshold). Each image can further be normalised to have zero mean and unit standard deviation. In the examples, augmentations on the randomly sampled 96×96×96 sub volumes were performed on the fly. These included rotation with a random angle in the range of [−10°,10°] for each of the three orthogonal planes and spatial rescaling with a random scaling factor in the range of [0.9,1.1].

All the parameters in the convolutional layers were initialised according to He et al. [26]. The scaling and shifting parameters in the batch normalisation layers were initialised to 1 and 0 respectively. The networks were trained with two Nvidia K80 GPUs. For each training iteration, each GPU processed one input volume; the average gradients computed over these two training volumes were used as the gradient updates. To make a fair comparison, the Adam optimisation method [82] was used for all the methods with fixed hyper-parameters. The learning rate lr was set to 0.01, the step size hyper-parameter $\beta_1$ was 0.9 and $\beta_2$ was 0.999 in all cases except V-Net, for which we chose the largest/lr for which the training algorithm converges (lr=0.0001). The models were trained until a plateau was observed in performance on the validation set. No additional spatial smoothing function (such as a conditional random field) was used as a post-processing step. Instead of aiming for better segmentation results by adding post-processing steps, the focus was on the dense segmentation maps generated by the networks. Networks without explicit spatial smoothing are potentially more reusable and can directly be embedded in the interactive segmentation workflows described above. All methods (including a re-implementation of Deepmedic [14], V-net [30], and 3D U-net [18] architecture) were implemented with Tensorflow (see https://www.tensorflow.org/).

To demonstrate the feasibility of learning complex 3D image representations from large-scale data, the network set to learn a highly granular segmentation of 543 T1-weighted MR images of healthy controls from the ADNI dataset (see http://adni.loni.usc.edu/). The average number of voxels of each volume is about 182×244×246 in the database. The average voxel size in the database is approximately 1.18 mm×1.05 mm×1.05 mm. All volumes are bias-corrected and reoriented to a standard Right-Anterior-Superior orientation. The bronze standard parcellation of 155 brain structures and 5 non-brain outer tissues are obtained using the GIF framework [83].

Figure 36:
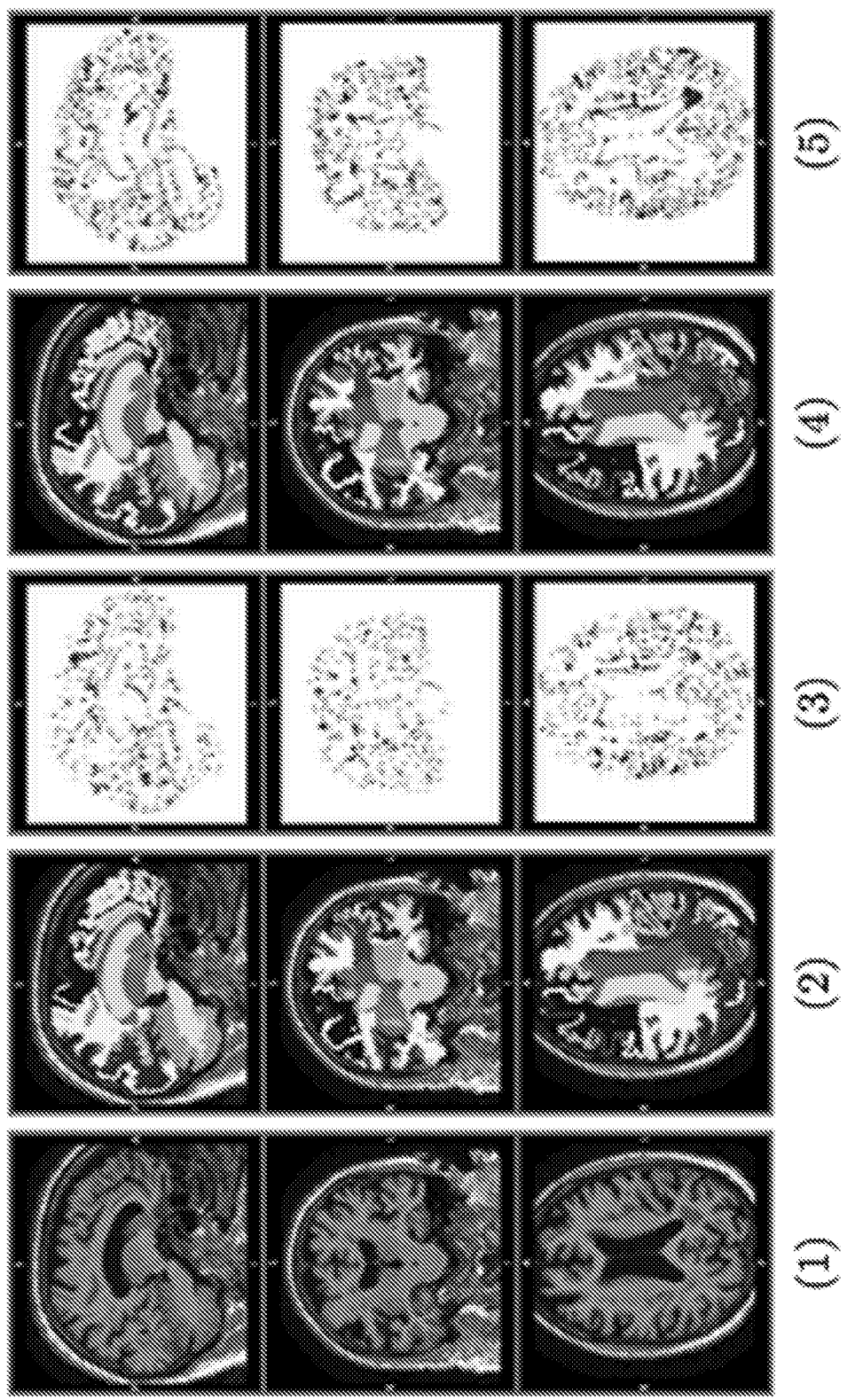
FIG. 36 shows visualisations of segmentation results of slices from a test image volume (column 1), segmentation maps and false prediction maps (columns 2 and 3; 4 and 5), generated by respectively by HC-dropout segmentation system described herein and 3D U-net-dice.
Figure 37:
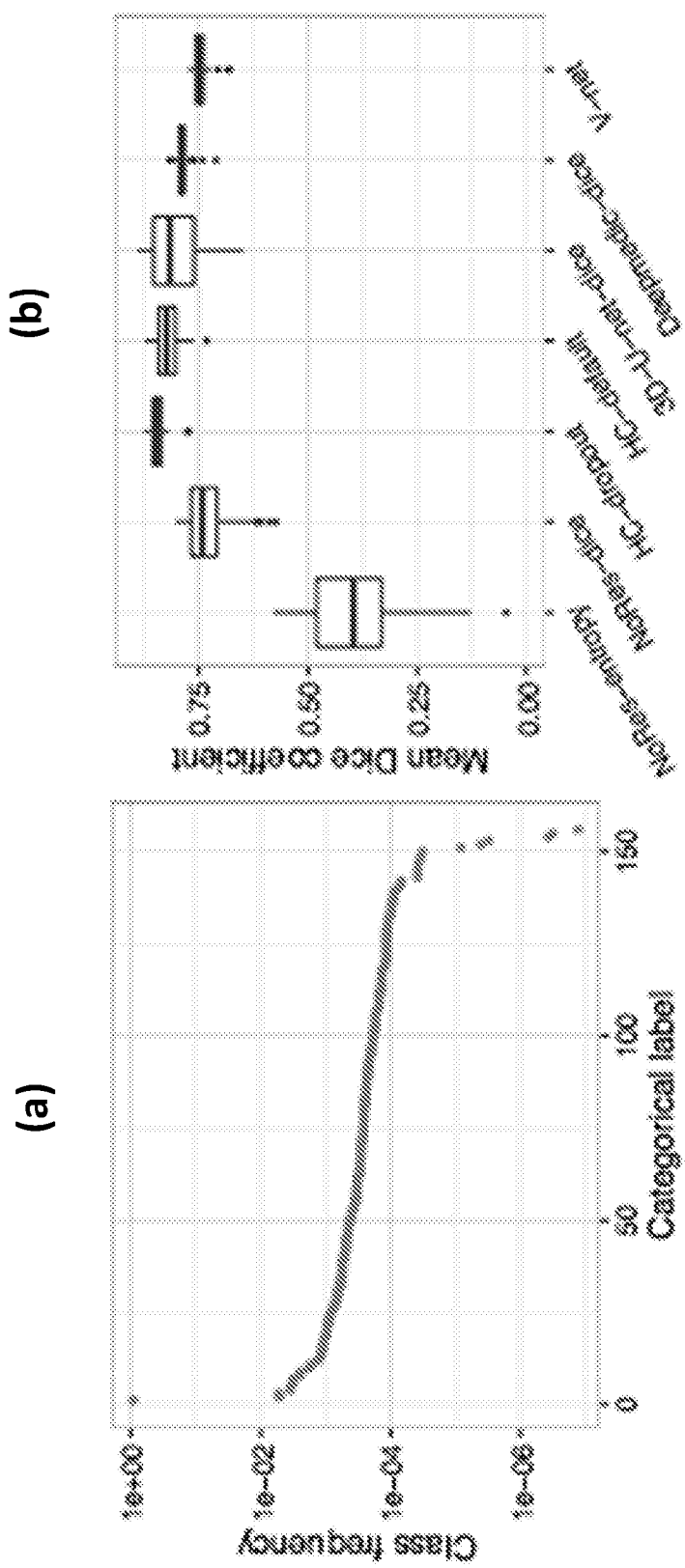

FIG. 36 shows visualisations of segmentation results, in particular: (1) slices from a test image volume, (2, 3) segmentation maps and false prediction maps generated by HC-dropout, and (4, 5) 3D U-net-dice (4, 5). FIG. 37a shows the label distribution of the dataset. We randomly choose 443, 50, and 50 volumes for training, test, and validation respectively.

The high-resolution compact network architecture described herein (as illustrated in FIG. 35; denoted as HC-default) is compared with three variants: (1) the HC-default configuration without the residual connections, trained with cross-entropy loss function (NoRes-entropy); (2) the HC-default configuration without residual connections, trained with Dice loss function (NoRes-dice); and (3) the HC-default configuration trained with an additional dropout layer, and making predictions with a majority voting of 10 Monte Carlo samples (HC-dropout). For the dropout variant, the dropout layer was employed before the last convolutional layer consists of 80 kernels.

Additionally, three state-of-the-art volumetric segmentation networks were evaluated, namely 3D U-net [18], V-net [30], and Deepmedic [14]. The last layer of each of these network architectures was replaced with a 160-way softmax classifier.

It was found that training these networks with the cross entropy loss function, as per Equation 20, generally leads to poor segmentation results. Since the cross-entropy loss function treats all training voxels equally, the network may have difficulties in learning representations related to the minority classes. Training with the Dice loss function alleviates this issue by implicitly re-weighting the voxels, so that all networks in this investigation were trained using the Dice loss function to provide a fair comparison.

The mean Dice Coefficient Similarity (DCS) was used as the performance measure for assessing the different approaches. Table 12 and FIG. 37b compare the performance of the different networks (different 3D convolutional network architectures) on the test set. In terms of the network variants, the results show that the use of the Dice loss function largely improves the segmentation performance, thereby suggesting that the Dice loss function can handle the severely unbalanced segmentation problem well. The results also suggest that introducing residual connections improves the segmentation performance measured in mean DCS, suggesting that the residual connections are important elements of the proposed network. By adopting the dropout method, the DCS can be further improved by 2% in DCS.

TABLE 12

| Architecture | Multi-layer fusion | Num. Par. | Loss type | DCS (%) | STD (%) |
|---|---|---|---|---|---|
| HC-default | Residual | 0.81 M | Dice loss | 82.05 | 2.96 |
| HC-dropout | Residual | 0.82 M | Dice loss | 84.34 | 1.89 |
| NoRes-entropy | N/A | 0.81 M | Cross entr. | 39.36 | 1.13 |
| NoRes-dice | N/A | 0.81 M | Dice loss | 75.47 | 2.97 |
| Deepmedic[11]-dice | Two pathways | 0.68 M | Dice loss | 78.74 | 1.72 |
| 3D U-net[3]-dice | Feature forwarding | 19.08 M | Dice loss | 80.18 | 6.18 |
| V-net[16] | Feature forwarding | 62.63 M | Dice loss | 74.58 | 1.86 |

Figure 38:
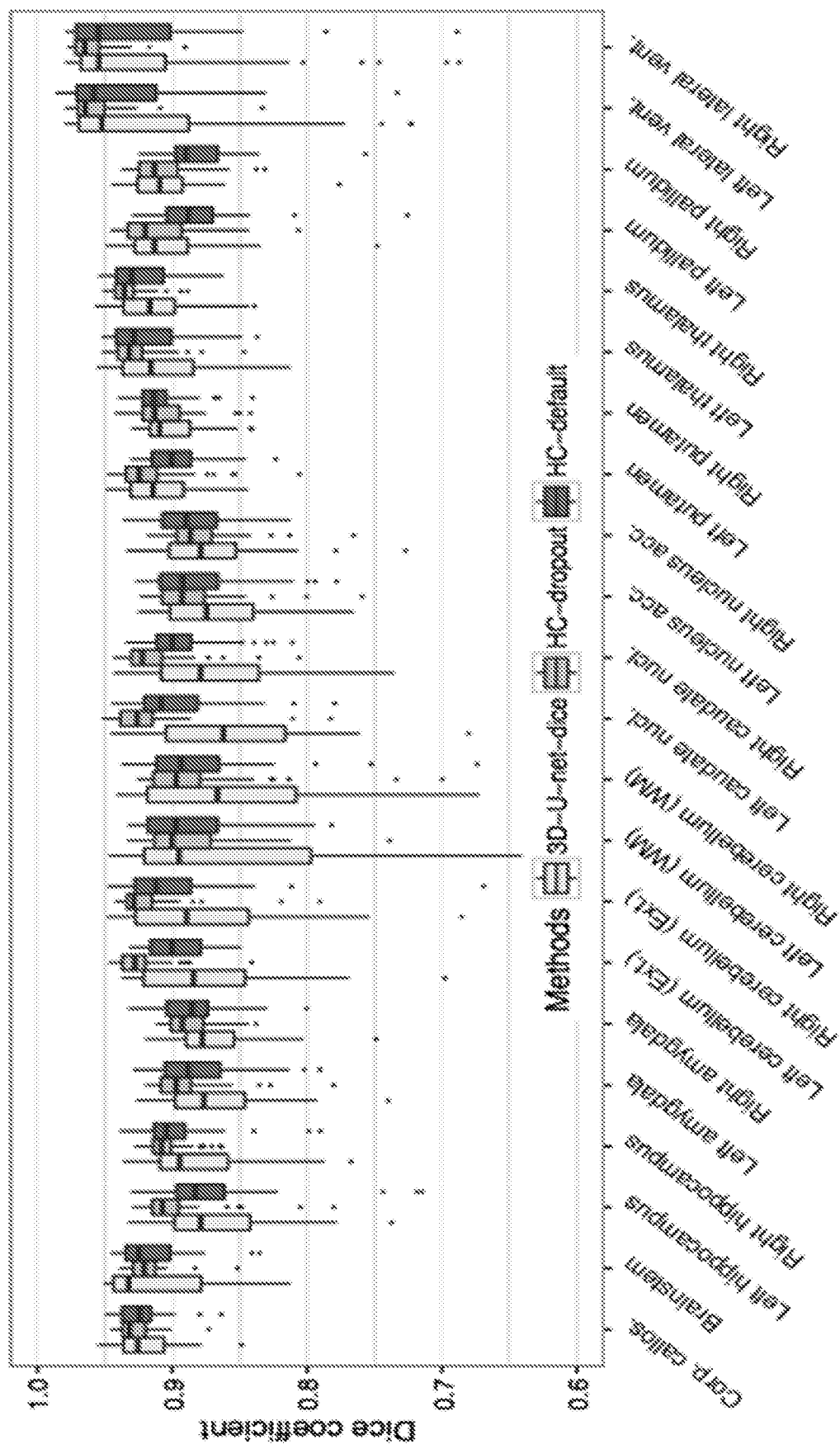
FIG. 38 show segmentation performance on a set of key structures in terms of Dice score (coefficient) for three different segmentation systems.

As can be seen from Table 12, with a relatively small number of parameters, HC-default and HC-dropout outperform the competing methods in terms of mean DCS. This suggests that network described herein is more effective for the brain parcellation problem Note that V-net has a similar architecture to 3D U-net and has more parameters, but does not employ the batch normalisation technique. The lower DCS produced by V-net suggests that batch normalisation is important for training the networks for brain parcellation. At a more detailed level, FIG. 38 shows that the dropout variant achieves better segmentation results for all the key structures within the brain (compared with HC-default and 3D U-net).

Figure 39:
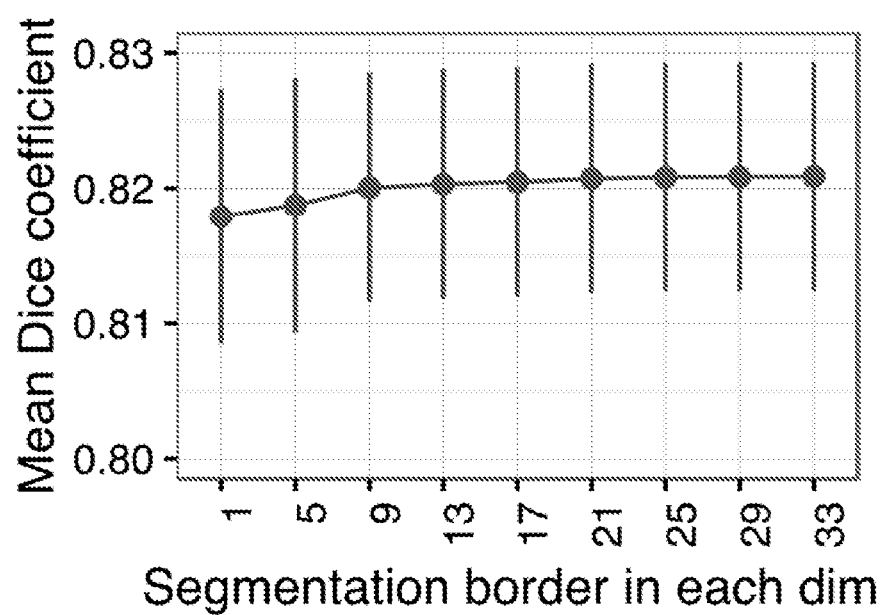
FIG. 39 plots the variation of Dice score, and standard error of segmentation, according to the size of the segmentation border.

A further investigation has been made of segmentation performance of a trained network when discarding the borders in each dimension of the segmentation map. That is, given a d×d×d-voxel input, at border size 1, we only preserve the $(d-2)^3$-voxel output volume centred within the predicted map. FIG. 39 plots the DCS and standard errors of segmentation according to the size of the segmentation borders in each dimension. The results show that the distorted border is around 17 voxels in each dimension. The border effects do not severely decrease the segmentation performance, but it is apparent that voxels near to the volume borders are classified less accurately. In practice, the volume images are padded with 16 zeros in each dimension, and the same size of border is then removed from the segmentation output.

Figure 40:
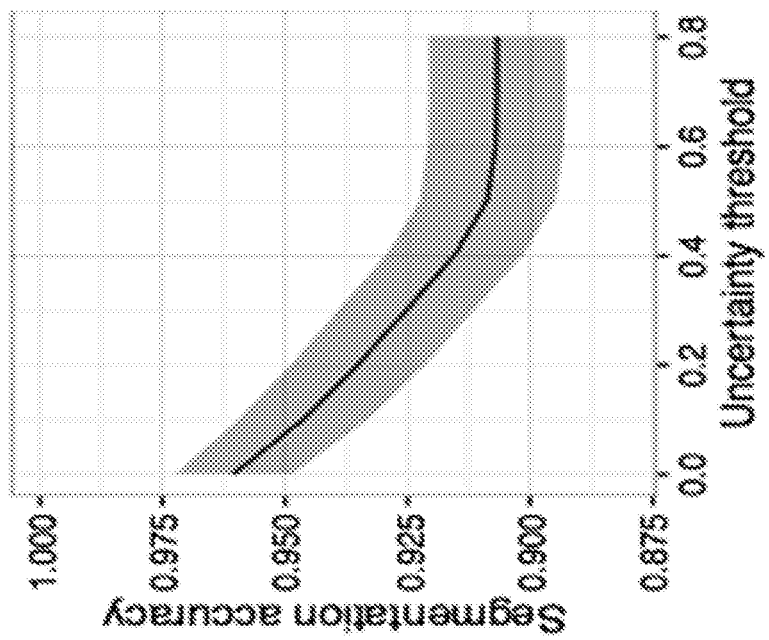
FIG. 40*a* plots the variation of segmentation performance, based on Dice score, against the number of Monte Carlo samples.
FIG. 40*b* plots the voxel-level segmentation accuracy against the uncertainty threshold.
Figure 40:
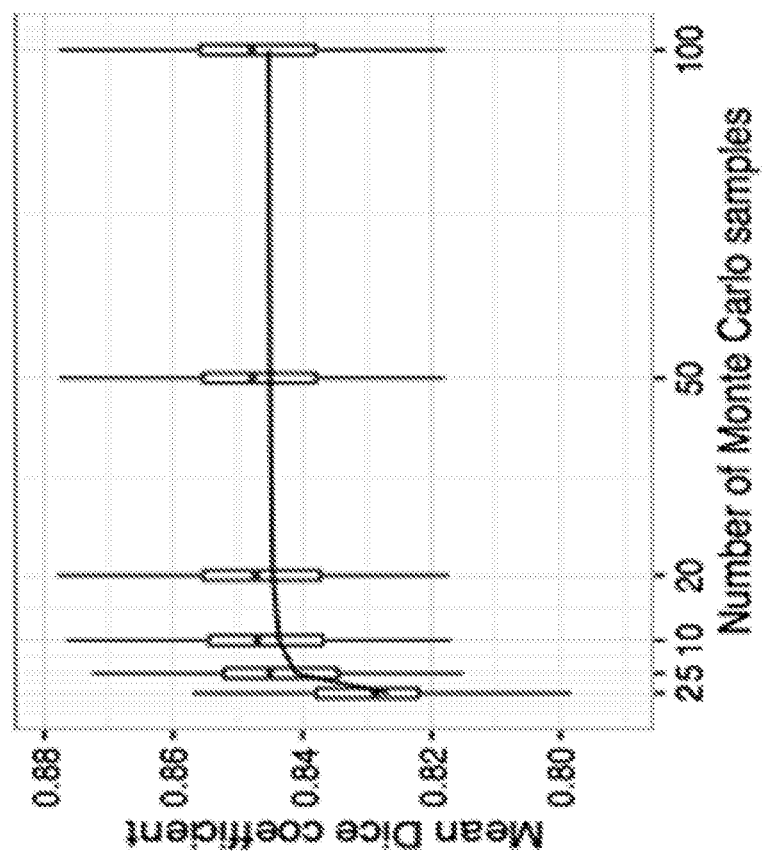

A further investigation was performed regarding the effect of the number of samples in uncertainty estimates—in particular, investigating the number of Monte Carlo samples and the segmentation performance of the network described herein. FIG. 40 shows an evaluation of dropout sampling, with FIG. 40a showing the segmentation performance against the number of Monte Carlo samples, and FIG. 40b showing the voxel-level segmentation accuracy by thresholding the uncertainties (the shaded area in FIG. 40b represents the standard errors.

FIG. 40a suggests that using 10 samples is enough to achieve good segmentation, and that further increasing the number of samples has a relatively small effect on the DCS. FIG. 40b plots the voxel-wise segmentation accuracy computed using only voxels with an uncertainty less than a threshold. The voxel-wise accuracy is high when the threshold is small. This indicates that the uncertainty estimation reflects the confidence of the network.

Figure 41:
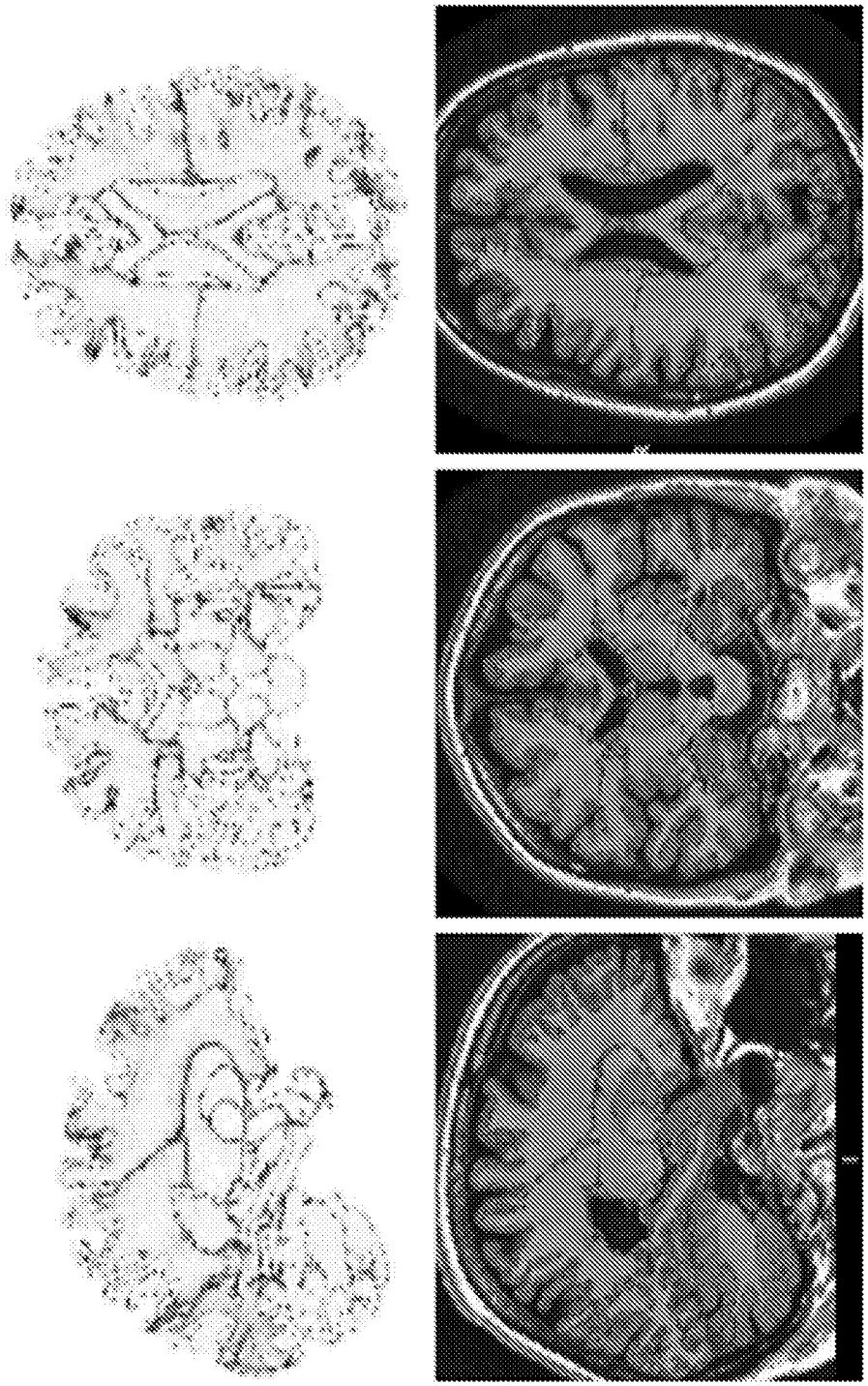
FIG. 41 shows voxel-level segmentation uncertainty estimations; the top row is a map generated from Monte Carlo simulations, the bottom row shows the uncertainty map thresholded at 0.1.

FIG. 41 shows voxel-level segmentation uncertainty estimations. The top row of FIG. 41 provides an uncertainty map generated with 100 Monte Carlo samples using dropout, while the bottom row represents an uncertainty map with a threshold at set at 0.1. It is clear from FIG. 41 that the uncertainties near the boundaries of different structures are relatively higher than the other regions. Note that displaying the segmentation uncertainty can be useful to a user, for example, in terms of the most effective locations for providing manual indications (e.g. clicks or scribbles) of the correct segmentation.

The approach described here takes about 60 seconds to predict a typical volume with 192×256×256 voxels (although this is timing likely to decrease as higher performance hardware become available). In some examples, to achieve better segmentation results and measure uncertainty, 10 Monte Carlo samples of our dropout model are required, in which case the overall process takes slightly more than 10 minutes in total. However, during the Monte Carlo sampling at test time, only the dropout layer and the final prediction layer are randomised. To further reduce computational time, future software could reuse features from the layers before dropout, resulting in only a slight increase in runtime compared with a single prediction.

A high-resolution, 3D convolutional network architecture has therefore been described that incorporates large volumetric context using dilated convolutions and residual connections. The resulting network is conceptually simpler and more compact than state-of-the-art volumetric segmentation networks. The resulting network has been validated using the challenging task of brain parcellation in MR images, and it is shown that the segmentation performance of this network compares favourably with the competing methods. Additionally, it is shown that the Monte Carlo sampling of a dropout technique can be used to generate voxel-level uncertainty estimation for the brain parcellation network. Moreover, the brain parcellation task described herein is regarded as a pretext task for volumetric image segmentation, and the resulting network potentially provides a good starting point for transfer learning of other segmentation tasks.

Section 4

Brain tumour segmentation plays a key role in computer-assisted surgery. Deep neural networks have increased the accuracy of automatic segmentation significantly, however these models tend to generalise poorly to different imaging modalities than those for which they have been designed, thereby limiting their applications, especially when considered in the context of interactive segmentation refinement. For example, the previous network architecture initially demonstrated for brain parcellation of monomodal T1 MRI cannot be easily translated into an efficient multimodal network that jointly utilises T1, c, Flair and T2 MRI for brain tumour segmentation. To tackle this problem, a scalable multimodal deep learning architecture is described herein that uses nested structures that explicitly leverage deep features within or across modalities. This helps to make the early layers of the architecture structured and sparse so that the final architecture becomes scalable to the number of modalities. The performance of the scalable architecture for brain tumour segmentation is investigated, including its regularisation effect compare to a conventional concatenation approach.

Reviewing in detail, gliomas are a common form of brain tumour, and make up 80% of all malignant brain tumours. Tumour-related tissue changes in the brain can be captured by various MR modalities, including T1, T1-contrast, T2, and Fluid Attenuation Inversion Recovery (FLAIR). Automatic segmentation of gliomas from MR images is an active field of research that promises to speed up diagnosis, surgery planning, and follow-up evaluations. Deep Convolutional Neural Networks (CNNs) have recently achieved state-of-the-art results for automatic tumour segmentation [13, 14]. Their success is partly attributed to their ability to automatically learn hierarchical visual features as opposed to conventional hand-crafted feature extraction.

Most existing multimodal network architectures handle imaging modalities by concatenating the intensities as an input. The multimodal information is implicitly fused by training the network discriminatively. Experiments show that relying on multiple MR modalities consistently is important for achieving highly accurate segmentations [89]. However, using classical modality concatenation to turn a given monomodal architecture into a multimodal CNN does not scale well because either it dramatically increases the number of hidden channels and network parameters, or it imposes a bottleneck on at least one of the network layers. This lack of scalability requires the design of dedicated multimodal architectures and makes it difficult and time-consuming to adapt state-of-the-art network architectures.

Recently, Havaei et al. [13] proposed a hetero-modal network architecture (HeMIS) that learns to embed different modalities into a common latent space. Their work suggests it is possible to impose more structure on the network. HeMIS separates the CNN into a backend that encodes modality-specific features up to the common latent space, and a frontend that uses high-level modality-agnostic feature abstractions. HeMIS is able to deal with missing modalities and shows promising segmentation results. However, the adaptation of existing networks to additional imaging modalities is not considered, likewise an optimal fusion of information across modalities is not demonstrated.

The present approach utilises a scalable network framework (ScaleNets) for adapting an existing architecture to an arbitrary number of MR modalities, instead of building a new architecture from scratch. ScaleNets separates a given network into a backend and frontend with across-modality information flowing through the backend, thereby alleviating the need for a one-shot latent space merging. The proposed scalable backend takes advantage of a factorisation of the feature space into imaging modalities (M space) and modality-conditioned features (F space). By explicitly using this factorisation, sparsity is imposed on the network structure with demonstrated improved generalisation.

The framework is evaluated by starting from a high-resolution network initially designed for brain parcellation from T1 MRI [71], and readily adapting it to brain tumour segmentation from T1, T1c, Flair and T2 MRI. The design of the modality-dependent backend is also considered by comparing several important factors, including the number of modality-dependent layers, the merging function, and convolutional kernel sizes. These experiments show that the proposed networks are more efficient and scalable than the conventional CNNs and achieve competitive segmentation results on the BraTS 2013 challenge dataset.

Concatenating multimodal images as input is the simplest and most common approach in CNN-based segmentation [14, 13]. The complete feature space FM can be factorised into an M-features space, M, derived from imaging modalities, and an F-features space, F, derived from scan intensity. However, conventional concatenation does not take advantage of this potential factorisation. In contrast, the approach described herein imposes structural constraints to make the factorisation explicit. At each layer, we denote the data as belonging to the set of maps $G(V \times F \times M) = \{x: V \times F \times M \to R\}$, where $V = R^{N1 \times N2 \times N3}$ is the set of voxel coordinates. This factorisation allows us to introduce new scalable layers that perform the transformation (f') of the joint FM feature space in two steps: f typically uses convolutions across F-features and g across M-features. This can be considered as replacing:
$G(V \times F \times M)$ f'$\to$(v$\times$F'$\times$M') with the combination of;
$G(V \times F \times M)$ f$\to G(v \times F' \times M)$ followed by $G(V \times F' \times M)$ g$\to G$(v$\times$F'$\times$M')

Figure 42:
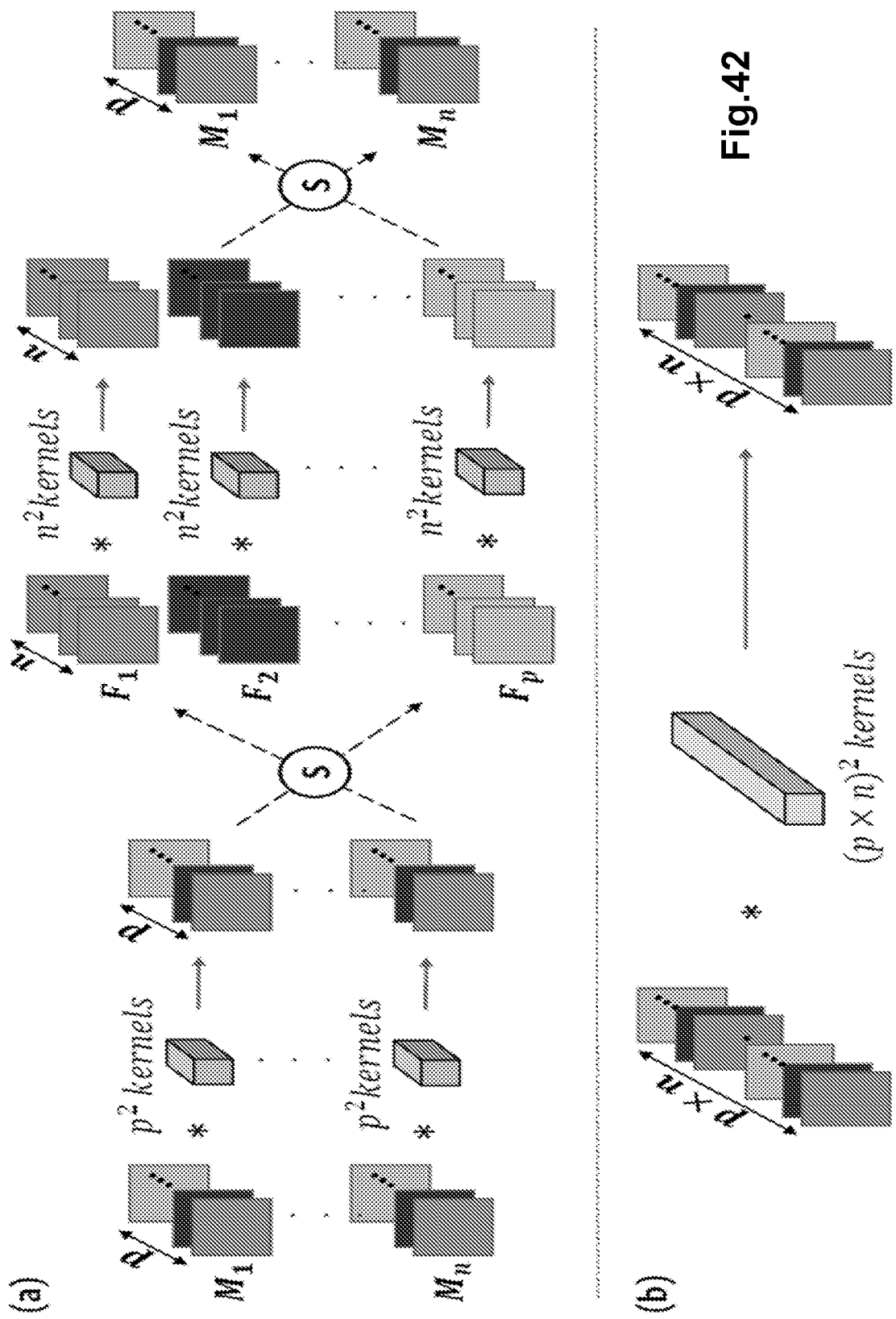
FIG. 42*a* (top) is a schematic diagram of a segmentation system having a scalable multimodal layer, compared with a classical CNN layer having multimodal images concatenated as input as shown in FIG. 42*b* (bottom).

By way of example, FIG. 42 shows (a) the proposed scalable multimodal layer, and (b) a classic CNN layer with multimodal images concatenated as input. For clarity we represent 2D nodes and assume the number p of F-features and the number n of M-features are constant. Restricting kernels to separate F-kernels and M-kernels is sparser and more modular than using joint FM-kernels. The ratio of number of parameters in (a) compared to (b) is (p+n)/(p×n). The example layer architecture of FIG. 42 therefore offers several advantages compared to a conventional architecture, including: (1) cross F-feature layers remain to some extent independent of the number of modalities; (2) cross M-feature layers allow the different modality branches to share complementary information; and (3) the total number of parameters is reduced. Note that the HeMIS architecture [68], in which one branch per modality is maintained during several layers before averaging all of them, has some similarities to our framework in the case where the cross modalities transformations are identity mappings.

Another important component of the framework described herein is the merging layer. Typical choices in the literature [71] include: (1) concatenation, (2) averaging, and (3) maxout. We are not aware that an explicit comparison of these different methods for multimodal CNNs has previously been addressed. With concatenation, all the information is maintained but the structure is lost, $$G(V \times F \times M) \xrightarrow{concat} G(V \times F M)$$

whereas with averaging or maxout, the output M dimension (typically 1) is independent from the number of incoming modalities (i.e. branches), $$G(V \times F \times M) \xrightarrow{\phi} G(V \times F \times 1)$$

It is worth noting that, as opposed to concatenation, relying on averaging or maxout for the merging layer at the interface between a backend and frontend makes the frontend structurally independent of the number of modalities and more generally of the entire backend. The ScaleNets as described here utilises such a merging strategy to offer scalability in the network design.

Figure 43:
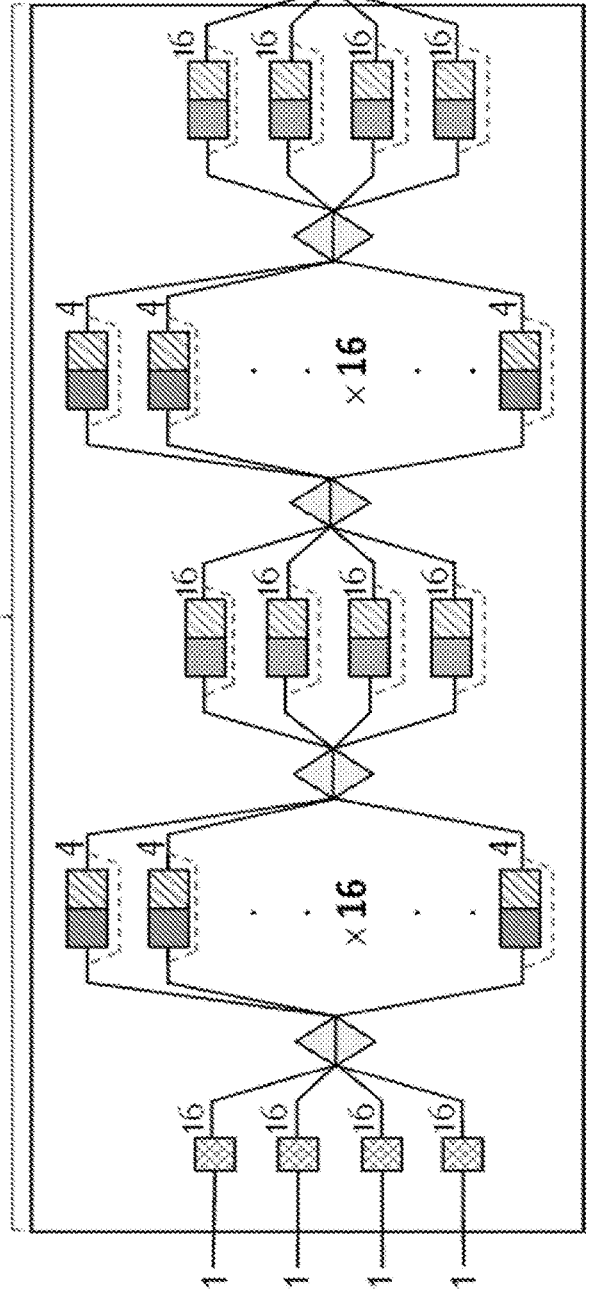
FIG. 43 is a schematic diagram comparing two a scalable architectures (top and middle) and a classic CNN architecture.
Figure 43:
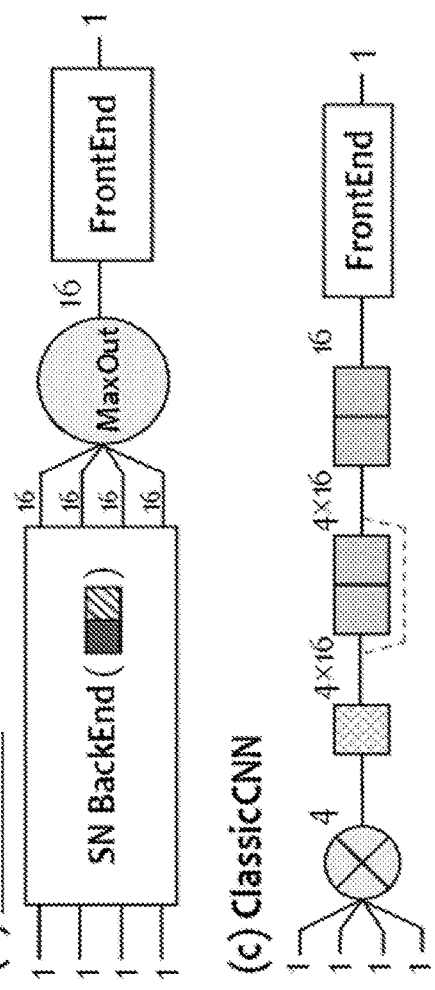
Figure 43:
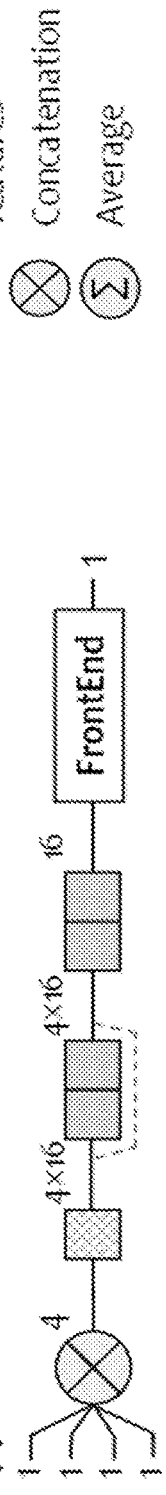
Figure 43:
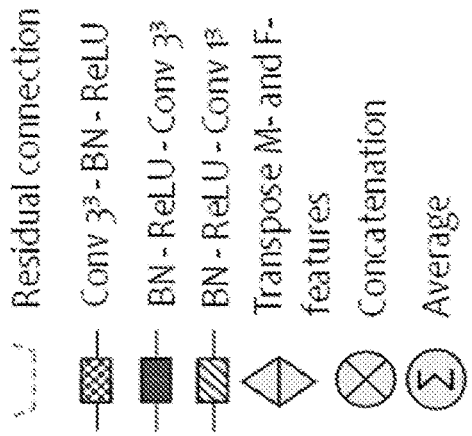

To demonstrate that a scalable framework can provide, to a deep network, the flexibility of being efficiently reused for different sets of image modalities, we adapt a model originally built for another task, such brain parcellation from T1 MRI, as described above. As shown in FIG. 43, ScaleNets splits the network into two parts: (i) a backend and (ii) a frontend. (Note that FIG. 43 shows both Scalable and Classic CNN architectures; numbers in bold are for the number of branches and the other numbering corresponds to the number of features. In the following example implementations, different backend architectures are explored for scaling a monomodal network into a multimodal network. A merging operation is added to allow any backend to plug into the frontend, and so makes the frontend independent of the number of modalities used (as a result, the frontend may be the same for all our architectures). Note that the example scalable models (SN31Ave1, SN31Ave2, SN31Ave3, SN33Ave2, SN31Max2), such as shown in FIG. 43, are named consistently, whereby SN31Ave2 (for example) stands for: "ScaleNet with 2 cross M-features residual blocks with $3^3$ convolutions and $1^3$ convolutions before averaging" (as shown in FIG. 43a).

The baseline monomodal architecture used for comparison in the experiments is a high-resolution, compact network designed for volumetric image segmentation [71], which has been shown above to provide state-of-the-art results for brain parcellation of T1 scans. This network makes an end-to-end mapping from a monomodal image volume to a voxel-level segmentation map mainly with convolutional blocks and residual connections. To incorporate image features at multiple scales while maintaining the spatial resolution of the input images, the convolutional kernels are gradually dilated with a factor of two and four through the network. The maximum receptive field is 87×87×87 voxels and is therefore able to catch multi-scale information in one path. The residual connections, by passing the gradient unchanged, allow all the layers of the network to train equally, which is helpful for our experiments, in which we compare architectures that differ for the first layers only.

For brain tumour segmentation, we have compared the different models on the challenging task of brain tumour segmentation using the BraTS 2015 training set that is composed of 274 multimodal images (T1, T1c, T2 and Flair)

(see http://braintumorsegmentation.org/). We divide the training set into 80% for training, 10% for validation and 10% for testing. (Validation is used during the training stage: for example, in every N iterations of training, the validation data is used to measure the performance of the network so that we can know if the network over-fits the training set or not; testing data is used after the entire training stage for evaluation). The Challenge BraTS 2013 dataset, for which an online evaluation platform is available, is used to compare an example implementation of our basic scalable network model to state-of-the-art.

In the example, we maximise the soft Dice score as proposed by [30] and described above. All networks are trained with the Adam Optimization method [82] where the learning rate was set to lr=0.01, and the other parameters $\beta 1=0.9$ and $\beta 2=0.999$. We also used early stopping on the validation set. Rotations of random small angles in the range [−10°,10°] are applied along each axis during training. All the scans of BraTS dataset are available after skull stripping, resampling to a 1 mm isotropic grid and co-registration of all the modalities to the T1-weighted images for each patient. Additional pre-processing and post-processing steps were kept as minimal as possible and reduced to merely normalising all individual image intensities to zero mean and unit variance. No bias field correction was applied. The experiments were performed using TensorFlow r0.11 and one GPU Nvidia GTX Titan.

Results were evaluated using the Dice score for different tumour subparts: whole tumour, core tumour and enhanced tumour. Additionally, we introduced a healthy tissue class to be separated from the background (zeroed out in the BraTS dataset). For the Challenge datasets, the evaluation was performed using the online validation platform (https://www.virtualskeleton.ch/BraTS/).

To demonstrate the potential benefit of the example framework, two ScaleNets implementations were compared with a classic CNN. Table 13 highlights the benefits of ScaleNets in terms of number of parameters.

Nets compared to classic CNNs. In addition, we note that SN31Ave2 outperforms SN31Max2 for the core tumour, and provides similar results on whole tumour and enhanced tumour.

Figure 45:
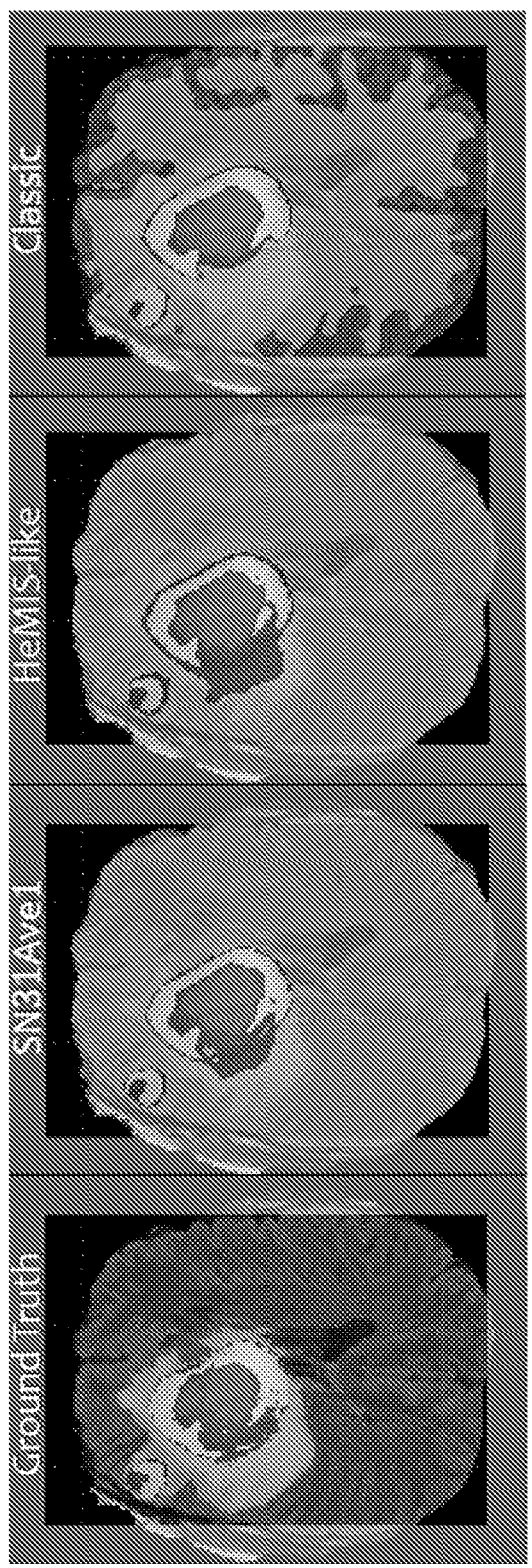
FIG. 45 shows qualitative comparison of various parcellation systems (ScaleNets variants) and a classic CNN on a particular test case.

Intuitively, the different modality branches should be merged when the F-features reach a sufficient degree of abstraction to become modality-agnostic. We compare ScaleNets with 1, 2 or 3 cross-modality residual blocks before averaging (respectively identified as "SN31Ave1", "SN31Ave2", "SN31Ave3"). The results given in FIG. 45 show a similar performance for all of these models. This suggests that for T1, T1c, FLAIR and T2, a short backend is enough to get a modality-agnostic sufficient representation for the segmentation of gliomas. It is also noted that SN31Ave1 outperforms Classic CNN on all tumour regions ($p \leq 0.001$).

Figure 44:
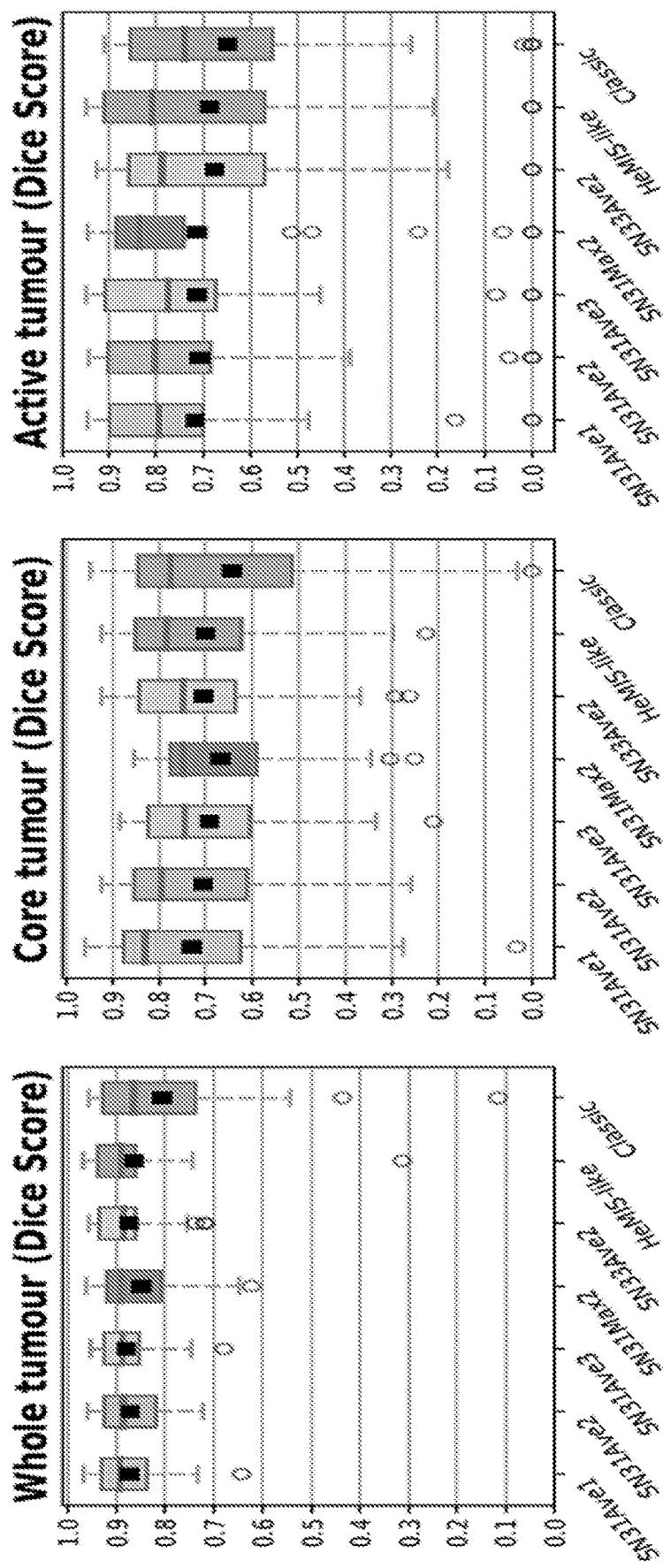
FIG. 44 shows a comparison of various parcellation systems (ScaleNets variants) and a classic CNN as used on a test set after early stopping.

The usefulness of the cross M-feature layers was validated by comparing our network to an implementation of ScaleNets which was aimed at replicating the characteristics of the HeMIS network [66] by removing the cross M-feature layers. We refer to this latest network as HeMIS-like, and the Dice score results in FIG. 44 illustrate improved performance on the core tumour ($p \leq 0.03$) and similar performance on the whole and active tumour (this finding is also confirmed by the qualitative comparison of FIG. 45).

To compare to state-of-the-art results, we used the less complex of the more accurate models, SN31Ave1. The results obtained by this system on the Leaderboard and Challenge BraTS 2013 dataset are reported in Table 14 in comparison with the BraTS 2013 Challenge Winners. It can be seen that the present approach achieves similar results while using a very "cheap" pipeline with minimal pre-processing and no post-processing.

TABLE 13

Sizes of the compared CNN models.

| | Model | | | | | |
|---|---|---|---|---|---|---|
| SN31Ave1 | SN31Ave2 | SN31Ave3 | SN33Ave2 | SN31Max2 | HeMIS-like | Classic |
| # Param. 0.83M | 0.85M | 0.88M | 0.92M | 0.85M | 0.89M | 1.15M |

In addition, two different merging strategies were compared (averaging: "SN31Ave2" and maxout: "SN31Max2") with a "Classic" CNN architecture, which can be seen as a merging operation by concatenating the available modalities before the first convolutional layer. To be as fair as possible, the kernel sizes were chosen so that the maximum receptive field remains the same across all architectures.

FIG. 44 shows a comparison of various ScaleNets implementations and a Classic CNN on the testing set after early stopping. Quantitative Dice scores show that both SN31Ave2 and SN31Max2 outperform Classic CNN on active tumour region segmentation ($p \leq 0.001$). FIG. 45 shows a qualitative comparison of different models output on a particular test case. Colours correspond to different tissue regions. red: necrotic core, yellow: enhancing tumour, blue: non-enhancing tumour, green: edema, cyan: healthy tissue. These qualitative results in the test case with strong artefact deformation demonstrate the robustness of Scale-

TABLE 14

| | Leaderboard | | | Challenge | | |
|---|---|---|---|---|---|---|
| Method | Whole | Core | Enhanced | Whole | Core | Enhanced |
| Tustison | 79 | 65 | 53 | 87 | 78 | 74 |
| Zaho | 79 | 59 | 47 | 84 | 70 | 65 |
| Meier | 72 | 60 | 53 | 82 | 73 | 69 |
| SN31Ave1 | 78 | 58 | 52 | 88 | 73 | 68 |

In summary, a scalable deep learning framework has been provided that allows the building of more reusable and efficient deep models when multiple correlated sources are available. In the case of volumetric multimodal MRI for brain tumour segmentation, several example scalable CNNs are described that integrate smoothly the complementary information about tumour tissues scattered across different imaging modalities. The various implementations of Scale-Nets impose a sparse structure to the backend of the architecture, in which cross features and cross modalities transformations are separated. ScaleNets has some similiarities to the recently proposed implicit Conditional Networks [68] and Deep Rooted Networks [67] that use sparsely connected architecture (but these other systems do not suggest the transposition of branches and grouped features). Both of these frameworks have been shown to improve the computational efficiency of state-of-the-art CNNs by reducing the number of parameters, the amount of computation and increasing the parallelisation of the convolutions.

Using the scalable layer architecture described herein, a compact network for brain parcellation of monomodal T1 has been readily adapted into a multimodal network for brain tumour segmentation with 4 different image modalities as input. Scalable structures, thanks to their sparsity, have a regularisation effect. A comparison of classic and scalable CNNs shows that scalable networks are easier to train and use fewer parameters while maintaining similar or better accuracy for medical image segmentation. The scalable network structures described herein have the potential to improve re-usability for deep networks for segmenting medical images, and help support efficient transfer learning in volumetric MRI analysis.

Section 5

The present application provides a number of computer-implemented methods for segmenting an input image, including: generating a first segmentation of the input image using a first machine learning system, the first segmentation comprising multiple segments; receiving, from a user, at least one indication, wherein each indication corresponds to a particular segment from the multiple segments, and indicates one or more locations of the input image as belonging to that particular segment; constructing, for each segment of the multiple segments having at least one corresponding indication, a respective geodesic distance map, based on the input image and the user indications received for that segment; and generating a second segmentation using a second machine learning system based on the input image and the constructed geodesic distance maps.

This method provides an efficient and accurate segmentation method, especially in terms of reducing user interactions (providing the indications).

A further computer-implemented method for segmenting an input image comprises receiving an input image into a machine learning system for performing segmentation of the image based on a set of model parameters, the machine learning system having been trained using a previous set of training images provided with labelled segmentations, wherein the input image is received without a labelled segmentation; and performing a segmentation of the input image into multiple segments by solving jointly for: (i) a segmentation of the input image; and (ii) an updated set of model parameters for the machine learning system, whereby the machine learning system is tuned by the input image.

This method provides a segmentation method that allows the model parameters to be further updated (enhanced) after the training period has completed, i.e. without using additional fully annotated images. In some cases this updating is performed on the basis of user interactions, such as providing indications of a correct segmentation for parts of the image. However, the model made also be updated in an unsupervised manner, in an automated manner as part of the segmentation process.

A further computer-implemented method for segmenting an input image comprises: receiving an input image into the machine learning system comprising multiple imaging modalities (M-space) and generating multiple modality-conditioned features (F-space); and processing the input image by performing a first transform within one or more layers of the machine learning system across F-space and a second transform within one or more further layers of the machine learning system across M-space to perform the segmentation.

This factorisation by modality and feature space has been found to help provide a more effective machine learning system for image segmentation of multimodal images.

In some implementations, the machine learning system comprises a back-end which processes the input image by performing said first and second transforms, and which merges (e.g. averages) the output from said first and second transforms across M-space; and a front-end which receives the back-end merged or averaged output and generates therefrom a segmentation of the input image based on a monomodal (like) analysis.

This architecture allows multi-modal images to be accommodated by the back-end, which can then be integrated with a mono-modal front end so as to be able to exploit a variety of existing mono-modal machine learning systems.

In general, the methods described herein can be performed with respect to a wide variety of images, of any appropriate dimensionality, modality, etc. Although the examples are described above relate to the segmentation or parcellation of medical images, the methods potentially apply to any other suitable form of image, e.g. identifying features, such as buildings, crops, terrain, habitat, etc on geographical (satellite) images.

Although the methods described above in sections 1-4 have been presented separately from one another, it will be understood that the methods (or parts thereof) may be used in conjunction with one another. For example, the architecture of section 4 could be utilised in the approach of section 1 or section 2 to support multi-modal imaging. Likewise, the use of residual connections as described in section 3 might be used in the approach of section 1, 2 or 3 to enhance segmentation performance. In addition, the use of a bounding box on the input image, as per section 2, might also be utilised for the approach of section 1, 3 or 4. Accordingly, features from different sections and implementations may be combined as appropriate unless otherwise indicated.

Figure 46:
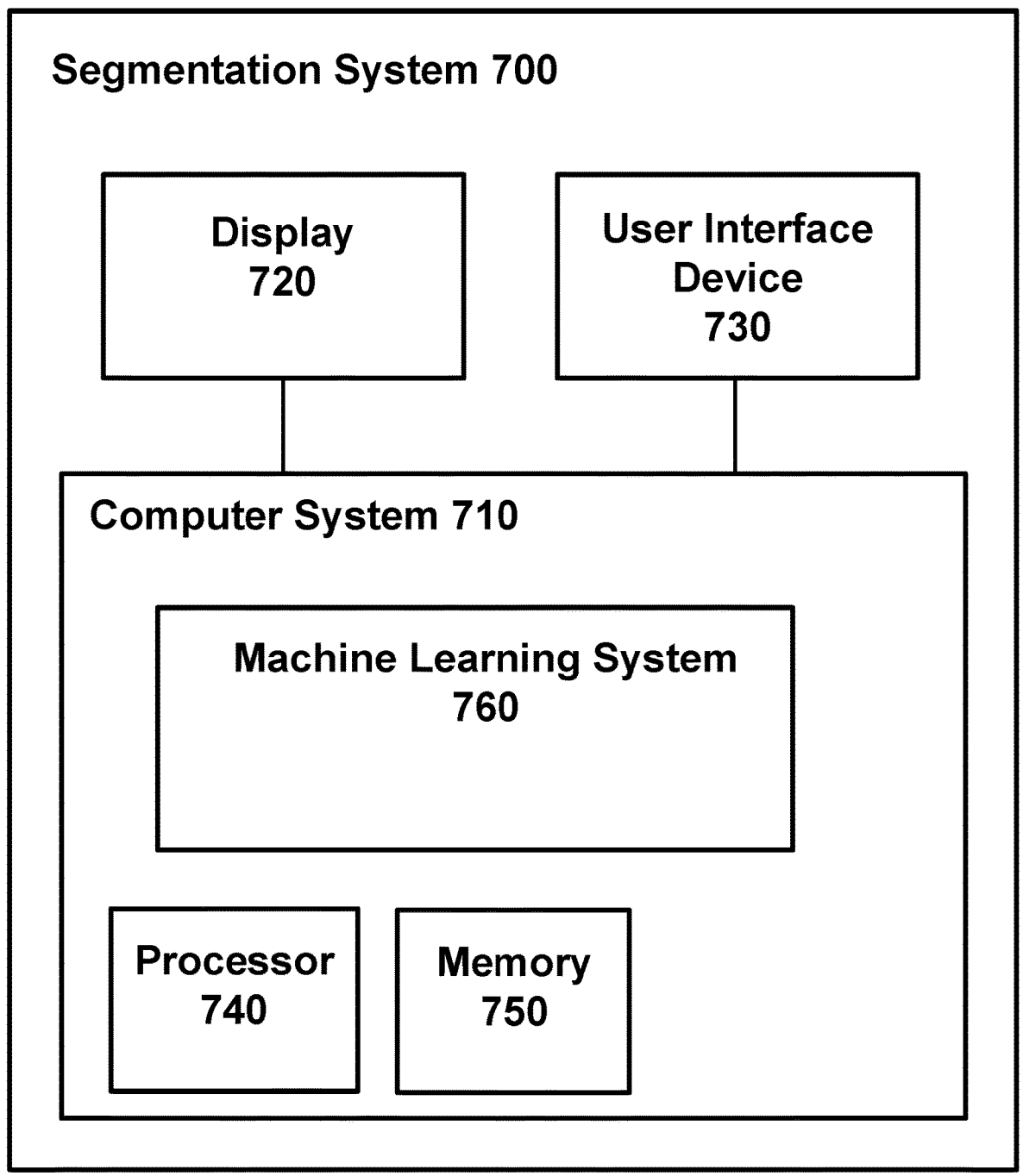
FIG. 46 is a high-level schematic architecture of a segmentation system such as described herein.

FIG. 46 shows an example of a segmentation system 700 for implementing the methods described herein. The segmentation system includes a computer system 710 with a display 720 and user interface device 730 e.g. one or more of a keyboard, mouse, etc. In some cases the display may be a touch-screen and hence itself act as a user interface device 730. The computer system 710 includes at least one processor 740 and memory 750 for storing program instructions for execution by the processor 740. The skilled person will be aware that the computer system 710 may include other components not shown in FIG. 46, such as a network connection, storage (disk or semiconductor), etc.

The computer system 710 includes a machine learning system 760 for performing the segmentation. The machine learning system 760 may comprise one or more neural networks as described herein, but could also be based on one or more other forms of machine learning, such as random forests. The machine learning system 760 is typically implemented as program instructions for execution by processor 740, but some or all of the machine learning system may be implemented using specialised hardware. In some cases the segmentation system 700 may be implemented using a general purpose computer system 710, in other cases the segmentation system may be incorporated into more specialised equipment, such as an MR imaging system.

Although FIG. 46 shows the segmentation system 700 as a standalone system, in other cases it may be implemented as a distributed system, for example, with some processing performed locally, and other processing performed remotely (e.g. in the cloud). Overall, it will be appreciated that the segmentation system 700 is provided only be way of example, and other architectures will be apparent to the skilled person.

Figure 47:
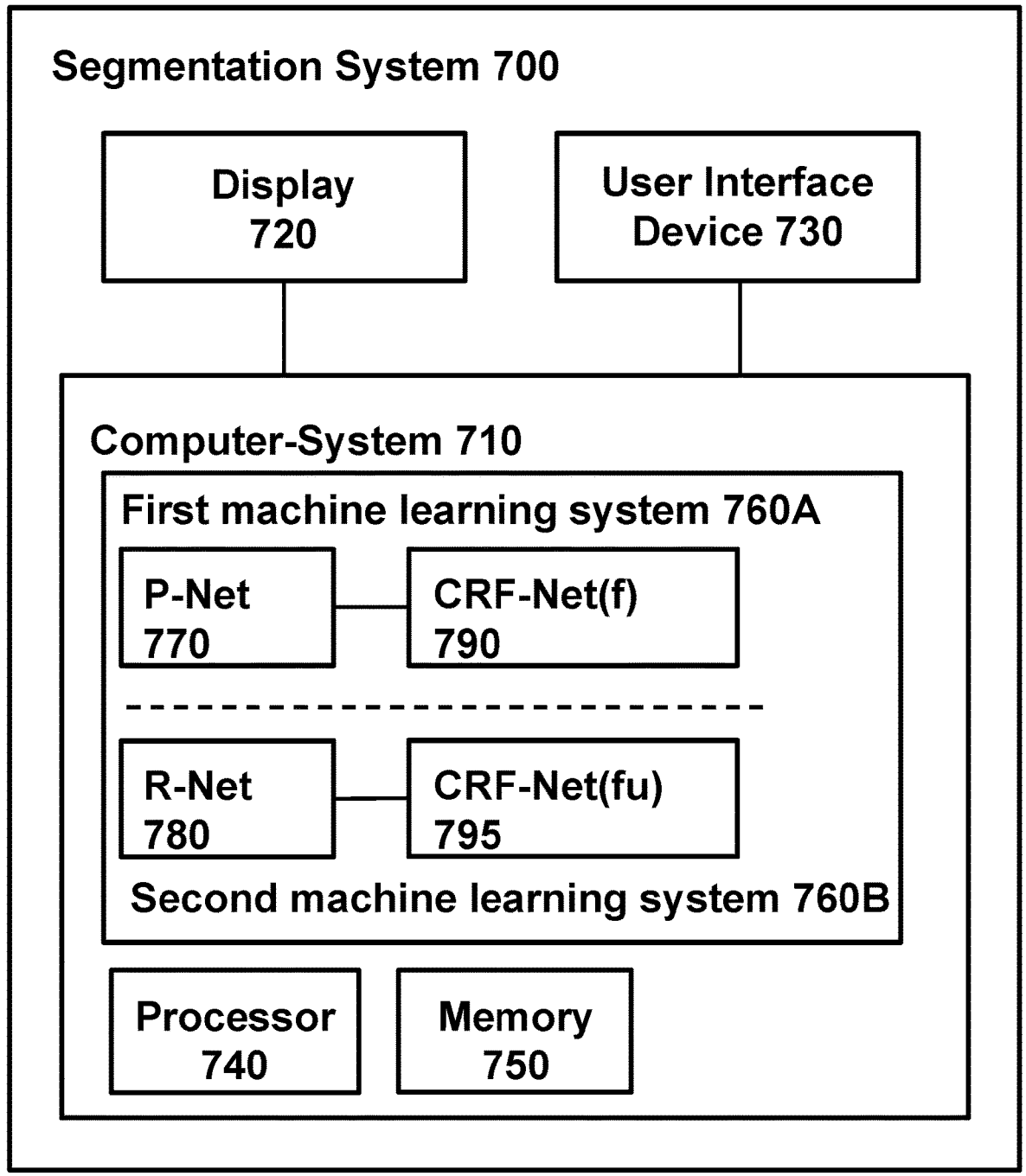
FIG. 47 is a schematic architecture of a segmentation system such as described in section 1 below.

Further by way of illustration, FIG. 47 shows an example of the structure of a segmentation system 700 for implementing the approach of section 1 above. In this case the computer system 710 supports a first machine learning system 760A and a second machine learning system 760B. The first machine learning system 760A comprises a CNN, denoted as P-Net 770, in conjunction with a conditional random field, denoted as CRF-Net(f) 790. The second machine learning system 760B comprises a CNN, denoted as R-Net 780, in conjunction with a conditional random field, denoted as CRF-Net(fu) 795.

In conclusion, it will be appreciated that the various implementations described herein are provided by way of example only, and the skilled person will be aware of potential modifications and adaptions dependent on any particular set of circumstances. Accordingly, the present invention is to be defined by the appended claims and their equivalents.

REFERENCES

[1] N. Sharma and L. M. Aggarwal, "Automated medical image segmentation techniques." Journal of medical physics, vol. 35, no. 1, pp. 3-14, 2010.

[2] F. Zhao and X. Xie, "An Overview of Interactive Medical Image Segmentation," Annals of the BMVA, vol. 2013, no. 7, pp. 1-22, 2013.

[3] Y. Boykov and M.-P. Jolly, "Interactive Graph Cuts for Optimal Boundary & Region Segmentation of Objects in N-D Images," in ICCV, 2001, pp. 105-112.

[4] C. Xu and J. L. Prince, "Snakes, Shapes, and Gradient Vector Flow," TIP, vol. 7, no. 3, pp. 359-369, 1998.

[5] L. Grady, "Random walks for image segmentation," PAMI, vol. 28, no. 11, pp. 1768-1783, 2006.

[6] A. Criminisi, T. Sharp, and A. Blake, "GeoS: Geodesic Image Segmentation," in ECCV, 2008.

[7] C. Rother, V. Kolmogorov, and A. Blake, "'GrabCut': Interactive Foreground Extraction Using Iterated Graph Cuts," ACM Trans. on Graphics, vol. 23, no. 3, pp. 309-314, 2004.

[8] G. Wang, M. A. Zuluaga, R. Pratt, M. Aertsen, T. Doel, M. Klusmann, A. L. David, J. Deprest, T. Vercauteren, and S. Ourselin, "Slic-Seg: A minimally interactive segmentation of the placenta from sparse and motion-corrupted fetal MRI in multiple views," Medical Image Analysis, vol. 34, pp. 137-147, 2016.

[9] B. Wang, W. Liu, M. Prastawa, A. Irimia, P. M. Vespa, J. D. V. Horn, P. T. Fletcher, and G. Gerig, "4D active cut: An interactive tool for pathological anatomy modeling," in ISBI, 2014.

[10] R. Girshick, J. Donahue, T. Darrell, and J. Malik, "Rich Feature Hierarchies for Accurate Object Detection and Semantic Segmentation," in CVPR, 2014.

[11] J. Long, E. Shelhamer, and T. Darrell, "Fully Convolutional Networks for Semantic Segmentation," in CVPR, 2015, pp. 3431-3440.

[12] L.-C. Chen, G. Papandreou, I. Kokkinos, K. Murphy, and A. L. Yuille, "Semantic Image Segmentation with Deep Convolutional Nets and Fully Connected CRFs," in ICLR, 2015.

[13] M. Havaei, A. Davy, D. Warde-Farley, A. Biard, A. Courville, Y. Bengio, C. Pal, P.-M. Jodoin, and H. Larochelle, "Brain Tumor Segmentation with Deep Neural Networks," Medical Image Analysis, vol. 35, pp. 18-31, 2016.

[14] K. Kamnitsas, C. Ledig, V. F. J. Newcombe, J. P. Simpson, A. D. Kane, D. K. Menon, D. Rueckert, and B. Glocker, "Efficient multi-scale 3D CNN with fully connected CRF for accurate brain lesion segmentation," Medical Image Analysis, vol. 36, pp. 61-78, 2017.

[15] F. Yu and V. Koltun, "Multi-Scale Context Aggregation By Dilated Convolutions," in ICLR, 2016.

[16] L.-C. Chen, G. Papandreou, I. Kokkinos, K. Murphy, and A. L. Yuille, "DeepLab: Semantic Image Segmentation with Deep Convolutional Nets, Atrous Convolution, and Fully Connected CRFs," arXiv preprint arXiv:1606.00915, 2016.

[17] S. Zheng, S. Jayasumana, B. Romera-Paredes, V. Vineet, Z. Su, D. Du, C. Huang, and P. H. S. Torr, "Conditional Random Fields as Recurrent Neural Networks," in ICCV, 2015.

[18] P Cicek, A. Abdulkadir, S. S. Lienkamp, T. Brox, and O. Ronneberger, "3D U-Net: Learning Dense Volumetric Segmentation from Sparse Annotation," in MICCAI, 2016.

[19] D. Lin, J. Dai, J. Jia, K. He, and J. Sun, "ScribbleSup: Scribble-Supervised Convolutional Networks for Semantic Segmentation," in CVPR, 2016.

[20] M. Rajchl, M. Lee, O. Oktay, K. Kamnitsas, J. Passerat-Palmbach, W. Bai, M. Rutherford, J. Hajnal, B. Kainz, and D. Rueckert, "DeepCut: Object Segmentation from Bounding Box Annotations using Convolutional Neural Networks," TMI, vol. PP, no. 99, pp. 1-1, 2016.

[21] N. Xu, B. Price, S. Cohen, J. Yang, and T. Huang, "Deep Interactive Object Selection," in CVPR, 2016, pp. 373-381.

[22] Y. LeCun, B. Boser, J. S. Denker, D. Henderson, R. E. Howard, W. Hubbard, and L. D. Jackel, "Backpropagation Applied to Handwritten Zip Code Recognition," Neural Computation, vol. 1, no. 4, pp. 541-551, 1989.

[23] A. Krizhevsky, I. Sutskever, and G. E. Hinton, "ImageNet classification with deep convolutional neural networks," in NIPS, 2012.

[24] K. Simonyan and A. Zisserman, "Very deep convolutional networks for large-scale image recognition," in ICLR, 2015.

[25] C. Szegedy, W. Liu, Y. Jia, P. Sermanet, S. Reed, D. Anguelov, D. Erhan, V. Vanhoucke, and A. Rabinovich, "Going deeper with convolutions," in CVPR, 2015.

[26] K. He, X. Zhang, S. Ren, and J. Sun, "Deep Residual Learning for Image Recognition," in CVPR, 2016.

[27] A. Prasoon, K. Petersen, C. Igel, F. Lauze, E. Dam, and M. Nielsen, "Deep feature learning for knee cartilage segmentation using a triplanar convolutional neural network," in MICCAI, 2013.

[28] B. Hariharan, P. Arbel_ez, R. Girshick, and J. Malik, "Simultaneous Detection and Segmentation," in ECCV, 2014.

[29] M. S. Hefny, T. Okada, M. Hori, Y. Sato, and R. E. Ellis, "U-Net: Convolutional Networks for Biomedical Image Segmentation," in MICCAI, 2015, pp. 234-241.

[30] F. Milletari, N. Navab, and S.-A. Ahmadi, "V-Net: Fully Convolutional Neural Networks for Volumetric Medical Image Segmentation," in IC3DV, 2016, pp. 565-571.

[31] P. Ondruska, J. Dequaire, D. Z. Wang, and I. Posner, "End-to-End Tracking and Semantic Segmentation Using Recurrent Neural Networks," in Robotics: Science and Systems, Workshop on Limits and Potentials of Deep Learning in Robotics, 2016.

[32] J. Dai, K. He, Y. Li, S. Ren, and J. Sun, "Instance-sensitive Fully Convolutional Networks," in ECCV, 2016.

[33] C. Lea, R. Vidal, A. Reiter, and G. D. Hager, "Temporal Convolutional Networks: A Unified Approach to Action Segmentation," in ECCV, 2016.

[34] G. Lin, C. Shen, I. Reid, and A. van dan Hengel, "Efficient piecewise training of deep structured models for semantic segmentation," in CVPR, 2016.

[35] P. Pinheiro and R. Collobert, "Recurrent convolutional neural networks for scene labeling," in ICML, 2014.

[36] B. Hariharan, P. Arbeláez, R. Girshick, and J. Malik, "Hypercolumns for object segmentation and fine-grained localization," in CVPR, 2015.

[37] C. J. Armstrong, B. L. Price, and W. A. Barrett, "Interactive segmentation of image volumes with Live Surface," Computers and Graphics (Pergamon), vol. 31, no. 2, pp. 212-229, 2007.

[38] J. E. Cates, A. E. Lefohn, and R. T. Whitaker, "GIST: An interactive, GPU-based level set segmentation tool for 3D medical images," Medical Image Analysis, vol. 8, no. 3, pp. 217-231, 2004.

[39] S. A. Haider, M. J. Shafiee, A. Chung, F. Khalvati, A. Oikonomou, A. Wong, and M. A. Haider, "Single-click, semi-automatic lung nodule contouring using hierarchical conditional random fields," in ISBI, 2015.

[40] X. Bai and G. Sapiro, "A Geodesic Framework for Fast Interactive Image and Video Segmentation and Matting," in ICCV, October 2007.

[41] O. Barinova, R. Shapovalov, S. Sudakov, and A. Velizhev, "Online Random Forest for Interactive Image Segmentation," in EEML, 2012.

[42] L. Wang, F. Shi, P. T. Yap, J. H. Gilmore, W. Lin, and D. Shen, "4D Multi-Modality Tissue Segmentation of Serial Infant Images," PLoS ONE, vol. 7, no. 9, 2012.

[43] Y. Boykov and V. Kolmogorov, "An experimental comparison of min-cut/max-flow algorithms for energy minimization in vision," PAMI, vol. 26, no. 9, pp. 1124-1137, 2004.

[44] J. Yuan, E. Bae, and X. C. Tai, "A study on continuous max-flow and min-cut approaches," in CVPR, 2010.

[45] T. Toyoda and O. Hasegawa, "Random field model for integration of local information and global information," PAMI, vol. 30, no. 8, pp. 1483-1489, 2008.

[46] P. Krähenbühl and V. Koltun, "Efficient inference in fully connected CRFs with gaussian edge potentials," in NIPS, 2011.

[47] M. Szummer, P. Kohli, and D. Hoiem, "Learning CRFs using graph cuts," in ECCV, 2008.

[48] J. I. Orlando and M. Blaschko, "Learning Fully-Connected CRFs for Blood Vessel Segmentation in Retinal Images," in MICCAI, 2014.

[49] J. Domke, "Learning graphical model parameters with approximate marginal inference," PAMI, vol. 35, no. 10, pp. 2454-2467, 2013.

[50] A. Adams, J. Baek, and M. A. Davis, "Fast high-dimensional filtering using the permutohedral lattice," Computer Graphics Forum, vol. 29, no. 2, pp. 753-762, 2010.

[51] R. Vemulapalli, O. Tuzel, M.-Y. Liu, and R. Chellappa, "Gaussian Conditional Random Field Network for Semantic Segmentation," in CVPR, 2016.

[52] F. Liu, C. Shen, and G. Lin, "Deep Convolutional Neural Fields for Depth Estimation from a Single Image," in CVPR, 2014.

[53] A. Kirillov, S. Zheng, D. Schlesinger, W. Forkel, A. Zelenin, P. Torr, and C. Rother, "Efficient Likelihood Learning of a Generic CNN-CRF Model for Semantic Segmentation," in ACCV, 2016.

[54] V. Kolmogorov and R. Zabih, "What Energy Functions Can Be Minimized via Graph Cuts?" PAMI, vol. 26, no. 2, pp. 147-159, 2004.

[55] D. Han, J. Bayouth, Q. Song, A. Taurani, M. Sonka, J. Buatti, and X. Wu, "Globally optimal tumor segmentation in PET-CT images: A graph-based co-segmentation method," in IPMI, 2011.

[56] Y. Jia, E. Shelhamer, J. Donahue, S. Karayev, J. Long, R. Girshick, S. Guadarrama, and T. Darrell, "Caffe: Convolutional Architecture for Fast Feature Embedding," in ACMICM, 2014.

[57] J. A. Deprest, A. W. Flake, E. Gratacos, Y. Ville, K. Hecher, K. Nicolaides, M. P. Johnson, F. I. Luks, N. S. Adzick, and M. R. Harrison, "The Making of Fetal Surgery," Prenatal Diagnosis, vol. 30, no. 7, pp. 653-667, 2010.

[58] A. Alansary, K. Kamnitsas, A. Davidson, M. Rajchl, C. Malamateniou, M. Rutherford, J. V. Hajnal, B. Glocker, D. Rueckert, and B. Kainz, "Fast Fully Automatic Segmentation of the Human Placenta from Motion Corrupted MRI," in MICCAI, 2016.

[59] G. Wang, M. A. Zuluaga, R. Pratt, M. Aertsen, T. Doel, M. Klusmann, A. L. David, J. Deprest, T. Vercauteren, and S. Ourselin, "Dynamically Balanced Online Random Forests for Interactive Scribble-Based Segmentation," in MICCAI, 2016.

[60] K. Keraudren, V. Kyriakopoulou, C. Malamateniou, M. A. Rutherford, B. Kainz, J. V. Hajnal, and D. Rueckert, "Automated Fetal Brain Segmentation from 2D MRI Slices for Motion Correction," NeuroImage, vol. 101, no. 1 Nov. 2014, pp. 633-643, 2014.

[61] K. Suzuki, H. Abe, H. MacMahon, and K. Doi, "Image-processing technique for suppressing ribs in chest radiographs by means of massive training artificial neural network (MTANN)," TMI, vol. 25, no. 4, pp. 406-416, 2006.

[62] B. van Ginneken, M. B. Stegmann, and M. Loog, "Segmentation of anatomical structures in chest radiographs using supervised methods: a comparative study on a public database," Medical Image Analysis, vol. 10, no. 1, pp. 19-40, 2006.

[63] L. Hogeweg, C. I. Sánchez, P. A. de Jong, P. Maduskar, and B. van Ginneken, "Clavicle segmentation in chest radiographs," Medical Image Analysis, vol. 16, no. 8, pp. 1490-1502, 2012.

[64] Gal, Y., Ghahramani, Z.: Dropout as a Bayesian Approximation: Representing Model Uncertainty in Deep Learning. In: ICML (2016)

[65] Tajbakhsh, N., Shin, J. Y., Gurudu, S. R., Hurst, R. T., Kendall, C. B., Gotway, M. B., Liang, J.: Convolutional Neural Networks for Medical Image Analysis: Full Training or Fine Tuning? TMI 35(5), 1299{1312 (2016)

[66] Pereira, S., Pinto, A., Alves, V., Silva, C. A.: Brain tumor segmentation using convolutional neural networks in MRI images. IEEE Trans. Med. Imag. 35(5) (2016) 1240-1251

[67] Chen, H., Dou, Q., Yu, L., Heng, P. A.: VoxResNet: Deep voxelwise residual networks for volumetric brain segmentation. arXiv:1608.05895 (2016)

[68] Havaei, M., Guizard, N., Chapados, N., Bengio, Y.: HeMIS: Hetero-modal image segmentation. In: Proc. MICCAI'16, Springer (2016) 469-477

[69] Ioannou, Y., Robertson, D., Zikic, D., Kontschieder, P., Shotton, J., Brown, M., Criminisi, A.: Decision forests, convolutional networks and the models in-between. arXiv:1603.01250 (2016)

[70] Ioannou, Y., Robertson, D., Cipolla, R., Criminisi, A.: Deep roots: Improving CNN efficiency with hierarchical filter groups. arXiv:1605.06489 (2016)

[71] Smith, L. N., Topin, N.: Deep convolutional neural network design patterns. arXiv:1611.00847 (2016)

[72] Dou, Q., Chen, H., Yu, L., Zhao, L., Qin, J., Wang, D., Mok, V. C., Shi, L., Heng, P. A.: Automatic detection of cerebral microbleeds from MR images via 3D convolutional neural networks. IEEE Transactions on Medical Imaging 35(5) (2016)

[73] Merkow, J., Kriegman, D., Marsden, A., Tu, Z.: Dense volume-to-volume vascular boundary detection. In: MICCAI (2016)

[74] Kleesiek, J., Urban, G., Hubert, A., Schwarz, D., Maier-Hein, K., Bendszus, M., Biller, A.: Deep MRI brain extraction: A 3D convolutional neural network for skull stripping. NeuroImage 129 (2016)

[75] Sankaran, S., Grady, L. J., Taylor, C. A.: Real-time sensitivity analysis of blood flow simulations to lumen segmentation uncertainty. In: MICCAI (2014)

[76] Shi, W., Zhuang, X., Wolz, R., Simon, D., Tung, K., Wang, H., Ourselin, S., Edwards, P., Razavi, R., Rueckert, D.: A multi-image graph cut approach for cardiac image segmentation and uncertainty estimation. In: International Workshop on Statistical Atlases and Computational Models of the Heart (2011)

[77] He, K., Zhang, X., Ren, S., Sun, J.: Identity mappings in deep residual networks. In: ECCV (2016)

[78] Veit, A., Wilber, M., Belongie, S.: Residual networks are exponential ensembles of relatively shallow networks. In: NIPS (2016)

[79] Luo, W., Li, Y., Urtasun, R., Zemel, R.: Understanding the effective receptive field in deep convolutional neural networks. In: NIPS (2016)

[80] Ioffe, S., Szegedy, C.: Batch normalization: Accelerating deep network training by reducing internal covariate shift. In: ICML (2015)

[81] Nyul, L. G., Udupa, J. K., Zhang, X.: New variants of a method of MRI scale standardization. IEEE Transactions on Medical Imaging 19(2) (2000)

[82] Kingma, D., Ba, J.: Adam: A method for stochastic optimization. arXiv:1412.6980 (2014)

[83] Cardoso, M. J., Modat, M., Wolz, R., Melbourne, A., Cash, D., Rueckert, D., Ourselin, S.: Geodesic information flows: Spatially-variant graphs and their application to segmentation and fusion. IEEE Transactions on Medical Imaging 34(9) (2015)

[84] Lazy Snapping, Yin Li, Jian Sun, Chi-Keung Tang, Heung-Yeung Shum, SIGGRAPH 2004

[85] R. Adams, L. Bischof, Seeded region growing, IEEE Trans. on Pattern Anal.

[86] Mach. Intell. 16 (6) (1994), 641-647 #

[87] Ribeiro, H. L., Gonzaga, A.: Hand Image Segmentation in Video Sequence by GMM: a comparative analysis. In: SIBGRAPI. pp. 357{364 (2006)

[88] Huh, M., Agrawal, P., Efros, A. A.: What makes ImageNet good for transfer learning? arXiv:1608.08614 (2016)

[89] Pereira, S., Pinto, A., Alves, V., Silva, C. A.: Brain tumor segmentation using convolutional neural networks in MRI images. IEEE Trans. Med. Imag. 35(5), 1240-1251 (2016)

[90] W. Li, G. Wang, L. Fidon, S. Ourselin, M. J. Cardoso, and T. Vercauteren, "On the Compactness, Efficiency, and Representation of 3D Convolutional Networks: Brain Parcellation as a Pretext Task," in IPMI, 2017.

[91] P. A. Yushkevich, J. Piven, H. C. Hazlett, R. G. Smith, S. Ho, J. C. Gee, and G. Gerig, "User-guided 3D active contour segmentation of anatomical structures: Significantly improved efficiency and reliability," NeuroImage, vol. 31, no. 3, pp. 1116-1128, 2006.

[92] B. H. Menze, A. Jakab, S. Bauer, J. Kalpathy-Cramer, K. Farahani, J. Kirby, Y. Burren, N. Porz, J. Slotboom, R. West, L. Lanczi, E. Gerstner, M. A. Weber, T. Arbel, B. B. Avants, N. Ayache, P. Buendia, D. L. Collins, N. Cordier, J. J. Corso, A. Criminisi, T. Das, H. Delingette, C. Demiralp, C. R. Durst, M. Dojat, S. Doyle, J. Festa, F. Forbes, E. Geremia, B. Glocker, P. Golland, X. Guo, A. Hamamci, K. M. Iftekharuddin, R. Jena, N. M. John, E. Konukoglu, D. Lashkari, J. A. Mariz, R. Meier, S. Pereira, D. Precup, S. J. Price, T. R. Raviv, S. M. Reza, M. Ryan, D. Sarikaya, L. Schwartz, H. C. Shin, J. Shotton, C. A. Silva, N. Sousa, N. K. Subbanna, G. Szekely, T. J. Taylor, O. M. Thomas, N. J. Tustison, G. Unal, F. Vasseur, M. Wintermark, D. H. Ye, L. Zhao, B. Zhao, D. Zikic, M. Prastawa, M. Reyes, and K. Van Leemput, "The Multimodal Brain Tumor Image Segmentation Benchmark (BRATS)," TMI, vol. 34, no. 10, pp. 1993-2024, 2015.

[93] E. Ram and P. Temoche, "A volume segmentation approach based on GrabCut," CLEI Electronic Journal, vol. 16, no. 2, pp. 4-4, 2013.

[94] V. Vezhnevets and V. Konouchine, "GrowCut: Interactive multi-label ND image segmentation by cellular automata," in Graphicon, 2005, pp. 150-156.

The invention claimed is:

1. A computer-implemented method for segmenting an input image, the method comprising:
   generating a first segmentation of the input image using a first machine learning system, the first segmentation comprising multiple segments;
   receiving, from a user, at least one indication, wherein each indication corresponds to a particular segment from the multiple segments, and marks one or more locations of the input image as belonging to that particular segment;
   constructing, for each segment of the multiple segments having at least one corresponding indication, a respective geodesic distance map, based on the input image and the user indications received for that segment; and
   generating a second segmentation using a second machine learning system based on the input image and the constructed geodesic distance maps.

2. The method of claim 1, wherein at least one of the first machine learning system and the second machine learning system comprises one or more neural networks, including a layered convolutional neural network (CNN).

3. The method of claim 1, wherein at least one the first machine learning system and the second machine learning system implements a conditional random field as a post-processing step to enforce inter-pixel dependency.

4. The method of claim 3, wherein the conditional random field of the second machine learning system enforces a hard constraint that each location marked by indication must be classified as belonging to the segment corresponding to that indication.

5. The method of claim 3, wherein the conditional random field of the first and/or second machine learning system utilises a freeform function for a pairwise potential between pixels.

6. The method of claim 1, wherein receiving at least one indication from a user comprises:
displaying on a screen the first segmentation superimposed on the input image;
a user entering each indication on the screen to mark one or more locations of the image as belonging to the particular segment corresponding to that indication.

7. The method of claim 1, wherein the indications are clicks and/or scribbles comprising free-form lines.

8. The method of claim 1, wherein constructing the geodesic distance map for a particular segment comprises, for each location in the input image, determining the value of said location based on the minimum geodesic distance in the input image from said location to an indication corresponding to the particular segment.

9. The method of claim 8, wherein the minimum geodesic distance is determined by calculating, along multiple different paths through the input image from said location to an indication corresponding to the particular segment, the respective geodesic distance for said path by summing a measure of local discrepancy along the path.

10. The method of claim 1, further comprising, for each particular segment for which no indication is received, generating a substantially homogeneous geodesic distance map and providing the generated geodesic distance map to the second machine learning system.

11. The method of claim 1, wherein the second segmentation is further based on the first segmentation, in addition to the input image and the constructed geodesic distance maps.

12. The method of claim 1, wherein a single geodesic map may be constructed for all segments sharing the same segment type.

13. The method of claim 1, further comprising:
determining a segmentation uncertainty map showing the uncertainty of the segmentation at different locations of the input image; and
displaying said segmentation uncertainty map to the user.

14. The method of claim 1, wherein residual connections are used to bypass parameterised layers in the machine learning system(s).

15. A computer-implemented method for segmenting an input image, the method comprising:
receiving an input image into a machine learning system for performing segmentation of the image based on a set of model parameters, the machine learning system having been trained using a previous set of training images provided with labelled segmentations, wherein the input image is received without a labelled segmentation;
performing a segmentation of the input image into multiple segments by solving jointly for: (i) a segmentation of the input image; and (ii) an updated set of model parameters for the machine learning system, whereby the machine learning system is tuned by the input image;
receiving, from a user into the machine learning system, at least one indication, wherein each indication corresponds to a particular segment from the multiple segments, and marks one or more locations of the input image as belonging to that particular segment; and
performing a further, refined, segmentation of the input image into multiple segments using the at least one indication by solving jointly for: (i) a segmentation of the input image; and (ii) an updated set of model parameters for the machine learning system.

16. The method of claim 15, further comprising constructing, for each segment of the multiple segments having at least one corresponding indication, a respective geodesic distance map, based on the input image and the user indications received for that segment, and whereby said geodesic maps are used as input for said solving jointly for: (i) a segmentation of the input image; and (ii) an updated set of model parameters for the machine learning system.

17. The method of claim 15, wherein the solving jointly comprises an iterative optimisation process which, for alternative iterations, updates (i) a proposed segmentation of the input image; and (ii) the set of model parameters.

18. A computer-implemented method for segmenting a multi-modal input image using a multi-layered machine learning system, the method comprising:
receiving an input image into the machine learning system comprising multiple imaging modalities (M-space) and generating multiple modality-conditioned features (F-space);
processing the input image by performing a first transform within one or more layers of the machine learning system across F-space and a second transform within one or more further layers of the machine learning system across M-space to perform the segmentation, wherein the machine learning system comprises:
a back-end which processes the input image by performing said first and second transforms, and which merges the output from said first and second transforms across M-space; and
a front-end which receives the back-end merged output and generates therefrom a segmentation of the input image based on a monomodal-like analysis.

* * * * *